United States Patent
Zuker et al.

(10) Patent No.: US 7,977,060 B2
(45) Date of Patent: *Jul. 12, 2011

(54) MAMMALIAN SWEET TASTE RECEPTORS

(75) Inventors: Charles S. Zuker, San Diego, CA (US); Nicholas J. P. Ryba, Bethesda, MD (US); Gregory A. Nelson, San Diego, CA (US); Mark A. Hoon, Kensington, MA (US); Jayaram Chandrashekar, San Diego, CA (US); Yifeng Zhang, Boston, MA (US)

(73) Assignees: Regents of the University of California, Oakland, CA (US); The United States of America as represented by NIH, Washington, DC (US)

( * ) Notice: Subject to any disclaimer, the term of this patent is extended or adjusted under 35 U.S.C. 154(b) by 65 days.

This patent is subject to a terminal disclaimer.

(21) Appl. No.: 12/147,415

(22) Filed: Jun. 26, 2008

(65) Prior Publication Data

US 2009/0098580 A1 Apr. 16, 2009

Related U.S. Application Data

(63) Continuation of application No. 09/927,315, filed on Aug. 10, 2001, now Pat. No. 7,402,400.

(60) Provisional application No. 60/302,898, filed on Jul. 3, 2001.

(51) Int. Cl.
*C07K 14/705* (2006.01)
*C12N 15/12* (2006.01)
*G01N 33/566* (2006.01)

(52) U.S. Cl. ........ 435/7.21; 435/7.1; 435/7.2; 435/69.1; 435/252.3; 435/320.1; 436/501; 530/350

(58) Field of Classification Search .................... None
See application file for complete search history.

(56) References Cited

U.S. PATENT DOCUMENTS

| 7,402,400 B2 | 7/2008 | Zuker et al. |
| 2002/0160424 A1 | 10/2002 | Adler et al. |

FOREIGN PATENT DOCUMENTS

| CA | 2451317 | 1/2003 |
| EP | 1270724 A2 | 1/2003 |
| WO | WO 00/06593 A1 | 2/2000 |
| WO | WO 01/64882 A2 | 9/2001 |
| WO | WO 01/66563 A2 | 9/2001 |
| WO | WO 01/83749 A2 | 11/2001 |
| WO | WO 02/064631 A2 | 8/2002 |
| WO | WO 02/086079 A | 10/2002 |
| WO | WO 03/001876 A2 | 1/2003 |
| WO | WO 03/025137 A2 | 3/2003 |

OTHER PUBLICATIONS

Ariyasu, T. et al., "Taste Receptor TIR3 is an Essential Molecule for the Cellular Recognition of the Disaccharide Trehalose," In Vitro Cellular & Developmental Biology, Jan. and Feb. 2003, pp. 80-88, vol. 39, No. 1/2.
Bachmanov, A. A. et al., "Positional Cloning of the Mouse Saccharin Preference (SAC) Locus," Chemical Senses, Sep. 2001, pp. 925-933, vol. 26, No. 26, IRL Press, Oxford, GB.
European Communication Pursuant to Article 96(2) EPC, EP 04794142.2, May 15, 2007, 4 pages.
European Examination Report, European Application No. 02749804.7, Feb. 23, 2009, 9 pages.
European Supplementary Search Report, European Application No. 02749804.7, Jul. 11, 2007, 8 pages.
European Supplementary Search Report, European Application No. 02749804.7, Dec. 3, 2007, 11 pages.
Hoon et al., "Putative Mammalian Taste Receptors: A Class of Taste-Specific GPCRs with Distinct Topographic Selectivity," Cell, Feb. 19, 1999, pp. 541-551, vol. 96, Cell Press.
Kitagawa, M., et al., "Molecular Genetic Identification of a Candidate Receptor Gene for Sweet Taste," Biochemical and Biophysical Research Communications, Apr. 27, 2001, pp. 236-242, vol., 283, No. 1.
Li et al., "Human Receptors for Sweet and Umami Taste," PNAS, Apr. 2, 2002, pp. 4692-4696, vol. 99, No. 7.
Li, X. et al., "High-Resolution Genetic Mapping of the Saccharin Preference Locus (Sac) and the Putative Sweet Taste Receptor (T1R1) Gene (Gpr70) to Mouse Distal Chromosome 4," Mammalian Genome, Jan. 2001, pp. 13-16, vol. 12, No. 1.
Max, M. et al., "Tas1r3, Encoding a New Candidate Taste Receptor, is Allelic to the Sweet Responsiveness Locus Sac," Nature Genetics, May 2001, pp. 492-498, vol. 28.
Montmayeur et al., "A Candidate Taste Receptor Gene Near a Sweet Taste Locus," Nature Neuroscience, May 2001, pp. 492-498, vol. 4, No. 5.
Nelson et al., "An Amino-Acid Taste Receptor," Nature, DOI 10.1038/nature726 www.nature.com, Feb. 24, 2002, 4 pages.
Nelson et al., "Mammalian Sweet Taste Receptors," Cell, Aug. 10, 2001, pp. 381-390, vol. 106, Cell Press.
Sainz, E. et al., "Identification of a Novel Member of the T1R Family of Putative Taste Receptors," Journal of Neurochemistry, May 2001, pp. 896-903, vol. 77, No. 3.
Canadian Office Action, Canadian Application No. 2,452,716, Nov. 3, 2009, 5 pages.
Japanese Office Action, Japanese Application No. 2003-510918, Aug. 20, 2009, 4 pages.
United States Office Action, U.S. Appl. No. 12/121,576, Jan. 6, 2010, 6 pages.
United States Office Action, U.S. Appl. No. 12/257,290, Mar. 12, 2010, 11 pages.

*Primary Examiner* — John Ulm
(74) *Attorney, Agent, or Firm* — Fenwick & West LLP

(57) ABSTRACT

The present invention provides isolated nucleic acid and amino acid sequences of sweet taste receptors comprising two heterologous G-protein coupled receptor polypeptides from the T1R family of sensory G-protein coupled receptors, antibodies to such receptors, methods of detecting such nucleic acids and receptors, and methods of screening for modulators of sweet taste receptors.

29 Claims, 10 Drawing Sheets

SEQUENCE LISTING

<160> NUMBER OF SEQ ID NOS: 25

<210> SEQ ID NO 1
<211> LENGTH: 840
<212> TYPE: PRT

<213> ORGANISM: Rattus sp.
<220> FEATURE:
<223> OTHER INFORMATION: rat T1R1 sweet taste receptor

<400> SEQUENCE: 1

```
Met Leu Phe Trp Ala Ala His Leu Leu Ser Leu Gln Leu Val Tyr
  1               5                  10                  15

Cys Trp Ala Phe Ser Cys Gln Arg Thr Glu Ser Ser Pro Gly Phe Ser
             20                  25                  30

Leu Pro Gly Asp Phe Leu Leu Ala Gly Leu Phe Ser Leu His Gly Asp
         35                  40                  45

Cys Leu Gln Val Arg His Arg Pro Leu Val Thr Ser Cys Asp Arg Pro
 50                  55                  60

Asp Ser Phe Asn Gly His Gly Tyr His Leu Phe Gln Ala Met Arg Phe
 65                  70                  75                  80

Thr Val Glu Glu Ile Asn Asn Ser Ser Ala Leu Leu Pro Asn Ile Thr
                 85                  90                  95

Leu Gly Tyr Glu Leu Tyr Asp Val Cys Ser Glu Ser Ala Asn Val Tyr
            100                 105                 110

Ala Thr Leu Arg Val Leu Ala Leu Gln Gly Pro Arg His Ile Glu Ile
        115                 120                 125

Gln Lys Asp Leu Arg Asn His Ser Ser Lys Val Val Ala Phe Ile Gly
130                 135                 140

Pro Asp Asn Thr Asp His Ala Val Thr Thr Ala Ala Leu Leu Gly Pro
145                 150                 155                 160

Phe Leu Met Pro Leu Val Ser Tyr Glu Ala Ser Ser Val Val Leu Ser
                165                 170                 175

Ala Lys Arg Lys Phe Pro Ser Phe Leu Arg Thr Val Pro Ser Asp Arg
            180                 185                 190

His Gln Val Glu Val Met Val Gln Leu Leu Gln Ser Phe Gly Trp Val
        195                 200                 205

Trp Ile Ser Leu Ile Gly Ser Tyr Gly Asp Tyr Gly Gln Leu Gly Val
210                 215                 220

Gln Ala Leu Glu Glu Leu Ala Val Pro Arg Gly Ile Cys Val Ala Phe
225                 230                 235                 240

Lys Asp Ile Val Pro Phe Ser Ala Arg Val Gly Asp Pro Arg Met Gln
                245                 250                 255

Ser Met Met Gln His Leu Ala Gln Ala Arg Thr Thr Val Val Val Val
            260                 265                 270

Phe Ser Asn Arg His Leu Ala Arg Val Phe Phe Arg Ser Val Val Leu
        275                 280                 285

Ala Asn Leu Thr Gly Lys Val Trp Val Ala Ser Glu Asp Trp Ala Ile
290                 295                 300

Ser Thr Tyr Ile Thr Ser Val Thr Gly Ile Gln Gly Ile Gly Thr Val
305                 310                 315                 320

Leu Gly Val Ala Val Gln Gln Arg Gln Val Pro Gly Leu Lys Glu Phe
                325                 330                 335

Glu Glu Ser Tyr Val Arg Ala Val Thr Ala Ala Pro Ser Ala Cys Pro
            340                 345                 350

Glu Gly Ser Trp Cys Ser Thr Asn Gln Leu Cys Arg Glu Cys His Thr
        355                 360                 365

Phe Thr Thr Arg Asn Met Pro Thr Leu Gly Ala Phe Ser Met Ser Ala
370                 375                 380

Ala Tyr Arg Val Tyr Glu Ala Val Tyr Ala Val Ala His Gly Leu His
385                 390                 395                 400
```

```
Gln Leu Leu Gly Cys Thr Ser Glu Ile Cys Ser Arg Gly Pro Val Tyr
                405                 410                 415

Pro Trp Gln Leu Leu Gln Gln Ile Tyr Lys Val Asn Phe Leu Leu His
        420                 425                 430

Glu Asn Thr Val Ala Phe Asp Asp Asn Gly Asp Thr Leu Gly Tyr Tyr
            435                 440                 445

Asp Ile Ile Ala Trp Asp Trp Asn Gly Pro Glu Trp Thr Phe Glu Ile
450                 455                 460

Ile Gly Ser Ala Ser Leu Ser Pro Val His Leu Asp Ile Asn Lys Thr
465                 470                 475                 480

Lys Ile Gln Trp His Gly Lys Asn Asn Gln Val Pro Val Ser Val Cys
                485                 490                 495

Thr Thr Asp Cys Leu Ala Gly His His Arg Val Val Gly Ser His
                500                 505                 510

His Cys Cys Phe Glu Cys Val Pro Cys Glu Ala Gly Thr Phe Leu Asn
        515                 520                 525

Met Ser Glu Leu His Ile Cys Gln Pro Cys Gly Thr Glu Glu Trp Ala
        530                 535                 540

Pro Lys Glu Ser Thr Thr Cys Phe Pro Arg Thr Val Glu Phe Leu Ala
545                 550                 555                 560

Trp His Glu Pro Ile Ser Leu Val Leu Ile Ala Ala Asn Thr Leu Leu
                565                 570                 575

Leu Leu Leu Leu Val Gly Thr Ala Gly Leu Phe Ala Trp His Phe His
            580                 585                 590

Thr Pro Val Val Arg Ser Ala Gly Gly Arg Leu Cys Phe Leu Met Leu
            595                 600                 605

Gly Ser Leu Val Ala Gly Ser Cys Ser Phe Tyr Ser Phe Phe Gly Glu
            610                 615                 620

Pro Thr Val Pro Ala Cys Leu Leu Arg Gln Pro Leu Phe Ser Leu Gly
625                 630                 635                 640

Phe Ala Ile Phe Leu Ser Cys Leu Thr Ile Arg Ser Phe Gln Leu Val
                645                 650                 655

Ile Ile Phe Lys Phe Ser Thr Lys Val Pro Thr Phe Tyr Arg Thr Trp
            660                 665                 670

Ala Gln Asn His Gly Ala Gly Leu Phe Val Ile Val Ser Ser Thr Val
            675                 680                 685

His Leu Leu Ile Cys Leu Thr Trp Leu Val Met Trp Thr Pro Arg Pro
    690                 695                 700

Thr Arg Glu Tyr Gln Arg Phe Pro His Leu Val Ile Leu Glu Cys Thr
705                 710                 715                 720

Glu Val Asn Ser Val Gly Phe Leu Leu Ala Phe Thr His Asn Ile Leu
                725                 730                 735

Leu Ser Ile Ser Thr Phe Val Cys Ser Tyr Leu Gly Lys Glu Leu Pro
            740                 745                 750

Glu Asn Tyr Asn Glu Ala Lys Cys Val Thr Phe Ser Leu Leu Leu Asn
        755                 760                 765

Phe Val Ser Trp Ile Ala Phe Phe Thr Met Ala Ser Ile Tyr Gln Gly
        770                 775                 780

Ser Tyr Leu Pro Ala Val Asn Val Leu Ala Gly Leu Thr Thr Leu Ser
785                 790                 795                 800

Gly Gly Phe Ser Gly Tyr Phe Leu Pro Lys Cys Tyr Val Ile Leu Cys
                805                 810                 815

Arg Pro Glu Leu Asn Asn Thr Glu His Phe Gln Ala Ser Ile Gln Asp
```

```
                    820                 825                 830
Tyr Thr Arg Arg Cys Gly Thr Thr
                835                 840

<210> SEQ ID NO 2
<211> LENGTH: 842
<212> TYPE: PRT
<213> ORGANISM: Mus musculus
<220> FEATURE:
<223> OTHER INFORMATION: mouse T1R1 sweet taste receptor

<400> SEQUENCE: 2

Met Leu Phe Trp Ala Ala His Leu Leu Ser Leu Gln Leu Ala Val
 1               5                  10                  15

Ala Tyr Cys Trp Ala Phe Ser Cys Gln Arg Thr Glu Ser Ser Pro Gly
                20                  25                  30

Phe Ser Leu Pro Gly Asp Phe Leu Leu Ala Gly Leu Phe Ser Leu His
                35                  40                  45

Ala Asp Cys Leu Gln Val Arg His Arg Pro Leu Val Thr Ser Cys Asp
     50                  55                  60

Arg Ser Asp Ser Phe Asn Gly His Gly Tyr His Leu Phe Gln Ala Met
 65                  70                  75                  80

Arg Phe Thr Val Glu Glu Ile Asn Asn Ser Thr Ala Leu Leu Pro Asn
                85                  90                  95

Ile Thr Leu Gly Tyr Glu Leu Tyr Asp Val Cys Ser Glu Ser Ser Asn
                100                 105                 110

Val Tyr Ala Thr Leu Arg Val Pro Ala Gln Gln Gly Thr Gly His Leu
                115                 120                 125

Glu Met Gln Arg Asp Leu Arg Asn His Ser Ser Lys Val Val Ala Leu
    130                 135                 140

Ile Gly Pro Asp Asn Thr Asp His Ala Val Thr Thr Ala Ala Leu Leu
145                 150                 155                 160

Ser Pro Phe Leu Met Pro Leu Val Ser Tyr Glu Ala Ser Ser Val Ile
                165                 170                 175

Leu Ser Gly Lys Arg Lys Phe Pro Ser Phe Leu Arg Thr Ile Pro Ser
                180                 185                 190

Asp Lys Tyr Gln Val Glu Val Ile Val Arg Leu Leu Gln Ser Phe Gly
                195                 200                 205

Trp Val Trp Ile Ser Leu Val Gly Ser Tyr Gly Asp Tyr Gly Gln Leu
    210                 215                 220

Gly Val Gln Ala Leu Glu Glu Leu Ala Thr Pro Arg Gly Ile Cys Val
225                 230                 235                 240

Ala Phe Lys Asp Val Val Pro Leu Ser Ala Gln Ala Gly Asp Pro Arg
                245                 250                 255

Met Gln Arg Met Met Leu Arg Leu Ala Arg Ala Arg Thr Thr Val Val
                260                 265                 270

Val Val Phe Ser Asn Arg His Leu Ala Gly Val Phe Phe Arg Ser Val
                275                 280                 285

Val Leu Ala Asn Leu Thr Gly Lys Val Trp Ile Ala Ser Glu Asp Trp
    290                 295                 300

Ala Ile Ser Thr Tyr Ile Thr Asn Val Pro Gly Ile Gln Gly Ile Gly
305                 310                 315                 320

Thr Val Leu Gly Val Ala Ile Gln Gln Arg Gln Val Pro Gly Leu Lys
                325                 330                 335

Glu Phe Glu Glu Ser Tyr Val Gln Ala Val Met Gly Ala Pro Arg Thr
                340                 345                 350
```

-continued

Cys Pro Glu Gly Ser Trp Cys Gly Thr Asn Gln Leu Cys Arg Glu Cys
        355                 360                 365

His Ala Phe Thr Thr Trp Asn Met Pro Glu Leu Gly Ala Phe Ser Met
        370                 375                 380

Ser Ala Ala Tyr Asn Val Tyr Glu Ala Val Tyr Ala Val Ala His Gly
385                 390                 395                 400

Leu His Gln Leu Leu Gly Cys Thr Ser Gly Thr Cys Ala Arg Gly Pro
                405                 410                 415

Val Tyr Pro Trp Gln Leu Leu Gln Gln Ile Tyr Lys Val Asn Phe Leu
            420                 425                 430

Leu His Lys Lys Thr Val Ala Phe Asp Asp Lys Gly Asp Pro Leu Gly
        435                 440                 445

Tyr Tyr Asp Ile Ile Ala Trp Asp Trp Asn Gly Pro Glu Trp Thr Phe
    450                 455                 460

Glu Val Ile Gly Ser Ala Ser Leu Ser Pro Val His Leu Asp Ile Asn
465                 470                 475                 480

Lys Thr Lys Ile Gln Trp His Gly Lys Asn Asn Gln Val Pro Val Ser
                485                 490                 495

Val Cys Thr Arg Asp Cys Leu Glu Gly His His Arg Leu Val Met Gly
            500                 505                 510

Ser His His Cys Cys Phe Glu Cys Met Pro Cys Glu Ala Gly Thr Phe
    515                 520                 525

Leu Asn Thr Ser Glu Leu His Thr Cys Gln Pro Cys Gly Thr Glu Glu
        530                 535                 540

Trp Ala Pro Glu Gly Ser Ser Ala Cys Phe Ser Arg Thr Val Glu Phe
545                 550                 555                 560

Leu Gly Trp His Glu Pro Ile Ser Leu Val Leu Leu Ala Ala Asn Thr
                565                 570                 575

Leu Leu Leu Leu Leu Leu Ile Gly Thr Ala Gly Leu Phe Ala Trp Arg
            580                 585                 590

Leu His Thr Pro Val Val Arg Ser Ala Gly Gly Arg Leu Cys Phe Leu
        595                 600                 605

Met Leu Gly Ser Leu Val Ala Gly Ser Cys Ser Leu Tyr Ser Phe Phe
    610                 615                 620

Gly Lys Pro Thr Val Pro Ala Cys Leu Leu Arg Gln Pro Leu Phe Ser
625                 630                 635                 640

Leu Gly Phe Ala Ile Phe Leu Ser Cys Leu Thr Ile Arg Ser Phe Gln
                645                 650                 655

Leu Val Ile Ile Phe Lys Phe Ser Thr Lys Val Pro Thr Phe Tyr His
            660                 665                 670

Thr Trp Ala Gln Asn His Gly Ala Gly Ile Phe Val Ile Val Ser Ser
        675                 680                 685

Thr Val His Leu Phe Leu Cys Leu Thr Trp Leu Ala Met Trp Thr Pro
    690                 695                 700

Arg Pro Thr Arg Glu Tyr Gln Arg Phe Pro His Leu Val Ile Leu Glu
705                 710                 715                 720

Cys Thr Glu Val Asn Ser Val Gly Phe Leu Val Ala Phe Ala His Asn
                725                 730                 735

Ile Leu Leu Ser Ile Ser Thr Phe Val Cys Ser Tyr Leu Gly Lys Glu
            740                 745                 750

Leu Pro Glu Asn Tyr Asn Glu Ala Lys Cys Val Thr Phe Ser Leu Leu
        755                 760                 765

Leu His Phe Val Ser Trp Ile Ala Phe Phe Thr Met Ser Ser Ile Tyr

-continued

```
                770                 775                 780
Gln Gly Ser Tyr Leu Pro Ala Val Asn Val Leu Ala Gly Leu Ala Thr
785                 790                 795                 800

Leu Ser Gly Gly Phe Ser Gly Tyr Phe Leu Pro Lys Cys Tyr Val Ile
                805                 810                 815

Leu Cys Arg Pro Glu Leu Asn Asn Thr Glu His Phe Gln Ala Ser Ile
                820                 825                 830

Gln Asp Tyr Thr Arg Arg Cys Gly Thr Thr
            835                 840

<210> SEQ ID NO 3
<211> LENGTH: 777
<212> TYPE: PRT
<213> ORGANISM: Homo sapiens
<220> FEATURE:
<223> OTHER INFORMATION: human T1R1 sweet taste receptor

<400> SEQUENCE: 3

Arg Ser Cys Ser Phe Asn Glu His Gly Tyr His Leu Phe Gln Ala Met
  1               5                  10                  15

Arg Leu Gly Val Glu Glu Ile Asn Asn Ser Thr Ala Leu Leu Pro Asn
                 20                  25                  30

Ile Thr Leu Gly Tyr Gln Leu Tyr Asp Val Cys Ser Asp Ser Ala Asn
             35                  40                  45

Val Tyr Ala Thr Leu Arg Val Leu Ser Leu Pro Gly Gln His His Ile
         50                  55                  60

Glu Leu Gln Gly Asp Leu Leu His Tyr Ser Pro Thr Val Leu Ala Val
 65                  70                  75                  80

Ile Gly Pro Asp Ser Thr Asn Arg Ala Ala Thr Thr Ala Ala Leu Leu
                 85                  90                  95

Ser Pro Phe Leu Val His Ile Ser Tyr Ala Ala Ser Ser Glu Thr Leu
            100                 105                 110

Ser Val Lys Arg Gln Tyr Pro Ser Phe Leu Arg Thr Ile Pro Asn Asp
        115                 120                 125

Lys Tyr Gln Val Glu Thr Met Val Leu Leu Leu Gln Lys Phe Gly Trp
130                 135                 140

Thr Trp Ile Ser Leu Val Gly Ser Ser Asp Asp Tyr Gly Gln Leu Gly
145                 150                 155                 160

Val Gln Ala Leu Glu Asn Gln Ala Leu Val Arg Gly Ile Cys Ile Ala
                165                 170                 175

Phe Lys Asp Ile Met Pro Phe Ser Ala Gln Val Gly Asp Glu Arg Met
            180                 185                 190

Gln Cys Leu Met Arg His Leu Ala Gln Ala Gly Ala Thr Val Val Val
        195                 200                 205

Val Phe Ser Ser Arg Gln Leu Ala Arg Val Phe Phe Glu Ser Val Val
    210                 215                 220

Leu Thr Asn Leu Thr Gly Lys Val Trp Val Ala Ser Glu Ala Trp Ala
225                 230                 235                 240

Leu Ser Arg His Ile Thr Gly Val Pro Gly Ile Gln Arg Ile Gly Met
                245                 250                 255

Val Leu Gly Val Ala Ile Gln Lys Arg Ala Val Pro Gly Leu Lys Ala
            260                 265                 270

Phe Glu Glu Ala Tyr Ala Arg Ala Asp Lys Glu Ala Pro Arg Pro Cys
        275                 280                 285

His Lys Gly Ser Trp Cys Ser Ser Asn Gln Leu Cys Arg Glu Cys Gln
    290                 295                 300
```

```
Ala Phe Met Ala His Thr Met Pro Lys Leu Lys Ala Phe Ser Met Ser
305                 310                 315                 320

Ser Ala Tyr Asn Ala Tyr Arg Ala Val Tyr Ala Val Ala His Gly Leu
            325                 330                 335

His Gln Leu Leu Gly Cys Ala Ser Glu Leu Cys Ser Arg Gly Arg Val
        340                 345                 350

Tyr Pro Trp Gln Leu Leu Glu Gln Ile His Lys Val His Phe Leu Leu
    355                 360                 365

His Lys Asp Thr Val Ala Phe Asn Asp Asn Arg Asp Pro Leu Ser Ser
370                 375                 380

Tyr Asn Ile Ile Ala Trp Asp Trp Asn Gly Pro Lys Trp Thr Phe Thr
385                 390                 395                 400

Val Leu Gly Ser Ser Thr Trp Ser Pro Val Gln Leu Asn Ile Asn Glu
            405                 410                 415

Thr Lys Ile Gln Trp His Gly Lys Asn His Gln Val Pro Lys Ser Val
        420                 425                 430

Cys Ser Ser Asp Cys Leu Glu Gly His Gln Arg Val Val Thr Gly Phe
    435                 440                 445

His His Cys Cys Phe Glu Cys Val Pro Cys Gly Ala Gly Thr Phe Leu
450                 455                 460

Asn Lys Ser Glu Leu Tyr Arg Cys Gln Pro Cys Gly Thr Glu Glu Trp
465                 470                 475                 480

Ala Pro Glu Gly Ser Gln Thr Cys Phe Pro Arg Thr Val Val Phe Leu
            485                 490                 495

Ala Leu Arg Glu His Thr Ser Trp Val Leu Leu Ala Ala Asn Thr Leu
        500                 505                 510

Leu Leu Leu Leu Leu Leu Gly Thr Ala Gly Leu Phe Ala Trp His Leu
    515                 520                 525

Asp Thr Pro Val Val Arg Ser Ala Gly Gly Arg Leu Cys Phe Leu Met
530                 535                 540

Leu Gly Ser Leu Ala Ala Gly Ser Gly Ser Leu Tyr Gly Phe Phe Gly
545                 550                 555                 560

Glu Pro Thr Arg Pro Ala Cys Leu Leu Arg Gln Ala Leu Phe Ala Leu
            565                 570                 575

Gly Phe Thr Ile Phe Leu Ser Cys Leu Thr Val Arg Ser Phe Gln Leu
        580                 585                 590

Ile Ile Ile Phe Lys Phe Ser Thr Lys Val Pro Thr Phe Tyr His Ala
    595                 600                 605

Trp Val Gln Asn His Gly Ala Gly Leu Phe Val Met Ile Ser Ser Ala
610                 615                 620

Ala Gln Leu Leu Ile Cys Leu Thr Trp Leu Val Val Trp Thr Pro Leu
625                 630                 635                 640

Pro Ala Arg Glu Tyr Gln Arg Phe Pro His Leu Val Met Leu Glu Cys
            645                 650                 655

Thr Glu Thr Asn Ser Leu Gly Phe Ile Leu Ala Phe Leu Tyr Asn Gly
        660                 665                 670

Leu Leu Ser Ile Ser Ala Phe Ala Cys Ser Tyr Leu Gly Lys Asp Leu
    675                 680                 685

Pro Glu Asn Tyr Asn Glu Ala Lys Cys Val Thr Phe Ser Leu Leu Phe
690                 695                 700

Asn Phe Val Ser Trp Ile Ala Phe Phe Thr Thr Ala Ser Val Tyr Asp
705                 710                 715                 720

Gly Lys Tyr Leu Pro Ala Ala Asn Met Met Ala Gly Leu Ser Ser Leu
```

```
                725                 730                 735
Ser Ser Gly Phe Gly Gly Tyr Phe Leu Pro Lys Cys Tyr Val Ile Leu
            740                 745                 750
Cys Arg Pro Asp Leu Asn Ser Thr Glu His Phe Gln Ala Ser Ile Gln
            755                 760                 765
Asp Tyr Thr Arg Arg Cys Gly Ser Thr
            770                 775

<210> SEQ ID NO 4
<211> LENGTH: 2771
<212> TYPE: DNA
<213> ORGANISM: Rattus sp.
<220> FEATURE:
<223> OTHER INFORMATION: rat T1R1 sweet taste receptor

<400> SEQUENCE: 4
attcacatca gagctgtgct cagccatgct gggcagaggg acgacggctg ccagcatgc       60 tcttctgggc tgctcacctg ctgctcagcc tgcagttggt ctactgctgg gctttcagct     120
gccaaaggac agagtcctct ccaggcttca gccttcctgg ggacttcctc cttgcaggtc     180
tgttctccct ccatggtgac tgtctgcagg tgagacacag acctctggtg acaagttgtg     240
acaggcccga cagcttcaac ggccatggct accacctctt ccaagccatg cggttcactg     300
ttgaggagat aaacaactcc tcggccctgc ttcccaacat cacccctggg tatgagctgt     360
acgacgtgtg ctcagaatct gccaatgtgt atgccaccct gagggtgctt gccctgcaag     420
ggccccgcca catagagata cagaaagacc ttcgcaacca ctcctccaag gtggtggcct     480
tcatcgggcc tgacaacact gaccacgctg tcactaccgc tgccttgctg gtcctttcc      540 tgatgcccct ggtcagctat gaggcaagca gcgtggtact cagtgccaag cgcaagttcc     600 cgtcttttcct tcgtaccgtc cccagtgacc ggcaccaggt ggaggtcatg gtgcagctgc    660
tgcagagttt gggtgggtg tggatctcgc tcattggcag ctacggtgat acgggcagc      720 tgggtgtgca ggcgctggag gagctggccg tgccccgggg catctgcgtc gccttcaagg    780
acatcgtgcc tttctctgcc cggggtgggtg acccgaggat gcagagcatg atgcagcatc   840
tggctcaggc caggaccacc gtggttgtgg tcttctctaa ccggcacctg gctagagtgt    900
tcttcaggtc cgtggtgctg gccaacctga ctggcaaagt gtgggtcgcc tcagaagact   960
gggccatctc cacgtacatc accagcgtga ctgggatcca aggcattggg acggtgctcg  1020
gtgtggccgt ccagcagaga caagtccctg gctgaaggag tttgaggag tcttatgtca   1080 gggctgtaac agctgctccc agcgcttgcc cggaggggtc ctggtgcagc actaaccagc   1140
tgtgccggga gtgccacacg ttcacgactc gtaacatgcc cacgcttgga gccttctcca   1200
tgagtgccgc ctacagagtg tatgaggctg tgtacgctgt ggcccacggc ctccaccagc   1260
tcctgggatg tacttctgag atctgttcca gaggcccagt ctaccctgg cagcttcttc    1320 agcagatcta caaggtgaat tttcttctac atgagaatac tgtggcattt gatgacaacg   1380
gggacactct aggttactac gacatcatcg cctggggactg gaatggacct gaatggacct   1440
ttgagatcat tggctctgcc tcactgtctc cagttcatct ggacataaat aagacaaaaa   1500
tccagtggca cgggaagaac aatcaggtgc ctgtgtcagt gtgtaccac gactgtctgg   1560 cagggcacca cagggtggtt gtgggttccc accactgctg ctttgagtgt gtgccctgcg  1620
aagctgggac ctttctcaac atgagtgagc ttcacatctg ccagccttgt ggaacagaag   1680
aatgggcacc caaggagagc actacttgct tcccacgcac ggtggagttc ttggcttggc   1740
atgaacccat ctctttggtg ctaatagcag ctaacacgct attgctgctg ctgctggttg   1800
```

```
ggactgctgg cctgtttgcc tggcattttc acacacctgt agtgaggtca gctgggggta   1860
ggctgtgctt cctcatgctg ggttccctgg tggccggaag ttgcagcttc tatagcttct   1920
tcggggagcc cacggtgccc gcgtgcttgc tgcgtcagcc cctcttttct ctcgggtttg   1980
ccatcttcct ctcctgcctg acaatccgct ccttccaact ggtcatcatc ttcaagtttt   2040
ctaccaaggt gcccacattc taccgtacct gggcccaaaa ccatggtgca ggtctattcg   2100
tcattgtcag ctccacggtc catttgctca tctgtctcac atggcttgta atgtggaccc   2160
cacgacccac cagggaatac cagcgcttcc cccatctggt gattctcgag tgcacagagg   2220
tcaactctgt aggcttcctg ttggctttca cccacaacat tctcctctcc atcagtacct   2280
tcgtctgcag ctacctgggt aaggaactgc cagagaacta taatgaagcc aaatgtgtca   2340
ccttcagcct gctcctcaac ttcgtatcct ggatcgcctt cttcaccatg gccagcattt   2400
accagggcag ctacctgcct gcggtcaatg tgctggcagg gctgaccaca ctgagcggcg   2460
gcttcagcgg ttacttcctc cccaagtgct atgtgattct ctgccgtcca gaactcaaca   2520
atacagaaca ctttcaggcc tccatccagg actacgag gcgctgcggc actacctgat   2580
ccactggaaa ggtgcagacg ggaaggaagc ctctcttctt gtgctgaagg tggcgggtcc   2640
agtggggccg agagcttgag gtgtctggga gagctccggc acagcttacg atgtataagc   2700
acgcggaaga atccagtgca ataaagacgg gaagtgtgaa aaaaaaaaa aaaaaaaaa   2760 aaaaaaaaaa a                                                        2771

<210> SEQ ID NO 5
<211> LENGTH: 2579
<212> TYPE: DNA
<213> ORGANISM: Mus musculus
<220> FEATURE:
<223> OTHER INFORMATION: mouse T1R1 sweet taste receptor

<400> SEQUENCE: 5
tttggccagc atgcttttct gggcagctca cctgctgctc agcctgcagc tggccgttgc     60
ttactgctgg gctttcagct gccaaaggac agaatcctct ccaggtttca gcctccctgg    120
ggacttcctc ctggcaggcc tgttctccct ccatgctgac tgtctgcagg tgagacacag    180
acctctggtg acaagttgtg acaggtctga cagcttcaac ggccatggct atcacctctt    240
ccaagccatg cggttcaccg ttgaggagat aaacaactcc acagctctgc ttcccaacat    300
caccctgggg tatgaactgt atgacgtgtg ctcagagtct tccaatgtct atgccaccct    360
gagggtgccc gcccagcaag gacaggcca cctagagatg cagagagatc ttcgcaacca    420
ctcctccaag gtggtggcac tcattgggcc tgataacact gaccacgctg tcaccactgc    480
tgccctgctg agcccttttc tgatgccct ggtcagctat gaggcgagca gcgtgatcct    540
cagtgggaag cgcaagttcc cgtccttctt gcgcaccatc cccagcgata agtaccaggt    600
ggaagtcata gtgcggctgc tgcagagctt cggctgggtc tggatctcgc tcgttggcag    660
ctatggtgac tacgggcagc tgggcgtaca ggcgctggag gagctggcca ctccacgggg    720
catctgcgtc gccttcaagg acgtggtgcc tctctccgcc caggcgggtg acccaaggat    780
gcagcgcatg atgctgcgtc tggctcgagc caggaccacc gtggtcgtgg tcttctctaa    840 ccgcacctg ctggagtgt tcttcaggtc tgtggtgctg ccaacctga ctggcaaagt    900 gtggatcgcc tccgaagact gggccatctc cacgtacatc accaatgtgc ccgggatcca    960
gggcattggg acggtgctgg gggtggcat ccagcagaga caagtccctg gcctgaagga   1020
gtttgaagag tccatgtgcc aggcagtgat gggtgctccc agaacttgcc cagagggtc   1080
```

```
ctggtgcggc actaaccagc tgtgcaggga gtgtcacgct tcacgacat ggaacatgcc    1140 cgagcttgga gccttctcca tgagcgctgc ctacaatgtg tatgaggctg tgtatgctgt    1200
ggcccacggc ctccaccagc tcctgggatg tacctctggg acctgtgcca gaggcccagt    1260 ctaccccotgg cagcttcttc agcagatcta caaggtgaat tccttctac ataagaagac    1320 tgtagcattc gatgacaagg gggaccctct aggttattat gacatcatcg cctgggactg    1380
gaatggacct gaatggacct tgaggtcat tggttctgcc tcactgtctc cagttcatct    1440
agacataaat aagacaaaaa tccagtggca cgggaagaac aatcaggtgc ctgtgtcagt    1500
gtgtaccagg gactgtctcg aagggcacca caggttggtc atgggttccc accactgctg    1560
cttcgagtgc atgcccctgtg aagctgggac atttctcaac acgagtgagc ttcacacctg    1620
ccagccttgt ggaacagaag aatgggcccc tgaggggagc tcagcctgct ctctcacgcac    1680 cgtggagttc ttggggtggc atgaacccat ctctttggtg ctattagcag ctaacacgct    1740
attgctgctg ctgctgattg ggactgctgg cctgtttgcc tggcgtcttc acacgcctgt    1800
tgtgaggtca gctgggggta ggctgtgctt cctcatgctg ggttccttgg tagctgggag    1860
ttgcagcctc tacagcttct tcgggaagcc cacggtgccc gcgtgcttgc tgcgtcagcc    1920 cctctttttct ctcgggttttg ccattttcct ctcctgtctg acaatccgct ccttccaact    1980
ggtcatcatc ttcaagtttt ctaccaaggt acccacattc taccacactt gggcccaaaa    2040
ccatggtgcc ggaatattcg tcattgtcag ctccacggtc catttgttcc tctgtctcac    2100
gtggcttgca atgtggaccc cacgccacac cagggagtac cagcgcttcc cccatctggt    2160
gattcttgag tgcacagagg tcaactctgt gggcttcctg gtggctttcg cacacaacat    2220
cctcctctcc atcagcacct ttgtctgcag ctacctgggt aaggaactgc cggagaacta    2280
taacgaagcc aaatgtgtca ccttcagcct gctcctccac ttcgtatcct ggatcgcttt    2340
cttcaccatg tccagcattt accagggcag ctacctaccc gcggtcaatg tgctggcagg    2400
gctggccact ctgagtggcg gcttcagcgg ctatttcctc cctaaatgct acgtgattct    2460
ctgccgtcca gaactcaaca acacagaaca ctttcaggcc tccatccagg actacacgag    2520
gcgctgcggc actacctgag gcgctgcggc actacctgag gcgctgcggc actacctga    2579

<210> SEQ ID NO 6
<211> LENGTH: 2333
<212> TYPE: DNA
<213> ORGANISM: Homo sapiens
<220> FEATURE:
<223> OTHER INFORMATION: human T1R1 sweet taste receptor

<400> SEQUENCE: 6
aggtcttgta gcttcaatga gcatggctac cacctcttcc aggctatgcg gcttggggtt      60
gaggagataa acaactccac ggccctgctg cccaacatca ccctgggta ccagctgtat     120 gatgtgtgtt ctgactctgc caatgtgtat gccacgctga gagtgctctc cctgccaggg     180
caacaccaca tagagctcca aggagaccctt ctccactatt ccctacggt gctggcagtg     240 attgggcctg acagcaccaa ccgtgctgcc accacagccg ccctgctgag ccctttcctg     300
gtgcatatta gctatgcggc cagcagcgag acgctcagcg tgaagcggca gtatccctct     360
ttcctgcgca ccatccccaa tgacaagtac caggtggaga ccatggtgct gctgctgcag     420
aagttcgggt ggacctggat ctctctggtt ggcagcagtg acgactatgg cagctaggg      480 gtgcaggcac tggagaacca ggccctggtc aggggcatct gcattgcttt caaggacatc     540
atgcccttct ctgcccaggt gggcgatgag aggatgcagt gcctcatgcg ccacctggcc     600
```

```
caggccgggg ccaccgtcgt ggttgttttt tccagccggc agttggccag ggtgtttttc    660
gagtccgtgg tgctgaccaa cctgactggc aaggtgtggg tcgcctcaga agcctgggcc    720
ctctccaggc acatcactgg ggtgcccggg atccagcgca ttgggatggt gctgggcgtg    780
gccatccaga gagggctgt ccctggcctg aaggcgtttg aagaagccta tgcccgggca    840
gacaaggagg cccctaggcc ttgcacaagg gctcctggtg cagcagcaat cagctctgca    900
gagaatgcca agctttcatg gcacacacga tgcccaagct caaagccttc tccatgagtt    960
ctgcctacaa cgcataccgg gctgtgtatg cggtggccca tggcctccac cagctcctgg   1020
gctgtgcctc tgagctctgt tccaggggcc gagtctaccc ctggcagctt ttggagcaga   1080
tccacaaggt gcatttcctt ctacacaagg acactgtggc gtttaatgac aacagagatc   1140
ccctcagtag ctataacata attgcctggg actggaatgg acccaagtgg accttcacgg   1200
tcctcggttc ctccacatgg tctccagttc agctaaacat aaatgagacc aaaatccagt   1260
ggcacggaaa gaaccaccag gtgcctaagt ctgtgtgttc cagcgactgt cttgaagggc   1320
accagcgagt ggttacgggt ttccatcact gctgctttga gtgtgtgccc tgtgggggtg   1380
ggaccttcct caacaagagc gagctctaca gatgccagcc ttgtggaaca aagagtgggg   1440
cacctgaggg aagccagacc tgcttcccgc gcactgtggt gttttggct ttgcgtgagc   1500
acacctcttg ggtgctgctg gcagctaaca cgctgctgct gctgctgctg cttgggactg   1560
ctggcctgtt tgcctggcac ctagacaccc ctgtggtgag gtcagcaggg ggccgcctgt   1620
gctttcttat gctgggctcc ctggcagcag gtagtggcag cctctatggc ttctttgggg   1680
aacccacaag gcctgcgtgc ttgctacgcc aggccctctt tgcccttggt ttcaccatct   1740
tcctgtcctg cctgacagtt cgctcattcc aactaatcat catcttcaag tttcccacca   1800
aggtacctac attctaccac gcctgggtcc aaaaccacgg tgctggcctg tttgtgatga   1860
tcagctcagc ggcccagctg cttatctgtc taacttggct ggtggtgtgg accccactgc   1920
ctgctaggga ataccagcgc ttcccccatc tggtgatgct tgagtgcaca gagaccaact   1980
ccctgggctt catactggcc ttcctctaca tggcctcct ctccatcagt gcctttgcct   2040
gcagctacct gggtaaggac ttgccagaga actacaacga ggccaaatgt gtcaccttca   2100
gcctgctctt caacttcgtg tcctggatcg ccttcttcac cacggccagc gtctacgacg   2160
gcaagtacct gcctgcggcc aacatgatgg ctgggctgag cagcctgagc agcggcttcg   2220
gtgggtattt tctgcctaag tgctacgtga tcctctgccg cccagacctc aacagcacag   2280
agcacttcca ggcctccatt caggactaca cgaggcgctg cggctccacc tga          2333
```

<210> SEQ ID NO 7
<211> LENGTH: 843
<212> TYPE: PRT
<213> ORGANISM: Rattus sp.
<220> FEATURE:
<223> OTHER INFORMATION: rat T1R2 sweet taste receptor

<400> SEQUENCE: 7

```
Met Gly Pro Gln Ala Arg Thr Leu Cys Leu Leu Ser Leu Leu Leu His
 1               5                  10                  15

Val Leu Pro Lys Pro Gly Lys Leu Val Glu Asn Ser Asp Phe His Leu
            20                  25                  30

Ala Gly Asp Tyr Leu Leu Gly Gly Leu Phe Thr Leu His Ala Asn Val
        35                  40                  45

Lys Ser Ile Ser His Leu Ser Tyr Leu Gln Val Pro Lys Cys Asn Glu
    50                  55                  60
```

```
Phe Thr Met Lys Val Leu Gly Tyr Asn Leu Met Gln Ala Met Arg Phe
 65                  70                  75                  80

Ala Val Glu Glu Ile Asn Asn Cys Ser Ser Leu Leu Pro Gly Val Leu
                 85                  90                  95

Leu Gly Tyr Glu Met Val Asp Val Cys Tyr Leu Ser Asn Asn Ile His
            100                 105                 110

Pro Gly Leu Tyr Phe Leu Ala Gln Asp Asp Leu Leu Pro Ile Leu
        115                 120                 125

Lys Asp Tyr Ser Gln Tyr Met Pro His Val Val Ala Val Ile Gly Pro
130                 135                 140

Asp Asn Ser Glu Ser Ala Ile Thr Val Ser Asn Ile Leu Ser His Phe
145                 150                 155                 160

Leu Ile Pro Gln Ile Thr Tyr Ser Ala Ile Ser Asp Lys Leu Arg Asp
                165                 170                 175

Lys Arg His Phe Pro Ser Met Leu Arg Thr Val Pro Ser Ala Thr His
            180                 185                 190

His Ile Glu Ala Met Val Gln Leu Met Val His Phe Gln Trp Asn Trp
        195                 200                 205

Ile Val Val Leu Val Ser Asp Asp Tyr Gly Arg Glu Asn Ser His
    210                 215                 220

Leu Leu Ser Gln Arg Leu Thr Lys Thr Ser Asp Ile Cys Ile Ala Phe
225                 230                 235                 240

Gln Glu Val Leu Pro Ile Pro Glu Ser Ser Gln Val Met Arg Ser Glu
                245                 250                 255

Glu Gln Arg Gln Leu Asp Asn Ile Leu Asp Lys Leu Arg Arg Thr Ser
            260                 265                 270

Ala Arg Val Val Val Phe Ser Pro Glu Leu Ser Leu Tyr Ser Phe
        275                 280                 285

Phe His Glu Val Leu Arg Trp Asn Phe Thr Gly Phe Val Trp Ile Ala
290                 295                 300

Ser Glu Ser Trp Ala Ile Asp Pro Val Leu His Asn Leu Thr Glu Leu
305                 310                 315                 320

Arg His Thr Gly Thr Phe Leu Gly Val Thr Ile Gln Arg Val Ser Ile
                325                 330                 335

Pro Gly Phe Ser Gln Phe Arg Val Arg Arg Asp Lys Pro Gly Tyr Pro
            340                 345                 350

Val Pro Asn Thr Thr Asn Leu Arg Thr Thr Cys Asn Gln Asp Cys Asp
        355                 360                 365

Ala Cys Leu Asn Thr Thr Lys Ser Phe Asn Asn Ile Leu Ile Leu Ser
370                 375                 380

Gly Glu Arg Val Val Tyr Ser Val Tyr Ser Ala Val Tyr Ala Val Ala
385                 390                 395                 400

His Ala Leu His Arg Leu Leu Gly Cys Asn Arg Val Arg Cys Thr Lys
                405                 410                 415

Gln Lys Val Tyr Pro Trp Gln Leu Leu Arg Glu Ile Trp His Val Asn
            420                 425                 430

Phe Thr Leu Leu Gly Asn Arg Leu Phe Phe Asp Gln Gln Gly Asp Met
        435                 440                 445

Pro Met Leu Leu Asp Ile Ile Gln Trp Gln Trp Asp Leu Ser Gln Asn
450                 455                 460

Pro Phe Gln Ser Ile Ala Ser Tyr Ser Pro Thr Ser Lys Arg Leu Thr
465                 470                 475                 480

Tyr Ile Asn Asn Val Ser Trp Tyr Thr Pro Asn Asn Thr Val Pro Val
```

```
                    485                 490                 495
Ser Met Cys Ser Lys Ser Cys Gln Pro Gly Gln Met Lys Lys Ser Val
                500                 505                 510

Gly Leu His Pro Cys Cys Phe Glu Cys Leu Asp Cys Met Pro Gly Thr
            515                 520                 525

Tyr Leu Asn Arg Ser Ala Asp Glu Phe Asn Cys Leu Ser Cys Pro Gly
        530                 535                 540

Ser Met Trp Ser Tyr Lys Asn Asp Ile Thr Cys Phe Gln Arg Arg Pro
545                 550                 555                 560

Thr Phe Leu Glu Trp His Glu Val Pro Thr Ile Val Ala Ile Leu
                565                 570                 575

Ala Ala Leu Gly Phe Phe Ser Thr Leu Ala Ile Leu Phe Ile Phe Trp
            580                 585                 590

Arg His Phe Gln Thr Pro Met Val Arg Ser Ala Gly Gly Pro Met Cys
        595                 600                 605

Phe Leu Met Leu Val Pro Leu Leu Leu Ala Phe Gly Met Val Pro Val
    610                 615                 620

Tyr Val Gly Pro Pro Thr Val Phe Ser Cys Phe Cys Arg Gln Ala Phe
625                 630                 635                 640

Phe Thr Val Cys Phe Ser Ile Cys Leu Ser Cys Ile Thr Val Arg Ser
                645                 650                 655

Phe Gln Ile Val Cys Val Phe Lys Met Ala Arg Arg Leu Pro Ser Ala
            660                 665                 670

Tyr Ser Phe Trp Met Arg Tyr His Gly Pro Tyr Val Phe Val Ala Phe
        675                 680                 685

Ile Thr Ala Ile Lys Val Ala Leu Val Val Gly Asn Met Leu Ala Thr
    690                 695                 700

Thr Ile Asn Pro Ile Gly Arg Thr Asp Pro Asp Asp Pro Asn Ile Met
705                 710                 715                 720

Ile Leu Ser Cys His Pro Asn Tyr Arg Asn Gly Leu Leu Phe Asn Thr
                725                 730                 735

Ser Met Asp Leu Leu Leu Ser Val Leu Gly Phe Ser Phe Ala Tyr Met
            740                 745                 750

Gly Lys Glu Leu Pro Thr Asn Tyr Asn Glu Ala Lys Phe Ile Thr Leu
        755                 760                 765

Ser Met Thr Phe Ser Phe Thr Ser Ser Ile Ser Leu Cys Thr Phe Met
    770                 775                 780

Ser Val His Asp Gly Val Leu Val Thr Ile Met Asp Leu Leu Val Thr
785                 790                 795                 800

Val Leu Asn Phe Leu Ala Ile Gly Leu Gly Tyr Phe Gly Pro Lys Cys
                805                 810                 815

Tyr Met Ile Leu Phe Tyr Pro Glu Arg Asn Thr Ser Ala Tyr Phe Asn
            820                 825                 830

Ser Met Ile Gln Gly Tyr Thr Met Arg Lys Ser
        835                 840

<210> SEQ ID NO 8
<211> LENGTH: 843
<212> TYPE: PRT
<213> ORGANISM: Mus musculus
<220> FEATURE:
<223> OTHER INFORMATION: mouse T1R2 sweet taste receptor

<400> SEQUENCE: 8

Met Gly Pro Gln Ala Arg Thr Leu His Leu Leu Phe Leu Leu Leu His
1               5                   10                  15
```

Ala Leu Pro Lys Pro Val Met Leu Val Gly Asn Ser Asp Phe His Leu
            20                  25                  30

Ala Gly Asp Tyr Leu Leu Gly Gly Leu Phe Thr Leu His Ala Asn Val
        35                  40                  45

Lys Ser Val Ser His Leu Ser Tyr Leu Gln Val Pro Lys Cys Asn Glu
    50                  55                  60

Tyr Asn Met Lys Val Leu Gly Tyr Asn Leu Met Gln Ala Met Arg Phe
65                  70                  75                  80

Ala Val Glu Glu Ile Asn Asn Cys Ser Leu Leu Pro Gly Val Leu
                85                  90                  95

Leu Gly Tyr Glu Met Val Asp Val Cys Tyr Leu Ser Asn Asn Ile Gln
                100                 105                 110

Pro Gly Leu Tyr Phe Leu Ser Gln Ile Asp Asp Phe Leu Pro Ile Leu
            115                 120                 125

Lys Asp Tyr Ser Gln Tyr Arg Pro Gln Val Val Ala Val Ile Gly Pro
    130                 135                 140

Asp Asn Ser Glu Ser Ala Ile Thr Val Ser Asn Ile Leu Ser Tyr Phe
145                 150                 155                 160

Leu Val Pro Gln Val Thr Tyr Ser Ala Ile Thr Asp Lys Leu Gln Asp
                165                 170                 175

Lys Arg Arg Phe Pro Ala Met Leu Arg Thr Val Pro Ser Ala Thr His
            180                 185                 190

His Ile Glu Ala Met Val Gln Leu Met Val His Phe Gln Trp Asn Trp
        195                 200                 205

Ile Val Val Leu Val Ser Asp Asp Tyr Gly Arg Glu Asn Ser His
        210                 215                 220

Leu Leu Ser Gln Arg Leu Thr Asn Thr Gly Asp Ile Cys Ile Ala Phe
225                 230                 235                 240

Gln Glu Val Leu Pro Val Pro Glu Pro Asn Gln Ala Val Arg Pro Glu
                245                 250                 255

Glu Gln Asp Gln Leu Asp Asn Ile Leu Asp Lys Leu Arg Arg Thr Ser
            260                 265                 270

Ala Arg Val Val Val Ile Phe Ser Pro Glu Leu Ser Leu His Asn Phe
    275                 280                 285

Phe Arg Glu Val Leu Arg Trp Asn Phe Thr Gly Phe Val Trp Ile Ala
    290                 295                 300

Ser Glu Ser Trp Ala Ile Asp Pro Val Leu His Asn Leu Thr Glu Leu
305                 310                 315                 320

Arg His Thr Gly Thr Phe Leu Gly Val Thr Ile Gln Arg Val Ser Ile
                325                 330                 335

Pro Gly Phe Ser Gln Phe Arg Val Arg His Asp Lys Pro Gly Tyr Arg
            340                 345                 350

Met Pro Asn Glu Thr Ser Leu Arg Thr Thr Cys Asn Gln Asp Cys Asp
    355                 360                 365

Ala Cys Met Asn Ile Thr Glu Ser Phe Asn Asn Val Leu Met Leu Ser
    370                 375                 380

Gly Glu Arg Val Val Tyr Ser Val Tyr Ser Ala Val Tyr Ala Val Ala
385                 390                 395                 400

His Thr Leu His Arg Leu Leu His Cys Asn Gln Val Arg Cys Thr Lys
                405                 410                 415

Gln Ile Val Tyr Pro Trp Gln Leu Leu Arg Glu Ile Trp His Val Asn
            420                 425                 430

Phe Thr Leu Leu Gly Asn Gln Leu Phe Phe Asp Glu Gln Gly Asp Met

```
                    435                 440                 445
Pro Met Leu Leu Asp Ile Ile Gln Trp Gln Trp Gly Leu Ser Gln Asn
450                 455                 460

Pro Phe Gln Ser Ile Ala Ser Tyr Ser Pro Thr Glu Thr Arg Leu Thr
465                 470                 475                 480

Tyr Ile Ser Asn Val Ser Trp Tyr Thr Pro Asn Asn Thr Val Pro Ile
                485                 490                 495

Ser Met Cys Ser Lys Ser Cys Gln Pro Gly Gln Met Lys Lys Pro Ile
            500                 505                 510

Gly Leu His Pro Cys Cys Phe Glu Cys Val Asp Cys Pro Pro Asp Thr
        515                 520                 525

Tyr Leu Asn Arg Ser Val Asp Glu Phe Asn Cys Leu Ser Cys Pro Gly
    530                 535                 540

Ser Met Trp Ser Tyr Lys Asn Asn Ile Ala Cys Phe Lys Arg Arg Leu
545                 550                 555                 560

Ala Phe Leu Glu Trp His Glu Val Pro Thr Ile Val Thr Ile Leu
                565                 570                 575

Ala Ala Leu Gly Phe Ile Ser Thr Leu Ala Ile Leu Leu Ile Phe Trp
            580                 585                 590

Arg His Phe Gln Thr Pro Met Val Arg Ser Ala Gly Gly Pro Met Cys
        595                 600                 605

Phe Leu Met Leu Val Pro Leu Leu Ala Phe Gly Met Val Pro Val
    610                 615                 620

Tyr Val Gly Pro Pro Thr Val Phe Ser Cys Phe Cys Arg Gln Ala Phe
625                 630                 635                 640

Phe Thr Val Cys Phe Ser Val Cys Leu Ser Cys Ile Thr Val Arg Ser
                645                 650                 655

Phe Gln Ile Val Cys Val Phe Lys Met Ala Arg Arg Leu Pro Ser Ala
            660                 665                 670

Tyr Gly Phe Trp Met Arg Tyr His Gly Pro Tyr Val Phe Val Ala Phe
        675                 680                 685

Ile Thr Ala Val Lys Val Ala Leu Val Ala Gly Asn Met Leu Ala Thr
    690                 695                 700

Thr Ile Asn Pro Ile Gly Arg Thr Asp Pro Asp Pro Asn Ile Ile
705                 710                 715                 720

Ile Leu Ser Cys His Pro Asn Tyr Arg Asn Gly Leu Leu Phe Asn Thr
                725                 730                 735

Ser Met Asp Leu Leu Ser Val Leu Gly Phe Ser Phe Ala Tyr Val
            740                 745                 750

Gly Lys Glu Leu Pro Thr Asn Tyr Asn Glu Ala Lys Phe Ile Thr Leu
        755                 760                 765

Ser Met Thr Phe Ser Phe Thr Ser Ser Ile Ser Leu Cys Thr Phe Met
    770                 775                 780

Ser Val His Asp Gly Val Leu Val Thr Ile Met Asp Leu Leu Val Thr
785                 790                 795                 800

Val Leu Asn Phe Leu Ala Ile Gly Leu Gly Tyr Phe Gly Pro Lys Cys
                805                 810                 815

Tyr Met Ile Leu Phe Tyr Pro Glu Arg Asn Thr Ser Ala Tyr Phe Asn
            820                 825                 830

Ser Met Ile Gln Gly Tyr Thr Met Arg Lys Ser
        835                 840

<210> SEQ ID NO 9
<211> LENGTH: 838
```

```
<212> TYPE: PRT
<213> ORGANISM: Homo sapiens
<220> FEATURE:
<223> OTHER INFORMATION: human T1R2 sweet taste receptor

<400> SEQUENCE: 9
```

| | | | | | | | | | | | | | | |
|---|---|---|---|---|---|---|---|---|---|---|---|---|---|---|
| Met | Gly | Pro | Arg | Ala | Lys | Thr | Ile | Cys | Ser | Leu | Phe | Phe | Leu | Trp |
| 1 | | | | 5 | | | | | 10 | | | | | 15 |
| Val | Leu | Ala | Glu | Pro | Ala | Glu | Asn | Ser | Asp | Phe | Tyr | Leu | Pro | Gly | Asp |
| | | | 20 | | | | | 25 | | | | | 30 | | |
| Tyr | Leu | Leu | Gly | Gly | Leu | Phe | Ser | Leu | His | Ala | Asn | Met | Lys | Gly | Ile |
| | | 35 | | | | | 40 | | | | | 45 | | | |
| Val | His | Leu | Asn | Phe | Leu | Gln | Val | Pro | Met | Cys | Lys | Glu | Tyr | Glu | Val |
| 50 | | | | | 55 | | | | | 60 | | | | | |
| Lys | Val | Ile | Gly | Tyr | Asn | Leu | Met | Gln | Ala | Met | Arg | Phe | Ala | Val | Glu |
| 65 | | | | | 70 | | | | | 75 | | | | | 80 |
| Glu | Ile | Asn | Asn | Asp | Ser | Ser | Leu | Leu | Pro | Gly | Val | Leu | Leu | Gly | Tyr |
| | | | | 85 | | | | | 90 | | | | | 95 | |
| Glu | Ile | Val | Asp | Val | Cys | Tyr | Ile | Ser | Asn | Asn | Val | Gln | Pro | Val | Leu |
| | | | | 100 | | | | | 105 | | | | | 110 | |
| Tyr | Phe | Leu | Ala | His | Glu | Asp | Asn | Leu | Leu | Pro | Ile | Gln | Glu | Asp | Tyr |
| | | | 115 | | | | | 120 | | | | | 125 | | |
| Ser | Asn | Tyr | Ile | Ser | Arg | Val | Val | Ala | Val | Ile | Gly | Pro | Asp | Asn | Ser |
| | 130 | | | | | 135 | | | | | 140 | | | | |
| Glu | Ser | Val | Met | Thr | Val | Ala | Asn | Phe | Leu | Ser | Leu | Phe | Leu | Leu | Pro |
| 145 | | | | | 150 | | | | | 155 | | | | | 160 |
| Gln | Ile | Thr | Tyr | Ser | Ala | Ile | Ser | Asp | Glu | Leu | Arg | Asp | Lys | Val | Arg |
| | | | | 165 | | | | | 170 | | | | | 175 | |
| Phe | Pro | Ala | Leu | Leu | Arg | Thr | Thr | Pro | Ser | Ala | Asp | His | His | Val | Glu |
| | | | 180 | | | | | 185 | | | | | 190 | | |
| Ala | Met | Val | Gln | Leu | Met | Leu | His | Phe | Arg | Trp | Asn | Trp | Ile | Ile | Val |
| | | 195 | | | | | 200 | | | | | 205 | | | |
| Leu | Val | Ser | Ser | Asp | Thr | Tyr | Gly | Arg | Asp | Asn | Gly | Gln | Leu | Leu | Gly |
| | 210 | | | | | 215 | | | | | 220 | | | | |
| Glu | Arg | Val | Ala | Arg | Arg | Asp | Ile | Cys | Ile | Ala | Phe | Gln | Glu | Thr | Leu |
| 225 | | | | | 230 | | | | | 235 | | | | | 240 |
| Pro | Thr | Leu | Gln | Pro | Asn | Gln | Asn | Met | Thr | Ser | Glu | Glu | Arg | Gln | Arg |
| | | | | 245 | | | | | 250 | | | | | 255 | |
| Leu | Val | Thr | Ile | Val | Asp | Lys | Leu | Gln | Gln | Ser | Thr | Ala | Arg | Val | Val |
| | | | 260 | | | | | 265 | | | | | 270 | | |
| Val | Val | Phe | Ser | Pro | Asp | Leu | Thr | Leu | Tyr | His | Phe | Phe | Asn | Glu | Val |
| | | 275 | | | | | 280 | | | | | 285 | | | |
| Leu | Arg | Gln | Asn | Phe | Thr | Gly | Ala | Val | Trp | Ile | Ala | Ser | Glu | Ser | Trp |
| | 290 | | | | | 295 | | | | | 300 | | | | |
| Ala | Ile | Asp | Pro | Val | Leu | His | Asn | Leu | Thr | Glu | Leu | Gly | His | Leu | Gly |
| 305 | | | | | 310 | | | | | 315 | | | | | 320 |
| Thr | Phe | Leu | Gly | Ile | Thr | Ile | Gln | Ser | Val | Pro | Ile | Pro | Gly | Phe | Ser |
| | | | | 325 | | | | | 330 | | | | | 335 | |
| Glu | Phe | Arg | Glu | Trp | Gly | Pro | Gln | Ala | Gly | Pro | Pro | Leu | Ser | Arg |
| | | | 340 | | | | | 345 | | | | | 350 | | |
| Thr | Ser | Gln | Ser | Tyr | Thr | Cys | Asn | Gln | Glu | Cys | Asp | Asn | Cys | Leu | Asn |
| | | | 355 | | | | | 360 | | | | | 365 | | |
| Ala | Thr | Leu | Ser | Phe | Asn | Thr | Ile | Leu | Arg | Leu | Ser | Gly | Glu | Arg | Val |
| | | 370 | | | | | 375 | | | | | 380 | | | |
| Val | Tyr | Ser | Val | Tyr | Ser | Ala | Val | Tyr | Ala | Val | Ala | His | Ala | Leu | His |

```
                385                 390                 395                 400
Ser Leu Leu Gly Cys Asp Lys Ser Thr Cys Thr Lys Arg Val Val Tyr
                    405                 410                 415

Pro Trp Gln Leu Leu Glu Glu Ile Trp Lys Val Asn Phe Thr Leu Leu
            420                 425                 430

Asp His Gln Ile Phe Phe Asp Pro Gln Gly Asp Val Ala Leu His Leu
                435                 440                 445

Glu Ile Val Gln Trp Gln Trp Asp Arg Ser Gln Asn Pro Phe Gln Ser
            450                 455                 460

Val Ala Ser Tyr Tyr Pro Leu Gln Arg Gln Leu Lys Asn Ile Gln Asp
465                 470                 475                 480

Ile Ser Trp His Thr Val Asn Asn Thr Ile Pro Met Ser Met Cys Ser
                485                 490                 495

Lys Arg Cys Gln Ser Gly Gln Lys Lys Lys Pro Val Gly Ile His Val
                500                 505                 510

Cys Cys Phe Glu Cys Ile Asp Cys Leu Pro Gly Thr Phe Leu Asn His
                515                 520                 525

Thr Glu Asp Glu Tyr Glu Cys Gln Ala Cys Pro Asn Asn Glu Trp Ser
            530                 535                 540

Tyr Gln Ser Glu Thr Ser Cys Phe Lys Arg Gln Leu Val Phe Leu Glu
545                 550                 555                 560

Trp His Glu Ala Pro Thr Ile Ala Val Ala Leu Leu Ala Ala Leu Gly
                    565                 570                 575

Phe Leu Ser Thr Leu Ala Ile Leu Val Ile Phe Trp Arg His Phe Gln
            580                 585                 590

Thr Pro Ile Val Arg Ser Ala Gly Gly Pro Met Cys Phe Leu Met Leu
                595                 600                 605

Thr Leu Leu Leu Val Ala Tyr Met Val Val Pro Val Tyr Val Gly Pro
            610                 615                 620

Pro Lys Val Ser Thr Cys Leu Cys Arg Gln Ala Leu Phe Pro Leu Cys
625                 630                 635                 640

Phe Thr Ile Cys Ile Ser Cys Ile Ala Val Arg Ser Phe Gln Ile Val
                    645                 650                 655

Cys Ala Phe Lys Met Ala Ser Arg Phe Pro Arg Ala Tyr Ser Tyr Trp
                660                 665                 670

Val Arg Tyr Gln Gly Pro Tyr Val Ser Met Ala Phe Ile Thr Val Leu
                    675                 680                 685

Lys Met Val Ile Val Val Ile Gly Met Leu Ala Arg Pro Gln Ser His
            690                 695                 700

Pro Arg Thr Asp Pro Asp Asp Pro Lys Ile Thr Ile Val Ser Cys Asn
705                 710                 715                 720

Pro Asn Tyr Arg Asn Ser Leu Leu Phe Asn Thr Ser Leu Asp Leu Leu
                    725                 730                 735

Leu Ser Val Val Gly Phe Ser Phe Ala Tyr Met Gly Lys Glu Leu Pro
                740                 745                 750

Thr Asn Tyr Asn Glu Ala Lys Phe Ile Thr Leu Ser Met Thr Phe Tyr
            755                 760                 765

Phe Thr Ser Ser Val Ser Leu Cys Thr Phe Met Ser Ala Tyr Ser Gly
            770                 775                 780

Val Leu Val Thr Ile Val Asp Leu Leu Val Thr Val Leu Asn Leu Leu
785                 790                 795                 800

Ala Ile Ser Leu Gly Tyr Phe Gly Pro Lys Cys Tyr Met Ile Leu Phe
                    805                 810                 815
```

Tyr Pro Glu Arg Asn Thr Pro Ala Tyr Phe Asn Ser Met Ile Gln Gly
                820                 825                 830

Tyr Thr Met Arg Arg Asp
        835

<210> SEQ ID NO 10
<211> LENGTH: 2993
<212> TYPE: DNA
<213> ORGANISM: Rattus sp.
<220> FEATURE:
<223> OTHER INFORMATION: rat T1R2 sweet taste receptor

<400> SEQUENCE: 10

| | | | | |
|---|---|---|---|---|
| cactttgctg | tcatgggtcc | ccaggcaagg | acactctgct | tgctgtctct | cctgctgcat | 60 |
| gttctgccta | agccaggcaa | gctggtgaga | aactctgact | tccacctggc | cggggactac | 120 |
| ctcctgggtg | gcctctttac | cctccatgcc | aacgtgaaga | gcatctccca | cctcagctac | 180 |
| ctgcaggtgc | ccaagtgcaa | tgagttcacc | atgaaggtgt | tgggctacaa | cctcatgcag | 240 |
| gccatgcgtt | tcgctgtgga | ggagatcaac | aactgtagct | ccctgctacc | cggcgtgctg | 300 |
| ctcggctacg | agatggtgga | tgtctgttac | ctctccaaca | atatccaccc | tgggctctac | 360 |
| ttcctggcac | aggacgacga | cctcctgccc | atcctcaaag | actacagcca | gtacatgccc | 420 |
| cacgtggtgg | ctgtcattgg | ccccgacaac | tctgagtccg | ccattaccgt | gtccaacatt | 480 |
| ctctctcatt | tcctcatccc | acagatcaca | tacagcgcca | tctccgacaa | gctgcgggac | 540 |
| aagcggcact | tccctagcat | gctacgcaca | gtgcccagcg | ccacccacca | catcgaggcc | 600 |
| atggtgcagc | tgatggttca | cttccaatgg | aactggattg | tggtgctggt | gagcgacgac | 660 |
| gattacggcc | gcgagaacag | ccacctgttg | agccagcgtc | tgaccaaaac | gagcgacatc | 720 |
| tgcattgcct | tccaggaggt | tctgcccata | cctgagtcca | ccaggtcat | gaggtccgag | 780 |
| gagcagagac | aactggacaa | catcctggac | aagctgcggc | ggacctcggc | gcgcgtcgtg | 840 |
| gtggtgttct | cgcccgagct | gagcctgtat | agcttctttc | acgaggtgct | ccgctggaac | 900 |
| ttcacgggtt | ttgtgtggat | cgcctctgag | tcctggggcta | tcgacccagt | tctgcataac | 960 |
| ctcacggagc | tgcgccacac | gggtactttt | ctgggcgtca | ccatccagag | ggtgtccatc | 1020 |
| cctggcttca | gtcagttccg | agtgcgccgt | gacaagccag | ggtatcccgt | gcctaacacg | 1080 |
| accaacctgc | ggacgacctg | caaccaggac | tgtgacgcct | gcttgaacac | caccaagtcc | 1140 |
| ttcaacaaca | tccttatact | ttcggggggag | cgcgtggtct | acagcgtgta | ctcggcagtt | 1200 |
| tacgcggtgg | cccatgccct | ccacagactc | tcggctgta | accgggtccg | ctgcaccaag | 1260 |
| caaaaggtct | acccgtggca | gctactcagg | gagatctggc | acgtcaactt | cacgctcctg | 1320 |
| ggtaaccggc | tcttctttga | ccacaaggg | gacatgccga | tgctcttgga | catcatccag | 1380 |
| tggcagtggg | acctgagcca | gaatcccttc | caaagcatcg | cctcctattc | tcccaccagc | 1440 |
| aagaggctaa | cctacattaa | caatgtgtcc | tggtacaccc | ccaacaacac | ggtccctgtc | 1500 |
| tccatgtgtt | ccaagagctg | ccagccaggg | caaatgaaaa | agtctgtggg | cctccacccT | 1560 |
| tgttgcttcg | agtgcttgga | ttgtatgcca | ggcacctacc | tcaaccgctc | agcagatgag | 1620 |
| tttaactgtc | tgtcctgccc | gggttccatg | tggtcctaca | gaacgacat | cacttgcttc | 1680 |
| cagcggcggc | ctaccttcct | ggagtggcac | gaagtgccca | ccatcgtggt | ggccatactg | 1740 |
| gctgccctgg | gcttcttcag | tacactggcc | attcttttca | tcttctggag | acatttccag | 1800 |
| acacccatgg | tgcgctcggc | cggtggcccc | atgtgcttcc | tgatgctcgt | gcccctgctg | 1860 |
| ctggcgtttg | ggatggtgcc | cgtgtatgtg | gggccccca | cggtcttctc | atgcttctgc | 1920 |

| | |
|---|---|
| cgacaggctt tcttcaccgt ctgcttctcc atctgcctat cctgcatcac cgtgcgctcc | 1980 |
| ttccagatcg tgtgtgtctt caagatggcc agacgcctgc caagtgccta cagttttgg | 2040 |
| atgcgttacc acgggcccta tgtcttcgtg gccttcatca cggccatcaa ggtggccctg | 2100 |
| gtggtgggca acatgctggc caccaccatc aaccccattg gccggaccga cccggatgac | 2160 |
| cccaacatca tgatcctctc gtgccaccct aactaccgca acgggctact gttcaacacc | 2220 |
| agcatggact gctgctgtc tgtgctgggt ttcagcttcg cttacatggg caaggagctg | 2280 |
| cccaccaact acaacgaagc caagttcatc actctcagca tgaccttctc cttcacctcc | 2340 |
| tccatctccc tctgcacctt catgtctgtg cacgacggcg tgctggtcac catcatggac | 2400 |
| ctcctggtca ctgtgctcaa cttcctggcc atcggcttgg atactttgg ccccaagtgt | 2460 |
| tacatgatcc ttttctaccc ggagcgcaac acctcagcct atttcaatag catgatccag | 2520 |
| ggctacacca tgaggaagag ctagctccgc ccaccggcct cagcagcaga gccccggcc | 2580 |
| acgttaatgg tgttcctctg ccattctctg cagcgtagct atttttaccc acatagcgct | 2640 |
| taaaatacccc atgatgcact ctcccccgac ccccaagcca tttcactggc caggacctac | 2700 |
| cacccactta tagatgaaac caccaaggcg ccctatgggg ctccaaggat ggcctaccac | 2760 |
| tgccatctgg tggtcacagt gagcacatgc gggccgtggc ccatggctcc cagccagctg | 2820 |
| gtggctagtg gctgtgaggc cagatgtctg tgtatctgag ttcctgggaa gcagagactg | 2880 |
| gggctcctgt gttctaatgg tcagatgggc atcatgggcc cttcattatt gcttacgaat | 2940 |
| aaacttccct ccggtgaaaa aaaaaaaaa aaaaaaaaa aaaaaaaaaa aaa | 2993 |

<210> SEQ ID NO 11
<211> LENGTH: 2532
<212> TYPE: DNA
<213> ORGANISM: Mus musculus
<220> FEATURE:
<223> OTHER INFORMATION: mouse T1R2 sweet taste receptor

<400> SEQUENCE: 11

| | |
|---|---|
| atgggacccc aggcgaggac actccatttg ctgtttctcc tgctgcatgc tctgcctaag | 60 |
| ccagtcatgc tggtagggaa ctccgacttt cacctggctg ggactacct cctgggtggc | 120 |
| ctctttaccc tccatgccaa cgtgaagagt gtctctcacc tcagctacct gcaggtgccc | 180 |
| aagtgcaatg agtacaacat gaaggtgttg ggctacaacc tcatgcaggc catgcgattc | 240 |
| gccgtggagg aaatcaacaa ctgtagctct ttgctgcccg gcgtgctgct cggctacgag | 300 |
| atggtggatg tctgctacct ctccaacaat atccagcctg gctctactt cctgtcacag | 360 |
| atagatgact cctgcccat cctcaaagac tacagccagt acaggcccca agtggtggct | 420 |
| gttattggcc cagacaactc tgagtctgcc atcaccgtgt ccaacattct tcctacttc | 480 |
| ctcgtgccac aggtcacata tagcgccatc accgacaagc tgcaagacaa gcggcgcttc | 540 |
| cctgccatgc tgcgcactgt gccagcgcc acccaccaca tcgaggccat ggtgcaactg | 600 |
| atggttcact tccagtggaa ctggatcgtg gtgctggtga gcgatgacga ttatggccga | 660 |
| gagaacagcc acctgctgag ccagcgtctg accaacactg cgacatctg cattgccttc | 720 |
| caggaggttc tgcccgtacc agaacccaac caggctgtga ggcctgagga gcaggaccaa | 780 |
| ctggacaaca tcctggacaa gctgcggcgg acttcggcgc gtgtggtggt gatattctcg | 840 |
| ccggagctga gcctgcacaa cttcttccgt gaggtgctgc gctggaactt cacgggcttt | 900 |
| gtgtggattg cctctgagtc ctgggccatc gaccctgtc tacacaacct cacagagctg | 960 |
| cgccacacgg gcactttcct gggtgtcacc atccagaggg tgtccatccc tggcttcagc | 1020 |

-continued

| | |
|---|---|
| cagttccgag tgcgccatga caagccaggg tatcgcatgc ctaacgagac cagcctgcgg | 1080 |
| actacctgta accaggactg cgacgcctgc atgaacatca ctgagtcctt caacaacgtt | 1140 |
| ctcatgcttt cgggggagcg tgtggtctac agcgtgtact cggccgtcta cgcggtggcc | 1200 |
| cacaccctcc acagactcct ccactgcaat caggtccgct gcaccaagca aatcgtctat | 1260 |
| ccatggcagc tactcaggga gatctggcat gtcaacttca cgctcctggg caaccagctc | 1320 |
| ttcttcgacg aacaagggga catgccgatg ctcctggaca tcatccagtg gcagtggggc | 1380 |
| ctgagccaga ccccttcca aagcatcgcc tcctactccc ccaccgagac gaggctgacc | 1440 |
| tacattagca atgtgtcctg gtacacccc aacaacacgg tccccatatc catgtgttct | 1500 |
| aagagttgcc agcctgggca aatgaaaaaa cccataggcc tccacccatg ctgcttcgag | 1560 |
| tgtgtggact gtccgccgga cacctacctc aaccgatcag tagatgagtt taactgtctg | 1620 |
| tcctgcccgg gttccatgtg gtcttacaag aacaacatcg cttgcttcaa gcggcggctg | 1680 |
| gccttcctgg agtggcacga agtgcccact atcgtggtga ccatcctggc cgccctgggc | 1740 |
| ttcatcagta cgctggccat tctgctcatc ttctggagac atttccagac gcccatggtg | 1800 |
| cgctcggcgg gcggcccat gtgcttcctg atgctggtgc cctgctgct ggcgttcggg | 1860 |
| atggtccccg tgtatgtggg cccccccacg gtcttctcct gtttctgccg ccaggctttc | 1920 |
| ttcaccgttt gcttctccgt ctgcctctcc tgcatcacgg tgcgtccctt ccagattgtg | 1980 |
| tgcgtcttca agatggccag acgcctgcca agcgcctacg gtttctggat gcgttaccac | 2040 |
| gggcccacg tcttcgtggc cttcatcacg gccgtcaagg tggccctggt ggcgggcaac | 2100 |
| atgctggcca ccaccatcaa ccccattggc cggaccgacc ccgatgaccc caatatcata | 2160 |
| atcctctcct gccaccctaa ctaccgcaac gggctactct tcaacaccag catggacttg | 2220 |
| ctgctgtccg tgctgggttt cagcttcgcg tacgtgggca aggaactgcc caccaactac | 2280 |
| aacgaagcca agttcatcac cctcagcatg accttctcct tcacctcctc catctccctc | 2340 |
| tgcacgttca tgtctgtcca cgatggcgtg ctggtcacca tcatggatct cctggtcact | 2400 |
| gtgctcaact ttctggccat cggcttgggg tactttggcc ccaaatgtta catgatcctt | 2460 |
| ttctaccgg agcgcaacac ttcagcttat ttcaatagca tgattcaggg ctacacgatg | 2520 |
| aggaagagct ag | 2532 |

<210> SEQ ID NO 12
<211> LENGTH: 2010
<212> TYPE: DNA
<213> ORGANISM: Homo sapiens
<220> FEATURE:
<223> OTHER INFORMATION: human T1R2 sweet taste receptor

<400> SEQUENCE: 12

| | |
|---|---|
| atcacctaca gcgccatcag cgatgagctg cgagacaagg tgcgcttccc ggctttgctg | 60 |
| cgtaccacac ccagcgccga ccaccacgtc gaggccatgg tgcagctgat gctgcacttc | 120 |
| cgctggaact ggatcattgt gctggtgagc agcgacacct atggccgcga caatggccag | 180 |
| ctgcttggcg agcgcgtggc ccggcgcgac atctgcatcg ccttccagga gacgctgccc | 240 |
| acactgcagc ccaaccagaa catgacgtca gaggagcgcc agcgcctggt gaccattgtg | 300 |
| gacaagctgc agcagagcac agcgcgcgtc gtggtcgtgt tctcgcccga cctgaccctg | 360 |
| taccacttct tcaatgaggt gctgcgccag aacttcacgg gcgccgtgtg gatcgcctcc | 420 |
| gagtcctggg ccatcgaccc ggtcctgcac aacctcacgg agctgggcca cttgggcacc | 480 |
| ttcctgggca tcaccatcca gagcgtgccc atcccgggct tcagtgagtt ccgcgagtgg | 540 |

```
ggcccacagg ctgggccgcc acccctcagc aggaccagcc agagctatac ctgcaaccag    600
gagtgcgaca actgcctgaa cgccaccttg tccttcaaca ccattctcag gctctctggg    660
gagcgtgtcg tctacagcgt gtactctgcg gtctatgctg tggcccatgc cctgcacagc    720
ctcctcggct gtgacaaaag cacctgcacc aagagggtgg tctacccctg gcagctgctt    780
gaggagatct ggaaggtcaa cttcactctc ctggaccacc aaatcttctt cgacccgcaa    840
ggggacgtgg ctctgcactt ggagattgtc agtggcaat gggaccggag ccagaatccc    900
ttccagagcg tcgcctccta ctacccctg cagcgacagc tgaagaacat caagacatct    960
ctgcacaccg tcaacaacac gatccctatg tccatgtgtt ccaagaggtg ccagtcaggg   1020
caaaagaaga agcctgtggg catccacgtc tgctgcttcg agtgcatcga ctgccttccc   1080
ggcaccttcc tcaaccacac tgaatgcccg aataacgagt ggtcctacca gagtgagacc   1140
tcctgcttca gcggcagct ggtcttcctg gaatggcatg aggcacccac catcgctgtg   1200
gccctgctgg ccgccctggg cttcctcagc accctggcca tcctggtgat attctggagg   1260
cacttccaga cacccatagt tcgctcggct gggggcccca tgtgcttcct gatgctgaca   1320
ctgctgctgg tggcatacat ggtggtcccg gtgtacgtgg ggccgcccaa ggtctccacc   1380
tgcctctgcc gccaggccct cttttcccctc tgcttcacaa tttgcatctc ctgtatcgcc   1440
gtgcgttctt tccagatcgt ctgcgccttc aagatggcca gccgcttccc acgcgcctac   1500
agctactggg tccgctacca ggggccctac gtctctatgg catttatcac ggtactcaaa   1560
atggtcattg tggtaattgg catgctggca cggcctcagt cccacccccg tactgacccc   1620
gatgaccca agatcacaat tgtctcctgt aaccccaact accgcaacag cctgctgttc   1680
aacaccagcc tggacctgct gctctcagtg gtgggtttca gcttcgccta catgggcaaa   1740
gagctgccca ccaactacaa cgaggccaag ttcatcaccc tcagcatgac cttctatttc   1800
acctcatccg tctccctctg caccttcatg tctgcctaca gcggggtgct ggtcaccatc   1860
gtggacctct tggtcactgt gctcaacctc ctggccatca gcctgggcta cttcggcccc   1920
aagtgctaca tgatcctctt ctaccccgag cgcaacacgc ccgcctactt caacagcatg   1980
atccagggct acaccatgag gagggactag                                    2010

<210> SEQ ID NO 13
<211> LENGTH: 3200
<212> TYPE: DNA
<213> ORGANISM: Homo sapiens
<220> FEATURE:
<223> OTHER INFORMATION: human T1R3 sweet taste receptor genomic

<400> SEQUENCE: 13
gctcactcca tgtgaggccc cagtcggggc agccacctgc cgtgcctgtt ggaagttgcc     60
tctgccatgc tgggccctgc tgtcctgggc ctcagcctct gggctctcct gcaccctggg    120
acggggccc cattgtgcct gtcacagcaa cttaggatga aggggactca cgtgctgggg    180
gggctgttcc ccctgggcga ggccgaggag gctggcctcc gcagccggac acggcccagc    240
agccctgtgt gcaccaggta cagaggtggg acggcctggg tcgggtcag ggtgaccagg    300
tctggggtgc tcctgagctg gggccgaggt ggccatctgc ggttctgtgt ggccccaggt    360
tctcctcaaa cggcctgctc tgggcactgg ccatgaaaat ggccgtggag gagatcaaca    420
acaagtcgga tctgctgccc gggctgcgcc tgggctacga cctctttgat acgtgctcgg    480
agcctgtggt ggccatgaag cccagcctca tgttcctggc caaggcaggc agccgcgaca    540
tcgccgccta ctgcaactac acgcagtacc agccccgtgt gctggctgtc atcgggccc    600
```

```
actcgtcaga gctcgccatg gtcaccggca agttcttcag cttcttcctc atgccccagg      660
tggcgccccc caccatcacc caccccacc cagccctgcc cgtgggagcc cctgtgtcag        720
gagatgcctc ttggcccttg caggtcagct acggtgctag catggagctg ctgagcgccc      780
gggagacctt cccctccttc ttccgcaccg tgcccagcga ccgtgtgcag ctgacggccg      840
ccgcggagct gctgcaggag ttcggctgga actgggtggc cgccctgggc agcgacgacg      900
agtacggccg gcagggcctg agcatcttct cggccctggc cgcggcacgc ggcatctgca      960
tcgcgcacga gggcctggtg ccgctgcccc gtgccgatga ctcgcggctg ggaaggtgc      1020
aggacgtcct gcaccaggtg aaccagcaga gcgtgcaggt ggtgctgctg ttcgcctccg     1080
tgcacgccgc ccacgccctc ttcaactaca gcatcagcag caggctctcg cccaaggtgt     1140
gggtggccag cgaggcctgg ctgacctctg acctggtcat ggggctgccc ggcatggccc     1200
agatgggcac ggtgcttggc ttcctccaga ggggtgccca gctgcacgag ttcccccagt     1260
acgtgaagac gcacctggcc ctggccaccg acccggcctt ctgctctgcc ctgggcgaga     1320
gggagcaggg tctgaggag acgtggtgg gccagcgctg cccgcagtgt gactgcatca       1380
cgctgcagaa cgtgagcgca gggctaaatc accaccagac gttctctgtc tacgcagctg     1440
tgtatagcgt ggcccaggcc ctgcacaaca ctcttcagtg caacgcctca ggctgccccg     1500
cgcaggaccc cgtgaagccc tggcaggtga gcccggaga tgggggtgtg ctgtcctctg      1560
catgtgccca ggccaccagg cacggccacc acgcctgagc tggaggtggc tggcggctca     1620
gccccgtccc ccgcccgcag ctcctggaga acatgtacaa cctgaccttc cacgtgggcg     1680
ggctgccgct gcggttcgac agcagcggaa acgtggacat ggagtacgac ctgaagctgt     1740
gggtgtggca gggctcagtg cccaggctcc acgacgtggg caggttcaac ggcagcctca    1800
ggacagagcg cctgaagatc cgctggcaca cgtctgacaa ccaggtgagg tgagggtggg    1860
tgtgccaggc gtgcccgtgg tagccccgc ggcaggcgc agcctggggg tgggggccgt       1920
tccagtctcc cgtgggcatg cccagccgag cagagccaga ccccaggcct gtgcgcagaa    1980
gcccgtgtcc cggtgctcgc ggcagtgcca ggagggccag gtgcgccggg tcaagggggtt   2040
ccactcctgc tgctacgact gtgtggactg cgaggcggg agctaccggc aaaacccagg      2100
tgagccgcct tcccggcagg cgggggtggg aacgcagcag gggagggtcc tgccaagtcc    2160
tgactctgag accagagccc acagggtaca agacgaacac ccagcgccct tctcctctct    2220
cacagacgac atcgcctgca ccttttgtgg ccaggatgag tggtccccgg agcgaagcac    2280
acgctgcttc cgccgcaggt ctcggttcct ggcatgggc gagccggctg tgctgctgct     2340
gctcctgctg ctgagcctgg cgctgggcct tgtgctggct gctttggggc tgttcgttca    2400
ccatcgggac agcccactgg ttcaggcctc gggggggccc ctggcctgct ttggcctggt    2460
gtgcctgggc ctggtctgcc tcagcgtcct cctgttccct ggccagccca gccctgcccg    2520
atgcctggcc cagcagccct gtcccacct cccgctcacg ggctgcctga gcacactctt     2580
cctgcaggcg gccgagatct tcgtggagtc agaactgcct ctgagctggg cagaccggct    2640
gagtggctgc ctgcggggc cctgggcctg gctggtggtg ctgctggcca tgctggtgga    2700
ggtcgcactg tgcacctggt acctggtggc cttcccgccg gaggtggtga cggactggca   2760
catgctgccc acgaggcgc tggtgcactg ccgcacacgc tcctgggtca gcttcggcct    2820
agcgcacgcc accaatgcca cgctggcctt tctctgcttc ctgggcactt tcctggtgcg    2880
gagccagccg ggctgctaca accgtgcccg tggcctcacc tttgccatgc tggcctactt   2940
catcacctgg gtctcctttg tgcccctcct ggccaatgtg caggtggtcc tcaggcccgc   3000
```

| | |
|---|---:|
| cgtgcagatg ggcgccctcc tgctctgtgt cctgggcatc ctggctgcct tccacctgcc | 3060 |
| caggtgttac ctgctcatgc ggcagccagg gctcaacacc cccgagttct tcctgggagg | 3120 |
| gggccctggg gatgcccaag gccagaatga cgggaacaca ggaaatcagg ggaaacatga | 3180 |
| gtgacccaac cctgtgatct | 3200 |

```
<210> SEQ ID NO 14
<211> LENGTH: 2559
<212> TYPE: DNA
<213> ORGANISM: Homo sapiens
<220> FEATURE:
<223> OTHER INFORMATION: human T1R3 sweet taste receptor CDS

<400> SEQUENCE: 14
```

| | |
|---|---:|
| atgctgggcc tgctgtcct gggcctcagc ctctgggctc tcctgcaccc tgggacgggg | 60 |
| gccccattgt gcctgtcaca gcaacttagg atgaaggggg actacgtgct gggggggctg | 120 |
| ttcccctgg gcgaggccga ggaggctggc ctccgcagcc ggacacggcc cagcagccct | 180 |
| gtgtgcacca ggttctcctc aaacggcctg ctctgggcac tggccatgaa aatggccgtg | 240 |
| gaggagatca caacaagtc ggatctgctg cccgggctgc gcctgggcta cgacctcttt | 300 |
| gatacgtgct cggagcctgt ggtggccatg aagcccagcc tcatgttcct ggccaaggca | 360 |
| ggcagccgcg acatcgccgc ctactgcaac tacacgcagt accagcccg tgtgctggct | 420 |
| gtcatcgggc cccactcgtc agagctcgcc atggtcaccg gcaagttctt cagcttcttc | 480 |
| ctcatgcccc aggtcagcta cggtgctagc atggagctgc tgagcgcccg ggagaccttc | 540 |
| ccctccttct tccgcaccgt gcccagcgac cgtgtgcagc tgacggccgc cgcggagctg | 600 |
| ctgcaggagt tcggctggaa ctgggtggcc gccctgggca gcgacgacga gtacggccgg | 660 |
| cagggcctga gcatcttctc ggccctggcc gcggcacgcg gcatctgcat cgcgcacgag | 720 |
| ggcctggtgc cgctgccccg tgccgatgac tcgcggctgg ggaaggtgca ggacgtcctg | 780 |
| caccaggtga accagagcag cgtgcaggtg gtgctgctgt tcgcctccgt gcacgccgcc | 840 |
| cacgccctct tcaactacag catcagcagc aggctctcgc ccaaggtgtg ggtggccagc | 900 |
| gaggcctggc tgacctctga cctggtcatg gggctgccg catggccca gatgggcacg | 960 |
| gtgcttggct cctccagag gggtgcccag ctgcacgagt tcccccagta cgtgaagacg | 1020 |
| cacctggccc tggccaccga cccggccttc tgctctgccc tgggcgagag ggagcagggt | 1080 |
| ctggaggagg acgtggtggg ccagcgctgc ccgcagtgtg actgcatcac gctgcagaac | 1140 |
| gtgagcgcag gctaaaatca ccaccagacg ttctctgtct acgcagctgt gtatagcgtg | 1200 |
| gcccaggccc tgcacaacac tcttcagtgc aacgcctcag gctgccccgc gcaggacccc | 1260 |
| gtgaagccct ggcagctcct ggagaacatg tacaacctga ccttccacgt gggcgggctg | 1320 |
| ccgctgcggt tcgacagcag cggaaacgtg gacatggagt acgacctgaa gctgtgggtg | 1380 |
| tggcagggct cagtgcccag gctccacgac gtgggcaggt tcaacggcag cctcaggaca | 1440 |
| gagcgcctga agatccgctg gcacacgtct gacaaccaga agcccgtgtc ccggtgctcg | 1500 |
| cggcagtgcc aggaggggca ggtgcgccgg gtcaagggg tccactcctg ctgctacgac | 1560 |
| tgtgtggact gcgaggcggg cagctaccgg caaaacccag acgacatcgc ctgcaccttt | 1620 |
| tgtggccagg atgagtggtc cccggagcga agcacacgct gcttccgccg caggtctcgg | 1680 |
| ttcctggcat ggggcgagcc ggctgtgctg ctgctgctcc tgctgctgag cctggcgctg | 1740 |
| ggccttgtgc tggctgcttt ggggctgttc gttcaccatc gggacagccc actggttcag | 1800 |
| gcctcggggg ggcccctggc ctgctttggc ctggtgtgcc tgggcctggt ctgcctcagc | 1860 |

-continued

```
gtcctcctgt tccctggcca gcccagcccct gcccgatgcc tggcccagca gcccttgtcc   1920
cacctcccgc tcacgggctg cctgagcaca ctcttcctgc aggcggccga gatcttcgtg   1980
gagtcagaac tgcctctgag ctgggcagac cggctgagtg gctgctgcg ggggccctgg   2040 gcctggctgg tggtgctgct ggccatgctg gtggaggtcg cactgtgcac ctggtacctg   2100
gtggccttcc cgccggaggt ggtgacggac tggcacatgc tgcccacgga ggcgctggtg   2160
cactgccgca cacgctcctg ggtcagcttc ggcctagcgc acgccaccaa tgccacgctg   2220
gcctttctct gcttcctggg cactttcctg gtgcggagcc agccgggctg ctacaaccgt   2280
gcccgtggcc tcacctttgc catgctggcc tacttcatca cctgggtctc ctttgtgccc   2340
ctcctggcca atgtgcaggt ggtcctcagg cccgccgtgc agatgggcgc cctcctgctc   2400
tgtgtcctgg gcatcctggc tgccttccac ctgcccaggt gttacctgct catgcggcag   2460
ccagggctca acaccccccga gttcttcctg ggaggggggcc ctgggatgc ccaaggccag   2520 aatgacggga acacaggaaa tcagggggaaa catgagtga                          2559
```

<210> SEQ ID NO 15
<211> LENGTH: 852
<212> TYPE: PRT
<213> ORGANISM: Homo sapiens
<220> FEATURE:
<223> OTHER INFORMATION: human T1R3 sweet taste receptor

<400> SEQUENCE: 15

```
Met Leu Gly Pro Ala Val Leu Gly Leu Ser Leu Trp Ala Leu Leu His
 1               5                  10                  15

Pro Gly Thr Gly Ala Pro Leu Cys Leu Ser Gln Gln Leu Arg Met Lys
             20                  25                  30

Gly Asp Tyr Val Leu Gly Gly Leu Phe Pro Leu Gly Glu Ala Glu Glu
         35                  40                  45

Ala Gly Leu Arg Ser Arg Thr Arg Pro Ser Ser Pro Val Cys Thr Arg
     50                  55                  60

Phe Ser Ser Asn Gly Leu Leu Trp Ala Leu Ala Met Lys Met Ala Val
 65                  70                  75                  80

Glu Glu Ile Asn Asn Lys Ser Asp Leu Leu Pro Gly Leu Arg Leu Gly
                 85                  90                  95

Tyr Asp Leu Phe Asp Thr Cys Ser Glu Pro Val Val Ala Met Lys Pro
            100                 105                 110

Ser Leu Met Phe Leu Ala Lys Ala Gly Ser Arg Asp Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Met Val Thr Gly Lys Phe Phe Ser Phe Phe
145                 150                 155                 160

Leu Met Pro Gln Val Ser Tyr Gly Ala Ser Met Glu Leu Leu Ser Ala
                165                 170                 175

Arg Glu Thr Phe Pro Ser Phe Phe Arg Thr Val Pro Ser Asp Arg Val
            180                 185                 190

Gln Leu Thr Ala Ala Ala Glu Leu Leu Gln Glu Phe Gly Trp Asn Trp
        195                 200                 205

Val Ala Ala Leu Gly Ser Asp Asp Glu Tyr Gly Arg Gln Gly Leu Ser
    210                 215                 220

Ile Phe Ser Ala Leu Ala Ala Ala Arg Gly Ile Cys Ile Ala His Glu
225                 230                 235                 240

Gly Leu Val Pro Leu Pro Arg Ala Asp Asp Ser Arg Leu Gly Lys Val
```

```
                    245                 250                 255
Gln Asp Val Leu His Gln Val Asn Gln Ser Ser Val Gln Val Val Leu
                260                 265                 270

Leu Phe Ala Ser Val His Ala Ala His Ala Leu Phe Asn Tyr Ser Ile
            275                 280                 285

Ser Ser Arg Leu Ser Pro Lys Val Trp Val Ala Ser Glu Ala Trp Leu
        290                 295                 300

Thr Ser Asp Leu Val Met Gly Leu Pro Gly Met Ala Gln Met Gly Thr
305                 310                 315                 320

Val Leu Gly Phe Leu Gln Arg Gly Ala Gln Leu His Glu Phe Pro Gln
                325                 330                 335

Tyr Val Lys Thr His Leu Ala Leu Ala Thr Asp Pro Ala Phe Cys Ser
            340                 345                 350

Ala Leu Gly Glu Arg Glu Gln Gly Leu Glu Glu Asp Val Val Gly Gln
        355                 360                 365

Arg Cys Pro Gln Cys Asp Cys Ile Thr Leu Gln Asn Val Ser Ala Gly
370                 375                 380

Leu Asn His His Gln Thr Phe Ser Val Tyr Ala Ala Val Tyr Ser Val
385                 390                 395                 400

Ala Gln Ala Leu His Asn Thr Leu Gln Cys Asn Ala Ser Gly Cys Pro
                405                 410                 415

Ala Gln Asp Pro Val Lys Pro Trp Gln Leu Leu Glu Asn Met Tyr Asn
            420                 425                 430

Leu Thr Phe His Val Gly Gly Leu Pro Leu Arg Phe Asp Ser Ser Gly
        435                 440                 445

Asn Val Asp Met Glu Tyr Asp Leu Lys Leu Trp Val Trp Gln Gly Ser
    450                 455                 460

Val Pro Arg Leu His Asp Val Gly Arg Phe Asn Gly Ser Leu Arg Thr
465                 470                 475                 480

Glu Arg Leu Lys Ile Arg Trp His Thr Ser Asp Asn Gln Lys Pro Val
                485                 490                 495

Ser Arg Cys Ser Arg Gln Cys Gln Glu Gly Gln Val Arg Arg Val Lys
            500                 505                 510

Gly Phe His Ser Cys Cys Tyr Asp Cys Val Asp Cys Glu Ala Gly Ser
        515                 520                 525

Tyr Arg Gln Asn Pro Asp Asp Ile Ala Cys Thr Phe Cys Gly Gln Asp
    530                 535                 540

Glu Trp Ser Pro Glu Arg Ser Thr Arg Cys Phe Arg Arg Arg Ser Arg
545                 550                 555                 560

Phe Leu Ala Trp Gly Glu Pro Ala Val Leu Leu Leu Leu Leu Leu Leu
                565                 570                 575

Ser Leu Ala Leu Gly Leu Val Leu Ala Ala Leu Gly Leu Phe Val His
            580                 585                 590

His Arg Asp Ser Pro Leu Val Gln Ala Ser Gly Gly Pro Leu Ala Cys
        595                 600                 605

Phe Gly Leu Val Cys Leu Gly Leu Val Cys Leu Ser Val Leu Leu Phe
    610                 615                 620

Pro Gly Gln Pro Ser Pro Ala Arg Cys Leu Ala Gln Pro Leu Ser
625                 630                 635                 640

His Leu Pro Leu Thr Gly Cys Leu Ser Thr Leu Phe Leu Gln Ala Ala
                645                 650                 655

Glu Ile Phe Val Glu Ser Glu Leu Pro Leu Ser Trp Ala Asp Arg Leu
            660                 665                 670
```

```
Ser Gly Cys Leu Arg Gly Pro Trp Ala Trp Leu Val Val Leu Leu Ala
    675                 680                 685
Met Leu Val Glu Val Ala Leu Cys Thr Trp Tyr Leu Val Ala Phe Pro
    690                 695                 700
Pro Glu Val Val Thr Asp Trp His Met Leu Pro Thr Glu Ala Leu Val
705                 710                 715                 720
His Cys Arg Thr Arg Ser Trp Val Ser Phe Gly Leu Ala His Ala Thr
                725                 730                 735
Asn Ala Thr Leu Ala Phe Leu Cys Phe Leu Gly Thr Phe Leu Val Arg
            740                 745                 750
Ser Gln Pro Gly Cys Tyr Asn Arg Ala Arg Gly Leu Thr Phe Ala Met
            755                 760                 765
Leu Ala Tyr Phe Ile Thr Trp Val Ser Phe Val Pro Leu Leu Ala Asn
    770                 775                 780
Val Gln Val Val Leu Arg Pro Ala Val Gln Met Gly Ala Leu Leu Leu
785                 790                 795                 800
Cys Val Leu Gly Ile Leu Ala Ala Phe His Leu Pro Arg Cys Tyr Leu
                805                 810                 815
Leu Met Arg Gln Pro Gly Leu Asn Thr Pro Glu Phe Phe Leu Gly Gly
            820                 825                 830
Gly Pro Gly Asp Ala Gln Gly Gln Asn Asp Gly Asn Thr Gly Asn Gln
            835                 840                 845
Gly Lys His Glu
    850

<210> SEQ ID NO 16
<211> LENGTH: 3240
<212> TYPE: DNA
<213> ORGANISM: Mus musculus
<220> FEATURE:
<223> OTHER INFORMATION: mouse Sac non taster 129 T1R3 sweet taste
      receptor genomic

<400> SEQUENCE: 16
acatctgtgg ctccaacccc acacacccat ctattgttag tgctggagac ttctacctac     60
catgccagct ttggctatca tgggtctcag cctggctgct ttcctggagc ttgggatggg    120
ggcctctttg tgtctgtcac agcaattcaa ggcacaaggg gactacatac tgggcgggct    180
atttcccctg ggctcgaccg aggaggccac tctcaaccag agagcacaac ccaacagcac    240
cctgtgtaac aggtatggag ctagtagctg gggtgggagt gaaccgaagc ttggcagctt    300
tggctccgtg gtactaccaa tctggggaag gggtggtgat cagtttccat gtggcctcag    360
gttctcaccc ctcggtttgt tcctggccat ggctatgaag atggctgtgg aggagatcaa    420
caatggatct gccttgctcc ctgggctgcg gctgggctat gaccttattt gacacatgct    480
ccgagccagt ggtcaccatg aaatccagtc tcatgttcct ggccaaggtg ggcagtcaaa    540
gcattgctgc ctactgcaac tacacacagt accaaccccg tgtgctggct gtcatcggcc    600
cccactcatc agagcttgcc ctcattacag gcaagttctt cagcttcttc ctcatgccac    660
aggtgagccc acttcctttg tgttctcaac cgattgcacc cattgagctc tcacatcaga    720
aagtgcttct tgatcaccac aggtcagcta tagcgccagc atggatcggc taagtgaccg    780
ggaaacgttt ccatccttct tccgcacagt gcccagtgac cgggtgcagc tgcaggcagt    840
tgtgactctg ttgcagaact tcagctggaa ctgggtggcc gccttaggga gtgatgatga    900
ctatggccgg gaaggtctga gcatcttttc tagtctggcc aatgcacgag gtatctgcat    960
cgcacatgag ggcctggtgc acaacatgac cactagtggc caacagttgg gcaaggtgct   1020
```

```
ggatgtgcta cgccaagtga accaaagtaa agtacaagtg gtggtgctgt ttgcctctgc    1080
ccgtgctgtc tactcccttt ttagttacag catccatcat ggcctctcac ccaaggtatg    1140
ggtggccagt gagtcttggc tgacatctga cctggtcatg acacttccca atattgcccg    1200
tgtgggcact gtgcttgggt ttttgcagcg gggtgcccta ctgcctgaat tttcccatta    1260
tgtggagact caccttgccc tggccgctga cccagcattc tgtgcctcac tgaatgcgga    1320
gttggatctg gaggaacatg tgatggggca acgctgtcca cagtgtgacg acatcatgct    1380
gcagaaccta tcatctgggc tgttgcagaa cctatcagct gggcaattgc accaccaaat    1440
atttgcaacc tatgcagctg tgtacagtgt ggctcaagcc cttcacaaca ccctacagtg    1500
caatgtctca cattgccacg tatcagaaca tgttctaccc tggcaggtaa gggtagggtt    1560
ttttgctggg ttttgcctgc tcctgcagga acactgaacc aggcagagcc aaatcatgtt    1620
gtgactggag aggccttacc ctgactccac tccacagctc ctggagaaca tgtacaatat    1680
gagtttccat gctcgagact tgacactaca gtttgatgct gaagggaatg tagacatgga    1740
atatgacctg aagatgtggg tgtggcagag ccctacacct gtattacata ctgtgggcac    1800
cttcaacggc acccttcagc tgcagcagtc taaaatgtac tggccaggca accaggtaag    1860
gacaagacag gcaaaaagga tggtgggtag aagcttgtcg gtcttgggcc agtgctagcc    1920
aaggggaggc ctaacccaag gctccatgtc caggtgccag tctcccagtg ttcccgccag    1980
tgcaaagatg gccaggttcg ccgagtaaag gctttcatt cctgctgcta tgactgcgtg    2040
gactgcaagg cgggcagcta ccggaagcat ccaggtgaac cgtcttccct agacagtctg    2100
cacagccggg ctagggggca gaagcattca agtctggcaa gcgccctccc gcggggctaa    2160
tgtggagaca gttactgtgg gggctggctg gggaggtcgg tctcccatca gcagacccca    2220
cattactttt cttccttcca tcactacaga tgacttcacc tgtactccat gtaaccagga    2280
ccagtggtcc ccagagaaaa gcacagcctg cttacctcgc aggcccaagt ttctggcttg    2340
gggggagcca gttgtgctgt cactcctcct gctgctttgc ctggtgctgg gtctagcact    2400
ggctgctctg gggctctctg tccaccactg ggacagccct cttgtccagg cctcaggcgg    2460
ctcacagttc tgctttggcc tgatctgcct aggcctcttc tgcctcagtg tccttctgtt    2520
cccaggacgg ccaagctctg ccagctgcct tgcacaacaa ccaatggctc acctccctct    2580
cacaggctgc ctgagcacac tcttcctgca agcagctgag acctttgtgg agtctgagct    2640
gccactgagc tgggcaaact ggctatgcag ctaccttcgg ggactctggg cctggctagt    2700
ggtactgttg gccacttttg tggaggcagc actatgtgcc tggtatttga ccgctttccc    2760
accagaggtg gtgacagact ggtcagtgct gcccacagag gtactggagc actgccacgt    2820
gcgttcctgg gtcagcctgg gcttggtgca catcaccaat gcaatgttag cttttcctctg    2880 ctttctgggc actttcctgg tacagagcca gcctggccgc tacaaccgtg cccgtggtct    2940
caccttcgcc atgctagctt atttcatcac ctgggtctct tttgtgcccc tcctggccaa    3000
tgtgcaggtg gcctaccagc cagctgtgca gatgggtgct atcctagtct gtgccctggg    3060
catcctggtc accttccacc tgcccaagtg ctatgtgctt ctttggctgc caaagctcaa    3120
cacccaggag ttcttcctgg gaaggaatgc caagaaagca gcagatgaga acagtggcgg    3180
tggtgaggca gctcaggaac acaatgaatg accactgacc cgtgaccttc cctttaggga    3240

<210> SEQ ID NO 17
<211> LENGTH: 2577
<212> TYPE: DNA
<213> ORGANISM: Mus musculus
```

<220> FEATURE:
<223> OTHER INFORMATION: mouse Sac non taster 129 T1R3 sweet taste
receptor CDS

<400> SEQUENCE: 17

| | | | | | |
|---|---|---|---|---|---|
| atgccagctt | tggctatcat | gggtctcagc | ctggctgctt | tcctggagct | tgggatgggg | 60 |
| gcctctttgt | gtctgtcaca | gcaattcaag | gcacaagggg | actacatact | gggcgggcta | 120 |
| tttcccctgg | gctcgaccga | ggaggccact | ctcaaccaga | gagcacaacc | caacagcacc | 180 |
| ctgtgtaaca | ggttctcacc | cctcggtttg | ttcctggcca | tggctatgaa | gatggctgtg | 240 |
| gaggagatca | acaatggatc | tgccttgctc | cctgggctgc | ggctgggcta | tgacctattt | 300 |
| gacacatgct | ccgagccagt | ggtcaccatg | aaatccagtc | tcatgttcct | ggccaaggtg | 360 |
| ggcagtcaaa | gcattgctgc | ctactgcaac | tacacacagt | accaaccccg | tgtgctggct | 420 |
| gtcatcggcc | cccactcatc | agagcttgcc | ctcattacag | gcaagttctt | cagcttcttc | 480 |
| ctcatgccac | aggtcagcta | tagcgccagc | atggatcggc | taagtgaccg | ggaaacgttt | 540 |
| ccatccttct | tccgcacagt | gcccagtgac | cgggtgcagc | tgcaggcagt | tgtgactctg | 600 |
| ttgcagaact | tcagctggaa | ctgggtggcc | gccttaggga | gtgatgatga | ctatggccgg | 660 |
| gaaggtctga | gcatctttc | tagtctggcc | aatgcacgag | gtatctgcat | cgcacatgag | 720 |
| ggcctggtgc | acaacatga | cactagtggc | caacagttgg | gcaaggtgct | ggatgtgcta | 780 |
| cgccaagtga | accaaagtaa | agtacaagtg | gtggtgctgt | ttgcctctgc | ccgtgctgtc | 840 |
| tactcccttt | ttagttacag | catccatcat | ggcctctcac | ccaaggtatg | ggtggccagt | 900 |
| gagtcttggc | tgacatctga | cctggtcatg | acacttccca | atattgcccg | tgtgggcact | 960 |
| gtgcttgggt | ttttgcagcg | gggtgcccta | ctgcctgaat | tttcccatta | tgtggagact | 1020 |
| caccttgccc | tggccgctga | cccagcattc | tgtgcctcac | tgaatgcgga | gttggatctg | 1080 |
| gaggaacatg | tgatggggca | acgctgtcca | cagtgtgacg | acatcatgct | gcagaaccta | 1140 |
| tcatctgggc | tgttgcagaa | cctatcagct | gggcaattgc | accaccaaat | atttgcaacc | 1200 |
| tatgcagctg | tgtacagtgt | ggctcaagcc | cttcacaaca | ccctacagtg | caatgtctca | 1260 |
| cattgccacg | tatcagaaca | tgttctaccc | tggcagctcc | tggagaacat | gtacaatatg | 1320 |
| agtttccatg | ctcgagactt | gacactacag | tttgatgctg | aagggaatgt | agacatggaa | 1380 |
| tatgacctga | agatgtgggt | gtggcagagc | cctacacctg | tattacatac | tgtgggcacc | 1440 |
| ttcaacggca | cccttcagct | gcagcagtct | aaaatgtact | ggccaggcaa | ccaggtgcca | 1500 |
| gtctcccagt | gttcccgcca | gtgcaaagat | ggccaggttc | gccgagtaaa | gggctttcat | 1560 |
| tcctgctgct | atgactgcgt | ggactgcaag | gcgggcagct | accggaagca | tccagatgac | 1620 |
| ttcacctgta | ctccatgtaa | ccaggaccag | tggtccccag | agaaaagcac | agcctgctta | 1680 |
| cctcgcaggc | ccaagtttct | ggcttggggg | gagccagttg | tgctgtcact | cctcctgctg | 1740 |
| cttttgcctg | gctgggtct | agcactggct | gctctgggc | tctctgtcca | ccactgggac | 1800 |
| agccctcttg | tccaggcctc | aggcggctca | cagttctgct | ttggcctgat | ctgcctaggc | 1860 |
| ctcttctgcc | tcagtgtcct | tctgttccca | ggacggccaa | gctctgccag | ctgccttgca | 1920 |
| caacaaccaa | tggctcacct | ccctctcaca | ggctgcctga | gcacactctt | cctgcaagca | 1980 |
| gctgagacct | ttgtggagtc | tgagctgcca | ctgagctggg | caaactggct | atgcagctac | 2040 |
| cttcggggac | tctgggcctg | gctagtggta | ctgttggcca | cttttgtgga | ggcagcacta | 2100 |
| tgtgcctggt | atttgaccgc | tttcccacca | gaggtggtga | cagactggtc | agtgctgccc | 2160 |
| acagaggtac | tggagcactg | ccacgtgcgt | tcctgggtca | gcctgggctt | ggtgcacatc | 2220 |

```
accaatgcaa tgttagcttt cctctgcttt ctgggcactt tcctggtaca gagccagcct    2280
ggccgctaca accgtgcccg tggtctcacc ttcgccatgc tagcttattt catcacctgg    2340
gtctcttttg tgcccctcct ggccaatgtg caggtggcct accagccagc tgtgcagatg    2400
ggtgctatcc tagtctgtgc cctgggcatc ctggtcacct tccacctgcc caagtgctat    2460
gtgcttcttt ggctgccaaa gctcaacacc caggagttct tcctgggaag gaatgccaag    2520
aaagcagcag atgagaacag tggcggtggt gaggcagctc aggaacacaa tgaatga      2577
```

<210> SEQ ID NO 18
<211> LENGTH: 858
<212> TYPE: PRT
<213> ORGANISM: Mus musculus
<220> FEATURE:
<223> OTHER INFORMATION: mouse Sac non taster 129 T1R3 sweet taste
      receptor

<400> SEQUENCE: 18

```
Met Pro Ala Leu Ala Ile Met Gly Leu Ser Leu Ala Ala Phe Leu Glu
 1               5                  10                  15

Leu Gly Met Gly Ala Ser Leu Cys Leu Ser Gln Gln Phe Lys Ala Gln
             20                  25                  30

Gly Asp Tyr Ile Leu Gly Gly Leu Phe Pro Leu Gly Ser Thr Glu Glu
         35                  40                  45

Ala Thr Leu Asn Gln Arg Ala Gln Pro Asn Ser Thr Leu Cys Asn Arg
     50                  55                  60

Phe Ser Pro Leu Gly Leu Phe Leu Ala Met Ala Met Lys Met Ala Val
 65                  70                  75                  80

Glu Glu Ile Asn Asn Gly Ser Ala Leu Leu Pro Gly Leu Arg Leu Gly
                 85                  90                  95

Tyr Asp Leu Phe Asp Thr Cys Ser Glu Pro Val Val Thr Met Lys Ser
            100                 105                 110

Ser Leu Met Phe Leu Ala Lys Val Gly Ser Gln Ser Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Leu Ile Thr Gly Lys Phe Phe Ser Phe Phe
145                 150                 155                 160

Leu Met Pro Gln Val Ser Tyr Ser Ala Ser Met Asp Arg Leu Ser Asp
                165                 170                 175

Arg Glu Thr Phe Pro Ser Phe Phe Arg Thr Val Pro Ser Asp Arg Val
            180                 185                 190

Gln Leu Gln Ala Val Val Thr Leu Leu Gln Asn Phe Ser Trp Asn Trp
        195                 200                 205

Val Ala Ala Leu Gly Ser Asp Asp Asp Tyr Gly Arg Glu Gly Leu Ser
    210                 215                 220

Ile Phe Ser Ser Leu Ala Asn Ala Arg Gly Ile Cys Ile Ala His Glu
225                 230                 235                 240

Gly Leu Val Pro Gln His Asp Thr Ser Gly Gln Gln Leu Gly Lys Val
                245                 250                 255

Leu Asp Val Leu Arg Gln Val Asn Gln Ser Lys Val Gln Val Val Val
            260                 265                 270

Leu Phe Ala Ser Ala Arg Ala Val Tyr Ser Leu Phe Ser Tyr Ser Ile
        275                 280                 285

His His Gly Leu Ser Pro Lys Val Trp Val Ala Ser Glu Ser Trp Leu
    290                 295                 300
```

```
Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
            325                 330                 335

Tyr Val Glu Thr His Leu Ala Leu Ala Ala Asp Pro Ala Phe Cys Ala
            340                 345                 350

Ser Leu Asn Ala Glu Leu Asp Leu Glu Glu His Val Met Gly Gln Arg
            355                 360                 365

Cys Pro Gln Cys Asp Asp Ile Met Leu Gln Asn Leu Ser Ser Gly Leu
        370                 375                 380

Leu Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Val Ser Glu His Val Leu Pro Trp Gln
                420                 425                 430

Leu Leu Glu Asn Met Tyr Asn Met Ser Phe His Ala Arg Asp Leu Thr
            435                 440                 445

Leu Gln Phe Asp Ala Glu Gly Asn Val Asp Met Glu Tyr Asp Leu Lys
450                 455                 460

Met Trp Val Trp Gln Ser Pro Thr Pro Val Leu His Thr Val Gly Thr
465                 470                 475                 480

Phe Asn Gly Thr Leu Gln Leu Gln Gln Ser Lys Met Tyr Trp Pro Gly
                485                 490                 495

Asn Gln Val Pro Val Ser Gln Cys Ser Arg Gln Cys Lys Asp Gly Gln
                500                 505                 510

Val Arg Arg Val Lys Gly Phe His Ser Cys Cys Tyr Asp Cys Val Asp
            515                 520                 525

Cys Lys Ala Gly Ser Tyr Arg Lys His Pro Asp Asp Phe Thr Cys Thr
            530                 535                 540

Pro Cys Asn Gln Asp Gln Trp Ser Pro Glu Lys Ser Thr Ala Cys Leu
545                 550                 555                 560

Pro Arg Arg Pro Lys Phe Leu Ala Trp Gly Glu Pro Val Val Leu Ser
                565                 570                 575

Leu Leu Leu Leu Leu Cys Leu Val Leu Gly Leu Ala Leu Ala Ala Leu
            580                 585                 590

Gly Leu Ser Val His His Trp Asp Ser Pro Leu Val Gln Ala Ser Gly
            595                 600                 605

Gly Ser Gln Phe Cys Phe Gly Leu Ile Cys Leu Gly Leu Phe Cys Leu
        610                 615                 620

Ser Val Leu Leu Phe Pro Gly Arg Pro Ser Ser Ala Ser Cys Leu Ala
625                 630                 635                 640

Gln Gln Pro Met Ala His Leu Pro Leu Thr Gly Cys Leu Ser Thr Leu
                645                 650                 655

Phe Leu Gln Ala Ala Glu Thr Phe Val Glu Ser Glu Leu Pro Leu Ser
            660                 665                 670

Trp Ala Asn Trp Leu Cys Ser Tyr Leu Arg Gly Leu Trp Ala Trp Leu
            675                 680                 685

Val Val Leu Leu Ala Thr Phe Val Glu Ala Ala Leu Cys Ala Trp Tyr
            690                 695                 700

Leu Thr Ala Phe Pro Pro Glu Val Val Thr Asp Trp Ser Val Leu Pro
705                 710                 715                 720

Thr Glu Val Leu Glu His Cys His Val Arg Ser Trp Val Ser Leu Gly
                725                 730                 735
```

```
Leu Val His Ile Thr Asn Ala Met Leu Ala Phe Leu Cys Phe Leu Gly
            740                 745                 750

Thr Phe Leu Val Gln Ser Gln Pro Gly Arg Tyr Asn Arg Ala Arg Gly
            755                 760                 765

Leu Thr Phe Ala Met Leu Ala Tyr Phe Ile Thr Trp Val Ser Phe Val
    770                 775                 780

Pro Leu Leu Ala Asn Val Gln Val Ala Tyr Gln Pro Ala Val Gln Met
785                 790                 795                 800

Gly Ala Ile Leu Val Cys Ala Leu Gly Ile Leu Val Thr Phe His Leu
                805                 810                 815

Pro Lys Cys Tyr Val Leu Leu Trp Leu Pro Lys Leu Asn Thr Gln Glu
                820                 825                 830

Phe Phe Leu Gly Arg Asn Ala Lys Lys Ala Ala Asp Glu Asn Ser Gly
                835                 840                 845

Gly Gly Glu Ala Ala Gln Glu His Asn Glu
    850                 855

<210> SEQ ID NO 19
<211> LENGTH: 2577
<212> TYPE: DNA
<213> ORGANISM: Mus musculus
<220> FEATURE:
<223> OTHER INFORMATION: mouse Sac taster SWR T1R3 sweet taste receptor
      CDS

<400> SEQUENCE: 19
atgccagctt tggctatcat gggtctcagc ctggctgctt tcctggagct tgggatgggg      60
gcctctttgt gtctgtcaca gcaattcaag gcacaagggg actacatact gggcgggcta     120
tttcccctgg gctcaaccga ggaggccact ctcaaccaga gaacacaacc caacagcatc     180
ctgtgtaaca ggttctcacc cctcggtttg ttcctggcca tggctatgaa gatggctgtg     240
gaggagatca caatggatc tgccttgctc cctgggctgc ggctgggcta tgacctattt     300
gacacatgct ccgagccagt ggtcaccatg aaatccagtc tcatgttcct ggccaaggtg     360
ggcagtcaaa gcattgctgc ctactgcaac tacacacagt accaaccccg tgtgctggct     420
gtcatcggcc cccactcatc agagcttgcc ctcattacag gcaagttctt cagcttcttc     480
ctcatgccac aggtcagcta tagcgccagc atggatcggc taagtgaccg ggaaacgttt     540
ccatccttct tccgcacagt gcccagtgac cgggtgcagc tgcaggcagt tgtgactctg     600
ttgcagaact tcagctggaa ctgggtggcc gccttaggag tgatgatga ctatggccgg     660 gaaggtctga gcatcttttc tagtctggcc aatgcacgag gtatctgcat cgcacatgag     720
ggcctggtgc acaacatga cactagtggc caacagttgg gcaaggtgct ggatgtgcta     780
tgccaagtga accaaagtaa agtacaagtg gtggtgctgt tgcctctgc ccgtgctgtc     840 tactcccttt ttagttacag catccatcat ggcctctcac ccaaggtatg ggtggccagt     900
gagtcttggc tgacatctga cctggtcatg acacttccca atattgcccg tgtgggcact     960
gtgcttgggt ttttgcagcg gggtgcccta ctgcctgaat tttcccatta tgtgagact    1020 caccttgccc tggccgctga cccagcattc tgtgcctcac tgaatgcgga gttggatctg    1080
gaggaacatg tgatggggca acgctgtcca cagtgtgacg acatcatgct gcagaaccta    1140
tcatctgggc tgttgcagaa cctatcagct gggcaattgc accaccaaat atttgcaacc    1200
tatgcagctg tgtacagtgt ggctcaagcc cttcacaaca ccctacagtg caatgtctca    1260
cattgccatg tatcagaaca tgttctaccc tggcagctcc tggagaacat gtacaatatg    1320
```

```
agtttccatg ctcgagactt gacactacag tttgatgctg aagggaatgt agacatggaa    1380
tatgacctga agatgtgggt gtggcagagc cctacacctg tattacatac tgtgggcacc    1440
ttcaacggca cccttcagct gcagcagtct aaaatgtact ggccaggcaa ccaggtgcca    1500
gtctcccagt gttcccgcca gtgcaaagat ggccaggttc gccgagtaaa gggctttcat    1560
tcctgctgct atgactgcgt ggactgcaag gcgggcagct accggaagca tccagatgac    1620
ttcacctgta ctccatgtaa ccaggaccag tggtccccag agaaaagcac agcctgctta    1680
cctcgcaggc ccaagtttct ggcttggggg gagccagttg tgctgtcact cctcctgctg    1740
cttttgcctgg tgctgggtct agcactggct gctctgggc tctctgtcca ccactgggac    1800
agccctcttg tccaggcctc aggcggctca cagttctgct ttggcctgat ctgcctaggc    1860
ctcttctgcc tcagtgtcct tctgttccca ggacggccaa gctctgccag ctgccttgca    1920
caacaaccaa tggctcacct ccctctcaca ggctgcctga gcacactctt cctgcaagca    1980
gctgagacct ttgtggagtc tgagctgcca ctgagctggg caaactggct atgcagctac    2040
cttcggggac tctgggcctg gctagtggta ctgtcggcca cttttgtgga ggcagcacta    2100
tgtgcctggt atttgaccgc tttcccacca gaggtggtga cagactggtc agtgctgccc    2160
acagaggtac tggagcactg ccacgtgcgt tcctgggtca gcctgggctt ggtgcacatc    2220
accaatgcaa tgttagcttt cctctgcttt ctgggcactt tcctggtaca gagccagcct    2280
ggccgctaca accgtgcccg tggtctcacc ttcgccatgc tagcttattt catcacctgg    2340
gtctcttttg tgcccctcct ggccaatgtg caggtggcct accagccagc tgtgcagatg    2400
ggtgctatcc tagtctgtgc cctgggcatc ctggtcacct tccacctgcc caagtgctat    2460
gtgcttcttt ggctgccaaa gctcaacacc caggagttct tcctgggaag gaatgccaag    2520
aaagcagcag atgagaacag tggcggtggt gaggcagctc aggaacacaa tgaatga       2577
```

<210> SEQ ID NO 20
<211> LENGTH: 858
<212> TYPE: PRT
<213> ORGANISM: Mus musculus
<220> FEATURE:
<223> OTHER INFORMATION: mouse Sac taster SWR T1R3 sweet taste receptor

<400> SEQUENCE: 20

```
Met Pro Ala Leu Ala Ile Met Gly Leu Ser Leu Ala Ala Phe Leu Glu
 1               5                  10                  15

Leu Gly Met Gly Ala Ser Leu Cys Leu Ser Gln Gln Phe Lys Ala Gln
                20                  25                  30

Gly Asp Tyr Ile Leu Gly Gly Leu Phe Pro Leu Gly Ser Thr Glu Glu
            35                  40                  45

Ala Thr Leu Asn Gln Arg Thr Gln Pro Asn Ser Ile Leu Cys Asn Arg
        50                  55                  60

Phe Ser Pro Leu Gly Leu Phe Leu Ala Met Ala Met Lys Met Ala Val
65                  70                  75                  80

Glu Glu Ile Asn Asn Gly Ser Ala Leu Leu Pro Gly Leu Arg Leu Gly
                85                  90                  95

Tyr Asp Leu Phe Asp Thr Cys Ser Glu Pro Val Val Thr Met Lys Ser
            100                 105                 110

Ser Leu Met Phe Leu Ala Lys Val Gly Ser Gln Ser Ile Ala Ala Tyr
        115                 120                 125

Cys Asn Tyr Thr Gln Tyr Gln Pro Arg Val Leu Ala Val Ile Gly Pro
    130                 135                 140

His Ser Ser Glu Leu Ala Leu Ile Thr Gly Lys Phe Phe Ser Phe Phe
```

-continued

```
            145                 150                 155                 160
        Leu Met Pro Gln Val Ser Tyr Ser Ala Ser Met Asp Arg Leu Ser Asp
                        165                 170                 175

Arg Glu Thr Phe Pro Ser Phe Phe Arg Thr Val Pro Ser Asp Arg Val
                        180                 185                 190

Gln Leu Gln Ala Val Val Thr Leu Leu Gln Asn Phe Ser Trp Asn Trp
                        195                 200                 205

Val Ala Ala Leu Gly Ser Asp Asp Tyr Gly Arg Glu Gly Leu Ser
            210                 215                 220

Ile Phe Ser Ser Leu Ala Asn Ala Arg Gly Ile Cys Ile Ala His Glu
        225                 230                 235                 240

Gly Leu Val Pro Gln His Asp Thr Ser Gly Gln Gln Leu Gly Lys Val
                        245                 250                 255

Leu Asp Val Leu Cys Gln Val Asn Gln Ser Lys Val Gln Val Val
                        260                 265                 270

Leu Phe Ala Ser Ala Arg Ala Val Tyr Ser Leu Phe Ser Tyr Ser Ile
                        275                 280                 285

His His Gly Leu Ser Pro Lys Val Trp Val Ala Ser Glu Ser Trp Leu
            290                 295                 300

Thr Ser Asp Leu Val Met Thr Leu Pro Asn Ile Ala Arg Val Gly Thr
        305                 310                 315                 320

Val Leu Gly Phe Leu Gln Arg Gly Ala Leu Leu Pro Glu Phe Ser His
                        325                 330                 335

Tyr Val Glu Thr His Leu Ala Leu Ala Ala Asp Pro Ala Phe Cys Ala
                        340                 345                 350

Ser Leu Asn Ala Glu Leu Asp Leu Glu Glu His Val Met Gly Gln Arg
                        355                 360                 365

Cys Pro Gln Cys Asp Asp Ile Met Leu Gln Asn Leu Ser Ser Gly Leu
            370                 375                 380

Leu Gln Asn Leu Ser Ala Gly Gln Leu His His Gln Ile Phe Ala Thr
        385                 390                 395                 400

Tyr Ala Ala Val Tyr Ser Val Ala Gln Ala Leu His Asn Thr Leu Gln
                        405                 410                 415

Cys Asn Val Ser His Cys His Val Ser Glu His Val Leu Pro Trp Gln
                        420                 425                 430

Leu Leu Glu Asn Met Tyr Asn Met Ser Phe His Ala Arg Asp Leu Thr
                        435                 440                 445

Leu Gln Phe Asp Ala Glu Gly Asn Val Asp Met Glu Tyr Asp Leu Lys
            450                 455                 460

Met Trp Val Trp Gln Ser Pro Thr Pro Val Leu His Thr Val Gly Thr
        465                 470                 475                 480

Phe Asn Gly Thr Leu Gln Leu Gln Gln Ser Lys Met Tyr Trp Pro Gly
                        485                 490                 495

Asn Gln Val Pro Val Ser Gln Cys Ser Arg Gln Cys Lys Asp Gly Gln
                        500                 505                 510

Val Arg Arg Val Lys Gly Phe His Ser Cys Cys Tyr Asp Cys Val Asp
            515                 520                 525

Cys Lys Ala Gly Ser Tyr Arg Lys His Pro Asp Asp Phe Thr Cys Thr
            530                 535                 540

Pro Cys Asn Gln Asp Gln Trp Ser Pro Glu Lys Ser Thr Ala Cys Leu
        545                 550                 555                 560

Pro Arg Arg Pro Lys Phe Leu Ala Trp Gly Glu Pro Val Val Leu Ser
                        565                 570                 575
```

```
Leu Leu Leu Leu Leu Cys Leu Val Leu Gly Leu Ala Leu Ala Ala Leu
                580                 585                 590
Gly Leu Ser Val His His Trp Asp Ser Pro Leu Val Gln Ala Ser Gly
            595                 600                 605
Gly Ser Gln Phe Cys Phe Gly Leu Ile Cys Leu Gly Leu Phe Cys Leu
        610                 615                 620
Ser Val Leu Leu Phe Pro Gly Arg Pro Ser Ala Ser Cys Leu Ala
625                 630                 635                 640
Gln Gln Pro Met Ala His Leu Pro Leu Thr Gly Cys Leu Ser Thr Leu
                645                 650                 655
Phe Leu Gln Ala Ala Glu Thr Phe Val Glu Ser Glu Leu Pro Leu Ser
                660                 665                 670
Trp Ala Asn Trp Leu Cys Ser Tyr Leu Arg Gly Leu Trp Ala Trp Leu
            675                 680                 685
Val Val Leu Ser Ala Thr Phe Val Glu Ala Ala Leu Cys Ala Trp Tyr
        690                 695                 700
Leu Thr Ala Phe Pro Pro Glu Val Val Thr Asp Trp Ser Val Leu Pro
705                 710                 715                 720
Thr Glu Val Leu Glu His Cys His Val Arg Ser Trp Val Ser Leu Gly
                725                 730                 735
Leu Val His Ile Thr Asn Ala Met Leu Ala Phe Leu Cys Phe Leu Gly
                740                 745                 750
Thr Phe Leu Val Gln Ser Gln Pro Gly Arg Tyr Asn Arg Ala Arg Gly
            755                 760                 765
Leu Thr Phe Ala Met Leu Ala Tyr Phe Ile Thr Trp Val Ser Phe Val
        770                 775                 780
Pro Leu Leu Ala Asn Val Gln Val Ala Tyr Gln Pro Ala Val Gln Met
785                 790                 795                 800
Gly Ala Ile Leu Val Cys Ala Leu Gly Ile Leu Val Thr Phe His Leu
                805                 810                 815
Pro Lys Cys Tyr Val Leu Leu Trp Leu Pro Lys Leu Asn Thr Gln Glu
                820                 825                 830
Phe Phe Leu Gly Arg Asn Ala Lys Lys Ala Ala Asp Glu Asn Ser Gly
            835                 840                 845
Gly Gly Glu Ala Ala Gln Glu His Asn Glu
    850                 855

<210> SEQ ID NO 21
<211> LENGTH: 3200
<212> TYPE: DNA
<213> ORGANISM: Mus musculus
<220> FEATURE:
<223> OTHER INFORMATION: mouse Sac taster C57 T1R3 sweet taste receptor
      genomic

<400> SEQUENCE: 21
cccacacacc cacccattgt tagtgctgga gacttctacc taccatgcca gctttggcta      60
tcatgggtct cagcctggct gctttcctgg agcttgggat ggggccctct ttgtgtctgt     120
cacagcaatt caaggcacaa ggggactaca tactgggcgg gctatttccc ctgggctcaa     180
ccgaggaggc cactctcaac cagagaacac aacccaacag catcccgtgc aacaggtatg     240
gaggctagta gctggggtgg gagtgaaccg aagcttggca gctttggctc cgtggtacta     300
ccaatctggg aagaggtggt gatcagtttc catgtggcct caggttctca ccccttggtt     360
tgttcctggc catggctatg aagatggctg tggaggagat caacaatgga tctgccttgc     420
tccctgggct gcggctgggc tatgacctat ttgacacatg ctccgagcca gtggtcacca     480
```

-continued

```
tgaaatccag tctcatgttc ctggccaagg tgggcagtca aagcattgct gcctactgca    540
actacacaca gtaccaaccc cgtgtgctgg ctgtcatcgg cccccactca tcagagcttg    600
ccctcattac aggcaagttc ttcagcttct tcctcatgcc acaggtgagc ccacttcctt    660
tgtgttctca accgattgca cccattgagc tctcatatca gaaagtgctt cttgatcacc    720
acaggtcagc tatagtgcca gcatggatcg gctaagtgac cgggaaacgt ttccatcctt    780
cttccgcaca gtgcccagtg accgggtgca gctgcaggca gttgtgactc tgttgcagaa    840
cttcagctgg aactgggtgg ccgccttagg gagtgatgat gactatgccc gggaaggtct    900
gagcatcttt tctagtctgg ccaatgcacg aggtatctgc atcgcacatg agggcctggt    960
gccacaacat gacactagtg gccaacagtt gggcaaggtg ctggatgtac tacgccaagt   1020
gaaccaaagt aaagtacaag tggtggtgct gtttgcctct gcccgtgctg tctactccct   1080
ttttagttac agcatccatc atggcctctc acccaaggta tgggtggcca gtgagtcttg   1140
gctgacatct gacctggtca tgacacttcc caatattgcc cgtgtgggca ctgtgcttgg   1200
gtttttgcag cggggtgccc tactgcctga attttcccat tatgtggaga ctcaccttgc   1260
cctggccgct gacccagcat tctgtgcctc actgaatgcg gagttggatc tggaggaaca   1320
tgtgatgggg caacgctgtc cacggtgtga cgacatcatg ctgcagaacc tatcatctgg   1380
gctgttgcag aacctatcag ctgggcaatt gcaccaccaa atatttgcaa cctatgcagc   1440
tgtgtacagt gtggctcaag cccttcacaa caccctacag tgcaatgtct cacattgcca   1500
cgtatcagaa catgttctac cctggcaggt aagggtaggg ttttttgctg ggttttgcct   1560
gctcctgcag gaacactgaa ccaggcagag ccaaatcttg ttgtgactgg agaggcctta   1620
ccctgactcc actccacagc tcctggagaa catgtacaat atgagtttcc atgctcgaga   1680
cttgacacta cagtttgatg ctgaagggaa tgtagacatg gaatatgacc tgaagatgtg   1740
ggtgtggcag agccctacac ctgtattaca tactgtgggc accttcaacg caccccttca   1800
gctgcagcag tctaaaatgt actggccagg caaccaggta aggacaagac aggcaaaaag   1860
gatggtgggt agaagcttgt cggtcttggg ccagtgctag ccaaggggag gcctaaccca   1920
aggctccatg tacaggtgcc agtctcccag tgttcccgcc agtgcaaaga tggccaggtt   1980
cgccgagtaa agggctttca ttcctgctgc tatgactgcg tggactgcaa ggcgggcagc   2040
taccggaagc atccaggtga accgtcttcc ctagacagtc tgcacagccg gctaggggg   2100
cagaagcatt caagtctggc aagcgccctc ccgcggggct aatgtggaga cagttactgt   2160
gggggctggc tggggaggtc ggtctcccat cagcagaccc cacattactt ttcttccttc   2220
catcactaca gatgacttca cctgtactcc atgtaaccag gaccagtggt ccccagagaa   2280
aagcacagcc tgcttacctc gcaggcccaa gtttctggct tgggggagc cagttgtgct   2340
gtcactcctc ctgctgcttt gcctggtgct gggtctagca ctggctgctc tggggctctc   2400
tgtccaccac tgggacagcc ctcttgtcca ggcctcaggt ggctcacagt tctgctttgg   2460
cctgatctgc ctaggcctct tctgcctcag tgtccttctg ttcccagggc ggccaagctc   2520
tgccagctgc cttgcacaac aaccaatggc tcacctccct ctcacaggct gcctgagcac   2580
actcttcctg caagcagctg agacctttgt ggagtctgag ctgccactga ctgggcaaa   2640
ctggctatgc agctaccttc ggggactctg gcctggcta gtggtactgt ggccactttt   2700
tgtggaggca gcactatgtg cctggtattt gatcgctttc ccaccagagg tggtgacaga   2760
ctggtcagtc ctgcccacag aggtactgga gcactgccac gtgcgttcct gggtcagcct   2820
gggcttggtg cacatcacca atgcaatgtt agctttcctc tgctttctgg gcacttttcct   2880
```

| | |
|---|---|
| ggtacagagc cagcctggcc gctacaaccg tgcccgtggt ctcaccttcg ccatgctagc | 2940 |
| ttatttcatc acctgggtct cttttgtgcc cctcctggcc aatgtgcagg tggcctacca | 3000 |
| gccagctgtg cagatgggtg ctatcctagt ctgtgccctg gcatcctgg tcaccttcca | 3060 |
| cctgcccaag tgctatgtgc ttctttggct gccaaagctc aacacccagg agttcttcct | 3120 |
| gggaaggaat gccaagaaag cagcagatga aacagtggc ggtggtgagg cagctcaggg | 3180 |
| acacaatgaa tgaccactga | 3200 |

<210> SEQ ID NO 22
<211> LENGTH: 2577
<212> TYPE: DNA
<213> ORGANISM: Mus musculus
<220> FEATURE:
<223> OTHER INFORMATION: mouse Sac taster C57 T1R3 sweet taste receptor
      CDS

<400> SEQUENCE: 22

| | |
|---|---|
| atgccagctt tggctatcat gggtctcagc ctggctgctt cctggagct tgggatgggg | 60 |
| gcctctttgt gtctgtcaca gcaattcaag gcacaagggg actacatact gggcgggcta | 120 |
| tttcccctgg gctcaaccga ggaggccact ctcaaccaga gaacacaacc caacagcatc | 180 |
| ccgtgcaaca ggttctcacc ccttggtttg ttcctggcca tggctatgaa gatggctgtg | 240 |
| gaggagatca acaatggatc tgccttgctc cctgggctgc ggctgggcta tgacctattt | 300 |
| gacacatgct ccgagccagt ggtcaccatg aaatccagtc tcatgttcct ggccaaggtg | 360 |
| ggcagtcaaa gcattgctgc ctactgcaac tacacacagt accaaccccg tgtgctggct | 420 |
| gtcatcggcc cccactcatc agagcttgcc ctcattacag gcaagttctt cagcttcttc | 480 |
| ctcatgccac aggtcagcta tagtgccagc atggatcggc taagtgaccg ggaaacgttt | 540 |
| ccatccttct ccgcacagt gcccagtgac cgggtgcagc tgcaggcagt tgtgactctg | 600 |
| ttgcagaact tcagctggaa ctgggtggcc gccttaggga gtgatgatga ctatggccgg | 660 |
| gaaggtctga gcatcttttc tagtctggcc aatgcacgag gtatctgcat cgcacatgag | 720 |
| ggcctggtgc acaacatga cactagtggc caacagttgg gcaaggtgct ggatgtacta | 780 |
| cgccaagtga accaaagtaa agtcaaagtg gtggtgctgt tgcctctgc ccgtgctgtc | 840 |
| tactcccttt tagttacag catccatcat ggcctctcac ccaaggtatg ggtggccagt | 900 |
| gagtcttggc tgacatctga cctggtcatg acacttccca atattgcccg tgtgggcact | 960 |
| gtgcttgggt ttttgcagcg gggtgcccta ctgcctgaat tttcccatta tgtggagact | 1020 |
| caccttgccc tggccgctga cccagcattc tgtgcctcac tgaatgcgga gttggatctg | 1080 |
| gaggaacatg tgatgggca cgctgtcca ggtgtgacg acatcatgct gcagaaccta | 1140 |
| tcatctgggc tgttgcagaa cctatcagct gggcaattgc accaccaaat atttgcaacc | 1200 |
| tatgcagctg tgtacagtgt ggctcaagcc cttcacaaca cctacagtgc aatgtctca | 1260 |
| cattgccacg tatcagaaca tgttctaccc tggcagctcc tggagaacat gtacaatatg | 1320 |
| agtttccatg ctcgagactt gacactacag tttgatgctg aagggaatgt agacatggaa | 1380 |
| tatgacctga agatgtgggt gtggcagagc cctacacctg tattacatac tgtgggcacc | 1440 |
| ttcaacggca cccttcagct gcagcagtct aaaatgtact ggccaggcaa ccaggtgcca | 1500 |
| gtctccccagt gttcccgcca gtgcaaagat ggccaggttc gccgagtaaa gggctttcat | 1560 |
| tcctgctgct atgactgcgt ggactgcaag gcgggcagct accggaagca tccagatgac | 1620 |
| ttcacctgta ctccatgtaa ccaggaccag tggtccccag agaaaagcac agcctgctta | 1680 |

```
cctcgcaggc caagtttct ggcttggggg gagccagttg tgctgtcact cctcctgctg    1740
ctttgcctgg tgctgggtct agcactggct gctctggggc tctctgtcca ccactgggac    1800
agccctcttg tccaggcctc aggtggctca cagttctgct ttggcctgat ctgcctaggc    1860
ctcttctgcc tcagtgtcct tctgttccca gggcggccaa gctctgccag ctgccttgca    1920
caacaaccaa tggctcacct ccctctcaca ggctgcctga gcacactctt cctgcaagca    1980
gctgagacct ttgtggagtc tgagctgcca ctgagctggg caaactggct atgcagctac    2040
cttcggggac tctgggcctg gctagtggta ctgttggcca cttttgtgga ggcagcacta    2100
tgtgcctggt atttgatcgc tttcccacca gaggtggtga cagactggtc agtgctgccc    2160
acagaggtac tggagcactg ccacgtgcgt tcctgggtca gcctgggctt ggtgcacatc    2220
accaatgcaa tgttagcttt cctctgcttt ctgggcactt tcctggtaca gagccagcct    2280
ggccgctaca accgtgcccg tggtctcacc ttcgccatgc tagcttattt catcacctgg    2340
gtctcttttg tgcccctcct ggccaatgtg caggtggcct accagccagc tgtgcagatg    2400
ggtgctatcc tagtctgtgc cctgggcatc ctggtcacct tccacctgcc caagtgctat    2460
gtgcttcttt ggctgccaaa gctcaacacc caggagttct tcctgggaag gaatgccaag    2520
aaagcagcag atgagaacag tggcggtggt gaggcagctc agggacacaa tgaatga      2577
```

<210> SEQ ID NO 23
<211> LENGTH: 858
<212> TYPE: PRT
<213> ORGANISM: Mus musculus
<220> FEATURE:
<223> OTHER INFORMATION: mouse Sac taster C57 T1R3 sweet taste receptor

<400> SEQUENCE: 23

```
Met Pro Ala Leu Ala Ile Met Gly Leu Ser Leu Ala Ala Phe Leu Glu
 1               5                  10                  15

Leu Gly Met Gly Ala Ser Leu Cys Leu Ser Gln Gln Phe Lys Ala Gln
                20                  25                  30

Gly Asp Tyr Ile Leu Gly Gly Leu Phe Pro Leu Gly Ser Thr Glu Glu
            35                  40                  45

Ala Thr Leu Asn Gln Arg Thr Gln Pro Asn Ser Ile Pro Cys Asn Arg
        50                  55                  60

Phe Ser Pro Leu Gly Leu Phe Leu Ala Met Ala Met Lys Met Ala Val
 65                  70                  75                  80

Glu Glu Ile Asn Asn Gly Ser Ala Leu Leu Pro Gly Leu Arg Leu Gly
                85                  90                  95

Tyr Asp Leu Phe Asp Thr Cys Ser Glu Pro Val Val Thr Met Lys Ser
               100                 105                 110

Ser Leu Met Phe Leu Ala Lys Val Gly Ser Gln Ser Ile Ala Ala Tyr
           115                 120                 125

Cys Asn Tyr Thr Gln Tyr Gln Pro Arg Val Leu Ala Val Ile Gly Pro
       130                 135                 140

His Ser Ser Glu Leu Ala Leu Ile Thr Gly Lys Phe Phe Ser Phe Phe
145                 150                 155                 160

Leu Met Pro Gln Val Ser Tyr Ser Ala Ser Met Asp Arg Leu Ser Asp
               165                 170                 175

Arg Glu Thr Phe Pro Ser Phe Phe Arg Thr Val Pro Ser Asp Arg Val
           180                 185                 190

Gln Leu Gln Ala Val Val Thr Leu Leu Gln Asn Phe Ser Trp Asn Trp
       195                 200                 205

Val Ala Ala Leu Gly Ser Asp Asp Asp Tyr Gly Arg Glu Gly Leu Ser
```

-continued

```
              210                 215                 220
Ile Phe Ser Ser Leu Ala Asn Ala Arg Gly Ile Cys Ile Ala His Glu
225                 230                 235                 240

Gly Leu Val Pro Gln His Asp Thr Ser Gly Gln Gln Leu Gly Lys Val
                245                 250                 255

Leu Asp Val Leu Arg Gln Val Asn Gln Ser Lys Val Gln Val Val Val
                260                 265                 270

Leu Phe Ala Ser Ala Arg Ala Val Tyr Ser Leu Phe Ser Tyr Ser Ile
                275                 280                 285

His His Gly Leu Ser Pro Lys Val Trp Val Ala Ser Glu Ser Trp Leu
            290                 295                 300

Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
                325                 330                 335

Tyr Val Glu Thr His Leu Ala Leu Ala Ala Asp Pro Ala Phe Cys Ala
                340                 345                 350

Ser Leu Asn Ala Glu Leu Asp Leu Glu Glu His Val Met Gly Gln Arg
            355                 360                 365

Cys Pro Arg Cys Asp Asp Ile Met Leu Gln Asn Leu Ser Ser Gly Leu
370                 375                 380

Leu Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
                405                 410                 415

Cys Asn Val Ser His Cys His Val Ser Glu His Val Leu Pro Trp Gln
                420                 425                 430

Leu Leu Glu Asn Met Tyr Asn Met Ser Phe His Ala Arg Asp Leu Thr
            435                 440                 445

Leu Gln Phe Asp Ala Glu Gly Asn Val Asp Met Glu Tyr Asp Leu Lys
            450                 455                 460

Met Trp Val Trp Gln Ser Pro Thr Pro Val Leu His Thr Val Gly Thr
465                 470                 475                 480

Phe Asn Gly Thr Leu Gln Leu Gln Gln Ser Lys Met Tyr Trp Pro Gly
                485                 490                 495

Asn Gln Val Pro Val Ser Gln Cys Ser Arg Gln Cys Lys Asp Gly Gln
                500                 505                 510

Val Arg Arg Val Lys Gly Phe His Ser Cys Cys Tyr Asp Cys Val Asp
            515                 520                 525

Cys Lys Ala Gly Ser Tyr Arg Lys His Pro Asp Asp Phe Thr Cys Thr
530                 535                 540

Pro Cys Asn Gln Asp Gln Trp Ser Pro Glu Lys Ser Thr Ala Cys Leu
545                 550                 555                 560

Pro Arg Arg Pro Lys Phe Leu Ala Trp Gly Glu Pro Val Val Leu Ser
                565                 570                 575

Leu Leu Leu Leu Leu Cys Leu Val Leu Gly Leu Ala Leu Ala Ala Leu
                580                 585                 590

Gly Leu Ser Val His His Trp Asp Ser Pro Leu Val Gln Ala Ser Gly
            595                 600                 605

Gly Ser Gln Phe Cys Phe Gly Leu Ile Cys Leu Gly Leu Phe Cys Leu
            610                 615                 620

Ser Val Leu Leu Phe Pro Gly Arg Pro Ser Ser Ala Ser Cys Leu Ala
625                 630                 635                 640
```

```
Gln Gln Pro Met Ala His Leu Pro Leu Thr Gly Cys Leu Ser Thr Leu
                645                 650                 655
Phe Leu Gln Ala Ala Glu Thr Phe Val Glu Ser Glu Leu Pro Leu Ser
            660                 665                 670
Trp Ala Asn Trp Leu Cys Ser Tyr Leu Arg Gly Leu Trp Ala Trp Leu
        675                 680                 685
Val Val Leu Leu Ala Thr Phe Val Glu Ala Ala Leu Cys Ala Trp Tyr
    690                 695                 700
Leu Ile Ala Phe Pro Pro Glu Val Val Thr Asp Trp Ser Val Leu Pro
705                 710                 715                 720
Thr Glu Val Leu Glu His Cys His Val Arg Ser Trp Val Ser Leu Gly
                725                 730                 735
Leu Val His Ile Thr Asn Ala Met Leu Ala Phe Leu Cys Phe Leu Gly
            740                 745                 750
Thr Phe Leu Val Gln Ser Gln Pro Gly Arg Tyr Asn Arg Ala Arg Gly
        755                 760                 765
Leu Thr Phe Ala Met Leu Ala Tyr Phe Ile Thr Trp Val Ser Phe Val
    770                 775                 780
Pro Leu Leu Ala Asn Val Gln Val Ala Tyr Gln Pro Ala Val Gln Met
785                 790                 795                 800
Gly Ala Ile Leu Val Cys Ala Leu Gly Ile Leu Val Thr Phe His Leu
                805                 810                 815
Pro Lys Cys Tyr Val Leu Leu Trp Leu Pro Lys Leu Asn Thr Gln Glu
            820                 825                 830
Phe Phe Leu Gly Arg Asn Ala Lys Lys Ala Ala Asp Glu Asn Ser Gly
        835                 840                 845
Gly Gly Glu Ala Ala Gln Gly His Asn Glu
    850                 855

<210> SEQ ID NO 24
<211> LENGTH: 2577
<212> TYPE: DNA
<213> ORGANISM: Rattus sp.
<220> FEATURE:
<223> OTHER INFORMATION: rat T1R3 sweet taste receptor CDS

<400> SEQUENCE: 24
atgccgggtt tggctatctt gggcctcagt ctggctgctt tcctggagct tgggatgggg      60
tcctctttgt gtctgtcaca gcaattcaag gcacaagggg actatatatt gggtggacta     120
tttcccctgg gcacaactga ggaggccact ctcaaccaga aacacagcc caacggcatc     180 ctatgtacca ggttctcgcc ccttggtttg ttcctggcca tggctatgaa gatggctgta     240
gaggagatca caatggatc tgccttgctc cctgggctgc gactgggcta tgacctgttt     300
gacacatgct cagagccagt ggtcaccatg aagcccagcc tcatgttcat ggccaaggtg     360
ggaagtcaaa gcattgctgc ctactgcaac tacacacagt accaaccccg tgtgctggct     420
gtcattggtc cccactcatc agagcttgcc ctcattacag gcaagttctt cagcttcttc     480
ctcatgccac aggtcagcta tagtgccagc atggatcggc taagtgaccg gaaacatttt     540
ccatccttct tccgcacagt gcccagtgac cgggtgcagc tgcaggccgt tgtgacactg     600
ttgcagaatt tcagctggaa ctgggtggct gccttaggta gtgatgatga ctatggccgg     660
gaaggtctga gcatcttttc tggtctggcc aactcacgag gtatctgcat tgcacacgag     720
ggcctggtgc acaacatga cactagtggc aacaattgg gcaaggtggt ggatgtgcta     780
cgccaagtga accaaagcaa agtacaggtg gtggtgctgt ttgcatctgc ccgtgctgtc     840
```

-continued

```
tactcccttt ttagctacag catccttcat gacctctcac ccaaggtatg ggtggccagt        900
gagtcctggc tgacctctga cctggtcatg acacttccca atattgcccg tgtgggcact        960
gttcttgggt ttctgcagcg cggtgcccta ctgcctgaat tttcccatta tgtggagact       1020
cgccttgccc tagctgctga cccaacattc tgtgcctccc tgaaagctga gttggatctg       1080
gaggagcgcg tgatggggcc acgctgttca caatgtgact acatcatgct acagaacctg       1140
tcatctgggc tgatgcagaa cctatcagct gggcagttgc accaccaaat atttgcaacc       1200
tatgcagctg tgtacagtgt ggctcaggcc cttcacaaca ccctgcagtg caatgtctca       1260
cattgccaca catcagagcc tgttcaaccc tggcagctcc tggagaacat gtacaatatg       1320
agtttccgtg ctcgagactt gacactgcag tttgatgcca agggagtgt agacatggaa        1380 tatgacctga agatgtgggt gtggcagagc cctacacctg tactacatac tgtaggcacc       1440
ttcaacggca cccttcagct gcagcactcg aaaatgtatt ggccaggcaa ccaggtgcca       1500
gtctcccagt gctcccggca gtgcaaagat ggccaggtgc gcagagtaaa gggcttttcat      1560 tcctgctgct atgactgtgt ggactgcaag gcagggagct accggaagca tccagatgac       1620
ttcacctgta ctccatgtgg caaggatcag tggtccccag aaaaaagcac aacctgctta       1680
cctcgcaggc ccaagtttct ggcttggggg agccagctg tgctgtcact tctcctgctg        1740 cttgcctgg tgctgggcct gacactggct gccctgggc tctttgtcca ctactgggac         1800
agccctcttg ttcaggcctc aggtgggtca ctgttctgct ttggcctgat ctgcctaggc       1860
ctcttctgcc tcagtgtcct tctgttccca ggacgaccac gctctgccag ctgccttgcc       1920
caacaaccaa tggctcacct ccctctcaca ggctgcctga gcacactctt cctgcaagca       1980
gccgagatct ttgtggagtc tgagctgcca ctgagttggg caaactggct ctgcagctac       2040
cttcggggcc cctgggcttg gctggtggta ctgctggcca ctcttgtgga ggctgcacta       2100
tgtgcctggt acttgatggc tttccctcca gaggtggtga cagattggca ggtgctgccc       2160
acggaggtac tggaacactg ccgcatgcgt tcctgggtca gcctgggctt ggtgcacatc       2220
accaatgcag tgttagcttt cctctgcttt ctgggcactt tcctggtaca gagccagcct       2280
ggtcgctata accgtgcccg tggcctcacc ttcgccatgc tagcttattt catcatctgg       2340
gtctcttttg tgcccctcct ggctaatgtg caggtggcct accagccagc tgtgcagatg       2400
ggtgctatct tattctgtgc cctgggcatc ctggccacct tccacctgcc caatgctat        2460 gtacttctgt ggctgccaga gctcaacacc caggagttct tcctgggaag gagccccaag       2520
gaagcatcag atgggaatag tggtagtagt gaggcaactc ggggacacag tgaatga          2577
```

<210> SEQ ID NO 25
<211> LENGTH: 858
<212> TYPE: PRT
<213> ORGANISM: Rattus sp.
<220> FEATURE:
<223> OTHER INFORMATION: rat T1R3 sweet taste receptor

<400> SEQUENCE: 25

```
Met Pro Gly Leu Ala Ile Leu Gly Leu Ser Leu Ala Ala Phe Leu Glu
 1               5                  10                  15

Leu Gly Met Gly Ser Ser Leu Cys Leu Ser Gln Gln Phe Lys Ala Gln
            20                  25                  30

Gly Asp Tyr Ile Leu Gly Gly Leu Phe Pro Leu Gly Thr Thr Glu Glu
        35                  40                  45

Ala Thr Leu Asn Gln Arg Thr Gln Pro Asn Gly Ile Leu Cys Thr Arg
    50                  55                  60
```

```
Phe Ser Pro Leu Gly Leu Phe Leu Ala Met Ala Met Lys Met Ala Val
 65                  70                  75                  80

Glu Glu Ile Asn Asn Gly Ser Ala Leu Leu Pro Gly Leu Arg Leu Gly
                 85                  90                  95

Tyr Asp Leu Phe Asp Thr Cys Ser Glu Pro Val Val Thr Met Lys Pro
            100                 105                 110

Ser Leu Met Phe Met Ala Lys Val Gly Ser Gln Ser Ile Ala Ala Tyr
        115                 120                 125

Cys Asn Tyr Thr Gln Tyr Gln Pro Arg Val Leu Ala Val Ile Gly Pro
130                 135                 140

His Ser Ser Glu Leu Ala Leu Ile Thr Gly Lys Phe Phe Ser Phe Phe
145                 150                 155                 160

Leu Met Pro Gln Val Ser Tyr Ser Ala Ser Met Asp Arg Leu Ser Asp
            165                 170                 175

Arg Glu Thr Phe Pro Ser Phe Phe Arg Thr Val Pro Ser Asp Arg Val
        180                 185                 190

Gln Leu Gln Ala Val Val Thr Leu Leu Gln Asn Phe Ser Trp Asn Trp
    195                 200                 205

Val Ala Ala Leu Gly Ser Asp Asp Tyr Gly Arg Glu Gly Leu Ser
210                 215                 220

Ile Phe Ser Gly Leu Ala Asn Ser Arg Gly Ile Cys Ile Ala His Glu
225                 230                 235                 240

Gly Leu Val Pro Gln His Asp Thr Ser Gly Gln Gln Leu Gly Lys Val
            245                 250                 255

Val Asp Val Leu Arg Gln Val Asn Gln Ser Lys Val Gln Val Val Val
        260                 265                 270

Leu Phe Ala Ser Ala Arg Ala Val Tyr Ser Leu Phe Ser Tyr Ser Ile
    275                 280                 285

Leu His Asp Leu Ser Pro Lys Val Trp Val Ala Ser Glu Ser Trp Leu
290                 295                 300

Thr Ser Asp Leu Val Met Thr Leu Pro Asn Ile Ala Arg Val Gly Thr
305                 310                 315                 320

Val Leu Gly Phe Leu Gln Arg Gly Ala Leu Leu Pro Glu Phe Ser His
            325                 330                 335

Tyr Val Glu Thr Arg Leu Ala Leu Ala Ala Asp Pro Thr Phe Cys Ala
        340                 345                 350

Ser Leu Lys Ala Glu Leu Asp Leu Glu Glu Arg Val Met Gly Pro Arg
    355                 360                 365

Cys Ser Gln Cys Asp Tyr Ile Met Leu Gln Asn Leu Ser Ser Gly Leu
370                 375                 380

Met Gln Asn Leu Ser Ala Gly Gln Leu His His Gln Ile Phe Ala Thr
385                 390                 395                 400

Tyr Ala Ala Val Tyr Ser Val Ala Gln Ala Leu His Asn Thr Leu Gln
            405                 410                 415

Cys Asn Val Ser His Cys His Thr Ser Glu Pro Val Gln Pro Trp Gln
        420                 425                 430

Leu Leu Glu Asn Met Tyr Asn Met Ser Phe Arg Ala Arg Asp Leu Thr
    435                 440                 445

Leu Gln Phe Asp Ala Lys Gly Ser Val Asp Met Glu Tyr Asp Leu Lys
450                 455                 460

Met Trp Val Trp Gln Ser Pro Thr Pro Val Leu His Thr Val Gly Thr
465                 470                 475                 480

Phe Asn Gly Thr Leu Gln Leu Gln His Ser Lys Met Tyr Trp Pro Gly
            485                 490                 495
```

```
Asn Gln Val Pro Val Ser Gln Cys Ser Arg Gln Cys Lys Asp Gly Gln
            500                 505                 510

Val Arg Arg Val Lys Gly Phe His Ser Cys Cys Tyr Asp Cys Val Asp
            515                 520                 525

Cys Lys Ala Gly Ser Tyr Arg Lys His Pro Asp Asp Phe Thr Cys Thr
    530                 535                 540

Pro Cys Gly Lys Asp Gln Trp Ser Pro Glu Lys Ser Thr Thr Cys Leu
545                 550                 555                 560

Pro Arg Arg Pro Lys Phe Leu Ala Trp Gly Glu Pro Ala Val Leu Ser
                565                 570                 575

Leu Leu Leu Leu Leu Cys Leu Val Leu Gly Leu Thr Leu Ala Ala Leu
            580                 585                 590

Gly Leu Phe Val His Tyr Trp Asp Ser Pro Leu Val Gln Ala Ser Gly
            595                 600                 605

Gly Ser Leu Phe Cys Phe Gly Leu Ile Cys Leu Gly Leu Phe Cys Leu
    610                 615                 620

Ser Val Leu Leu Phe Pro Gly Arg Pro Arg Ser Ala Ser Cys Leu Ala
625                 630                 635                 640

Gln Gln Pro Met Ala His Leu Pro Leu Thr Gly Cys Leu Ser Thr Leu
                645                 650                 655

Phe Leu Gln Ala Ala Glu Ile Phe Val Glu Ser Glu Leu Pro Leu Ser
            660                 665                 670

Trp Ala Asn Trp Leu Cys Ser Tyr Leu Arg Gly Pro Trp Ala Trp Leu
            675                 680                 685

Val Val Leu Leu Ala Thr Leu Val Glu Ala Ala Leu Cys Ala Trp Tyr
    690                 695                 700

Leu Met Ala Phe Pro Pro Glu Val Val Thr Asp Trp Gln Val Leu Pro
705                 710                 715                 720

Thr Glu Val Leu Glu His Cys Arg Met Arg Ser Trp Val Ser Leu Gly
                725                 730                 735

Leu Val His Ile Thr Asn Ala Val Leu Ala Phe Leu Cys Phe Leu Gly
            740                 745                 750

Thr Phe Leu Val Gln Ser Gln Pro Gly Arg Tyr Asn Arg Ala Arg Gly
            755                 760                 765

Leu Thr Phe Ala Met Leu Ala Tyr Phe Ile Ile Trp Val Ser Phe Val
    770                 775                 780

Pro Leu Leu Ala Asn Val Gln Val Ala Tyr Gln Pro Ala Val Gln Met
785                 790                 795                 800

Gly Ala Ile Leu Phe Cys Ala Leu Gly Ile Leu Ala Thr Phe His Leu
                805                 810                 815

Pro Lys Cys Tyr Val Leu Leu Trp Leu Pro Glu Leu Asn Thr Gln Glu
            820                 825                 830

Phe Phe Leu Gly Arg Ser Pro Lys Glu Ala Ser Asp Gly Asn Ser Gly
            835                 840                 845

Ser Ser Glu Ala Thr Arg Gly His Ser Glu
    850                 855
```

MAMMALIAN SWEET TASTE RECEPTORS

CROSS-REFERENCES TO RELATED APPLICATIONS

The present application is a continuation of U.S. patent application Ser. No. 09/927,315, filed Aug. 10, 2001 and now issued U.S. Pat. No. 7,402,400, which claims priority to U.S. Ser. No. 60/302,898, filed Jul. 3, 2001, herein incorporated by reference in its entirety.

The present application is related to U.S. Ser. No. 60/095,464, filed Jul. 28, 1998; U.S. Ser. No. 60/112,747, filed Dec. 17, 1998; U.S. Ser. No. 09/361,631, filed Jul. 27, 1999; U.S. Ser. No. 60/094,465, and filed Jul. 28, 1998; U.S. Ser. No. 09/361,652, filed Jul. 27, 1000, herein each incorporated by reference in its entirety.

STATEMENT AS TO RIGHTS TO INVENTIONS MADE UNDER FEDERALLY SPONSORED RESEARCH AND DEVELOPMENT

The U.S. Government has certain rights in this invention pursuant to Grant Nos. DC03160 awarded by the National Institute on Deafness and Other Communication Disorders.

FIELD OF THE INVENTION

The sense of taste provides animals with valuable information about the quality and nutritional value of food. Previously, we identified a large family of mammalian taste receptors involved in bitter taste perception (the T2Rs). We now report the characterization of mammalian sweet taste receptors. First, transgenic rescue experiments prove that the Sac locus encodes T1R3, a member of the T1R family of candidate taste receptors. Second, using a heterologous expression system, we demonstrate that T1R2 and T1R3, when expressed in the same cell, function as a sweet receptor, recognizing sweet tasting molecules as diverse as sucrose, saccharin, dulcin and acesulfame-K. The T1R family therefore forms sweet receptors comprising polypeptides such as T1R2 and T1R3, and T1R1 and T1R3. Finally, we present a detailed analysis of the patterns of expression of T1Rs and T2Rs, thus providing a view of the representation of sweet and bitter taste at the periphery.

BACKGROUND OF THE INVENTION

Our sense of taste is capable of detecting and responding to sweet, bitter, sour, salty and umami stimuli (reviewed by Lindemann, 1996). It is also responsible for distinguishing between these various taste modalities, for instance, the sweetness of honey from the bitterness of tonic water; the sourness of unripe fruit from the saltiness of the ocean. This discriminatory power provides valuable sensory input: bitter receptors elicit aversive behavioral reactions to noxious substances, while sweet receptors allow recognition of high caloric food sources.

We have been interested in basic questions of taste signal detection and information coding, and have focused on the isolation and characterization of genes encoding sweet and bitter taste receptors. The identification of taste receptors generates powerful molecular tools to investigate not only the function of taste receptor cells, but also the logic of taste coding. For example, defining the size and diversity of the receptor repertoire provide evidence for how a large number of chemosensory ligands may be recognized (i.e., molecular diversity), while analysis of the patterns of receptor expression contributes important insight to our understanding of chemosensory discrimination and coding. Recently, we described the isolation of two novel families of G-protein coupled receptors (GPCRs) expressed in subsets of taste receptor cells of the tongue and palate (T1Rs and T2Rs; Hoon et al., 1999; Adler et al., 2000). One of these, the T2Rs, is a family of ~30 different genes that include several functionally validated mammalian bitter taste receptors (Adler et al., 2000; Chandrashekar et al., 2000; Matsunami et al., 2000). Nearly all of the T2R-genes are clustered in regions of the genome that have been genetically implicated in controlling responses to diverse bitter tastants in humans and mice, consistent with their proposed role as bitter taste receptors (Adler et al., 2000).

Notably, most T2Rs are co-expressed in the same subset of taste receptor cells (Adler et al., 2000), suggesting that these cells are capable of responding to a broad array of bitter compounds, but not discriminating between them. This is logical for a sensory modality like bitter, in which the animal needs to recognize and react to many noxious tastants, but not necessarily discriminate between them (i.e., we need to know that a tastant is bad news, but not necessarily what makes it bad). This interpretation is consistent with behavioral and psychophysical findings in rodents and humans demonstrating limited discrimination between various bitter tastants (McBurney and Gent, 1979).

How is sweet taste specified? There is considerable evidence that G-protein coupled receptors are also involved in this taste modality (Lindemann, 1996). In contrast to bitter taste, the number of biologically relevant sweet tastants is modest. Thus, we might expect the sweet receptor family to be quite small. Interestingly, psychophysical, behavioral and electrophysiological studies suggest that animals distinguish between various sweet tastants (Schiffman et al., 1981; Ninomiya et al., 1984; Ninomiya et al., 1997), perhaps reflecting (and predicting) the organization of the sweet taste system into distinct types of sweet receptor cells and pathways.

Genetic studies of sweet tasting have identified a single principal locus in mice influencing responses to several sweet substances (Fuller, 1974; Lush, 1989). This locus, named Sac, determines threshold differences in the ability of some strains to distinguish saccharin-containing solutions from water (Fuller, 1974). Sac tasters respond to ~5-fold lower concentrations of saccharin than "sweet-insensitive" Sac non-taster mice (Fuller, 1974; Capeless and Whitney, 1995); additionally, Sac influences preferences to sucrose, acesulfame-K and dulcin (Lush, 1989). Recently, several groups reported that a T1R-related gene, T1R3, might encode Sac (Kitagawa et al., 2001; Max et al., 2001; Montmayeur et al., 2001; Sainz et al., 2001).

We now demonstrate that transgenic expression of T1R3 from a taster strain transforms sweet-insensitive animals to tasters, affirming T1R3 as the Sac gene. We then developed a cell-based reporter system to prove that T1Rs encode functional sweet taste receptors. Lastly, we show that the patterns of T1R expression define at least three distinct cell types, and that sweet and bitter receptors are tightly segregated at the periphery.

BRIEF SUMMARY OF THE INVENTION

The present invention thus provides for the first time a sweet taste receptor comprising a T1R3 polypeptide. The present invention provides sweet taste receptor comprising a T1R3 polypeptide and a heterologous member of the T1R family, e.g., T1R1 or T1R2, that transduces a signal in response to sweet taste ligands when T1R3 and either T1R1 or T1R2 are co-expressed in the same cell. In one embodiment, the T1R3 polypeptide and the heterologous T1R polypeptide form a heterodimer. In another embodiment, the T1R3 polypeptide and the heterologous T1R polypeptide are non-covalently linked. In another embodiment, the T1R3 polypeptide and the heterologous T1R polypeptide are covalently linked.

In one aspect, the present invention provides an sweet taste receptor comprising a T1R3 polypeptide, the T1R3 polypeptide comprising greater than about 70% amino acid sequence identity to an amino acid sequence of SEQ ID NO: 15, SEQ ID NO:20, SEQ ID NO:23, or SEQ ID NO:25, or encoded by a nucleotide sequence hybridizing under moderately or highly stringent hybridization conditions to a nucleotide sequence encoding an amino acid sequence of SEQ ID NO:15, SEQ ID NO:20, SEQ ID NO:23, or SEQ ID NO:25.

In one embodiment, the receptor specifically binds to polyclonal antibodies generated against SEQ ID NO:15, SEQ ID NO:20, SEQ ID NO:23, or SEQ ID NO:25. In another embodiment, the receptor has G-protein coupled receptor activity. In another embodiment, the T1R3 polypeptide has an amino acid sequence of SEQ ID NO:15, SEQ ID NO:20, SEQ ID NO:23, or SEQ ID NO:25. In another embodiment, the receptor is from a human, a rat, or a mouse.

In one aspect, the present invention provides a sweet taste receptor, the receptor comprising a T1R3 polypeptide and a heterologous polypeptide, the T1R3 polypeptide comprising greater than about 70% amino acid sequence identity to an amino acid sequence of SEQ ID NO: 15, SEQ ID NO:20, SEQ ID NO:23, or SEQ ID NO:25, or encoded by a nucleotide sequence hybridizing under moderately or highly stringent hybridization conditions to a nucleotide sequence encoding an amino acid sequence of SEQ ID NO:15, SEQ ID NO:20, SEQ ID NO:23, or SEQ ID NO:25.

In one embodiment, the heterologous polypeptide is a T1R family member. In another embodiment, the heterologous polypeptide is T1R1 or T1R2. In one embodiment, the T1R1 polypeptide is encoded by a nucleotide sequence that hybridizes under moderately or highly stringent conditions to a nucleotide sequence encoding SEQ ID NO: 1, 2, or 3. In one embodiment, the T1R2 polypeptide is encoded by a nucleotide sequence that hybridizes under moderately or highly stringent conditions to a nucleotide sequence encoding SEQ ID NO:7, 8, or 9. In one embodiment, the receptor specifically binds to polyclonal antibodies generated against SEQ ID NO:15, SEQ ID NO:20, SEQ ID NO:23, or SEQ ID NO:25. In another embodiment, the receptor has G-protein coupled receptor activity. In another embodiment, the T1R3 polypeptide has an amino acid sequence of SEQ ID NO:15, SEQ ID NO:20, SEQ ID NO:23, or SEQ ID NO:25. In another embodiment, the receptor is from a human, a rat, or a mouse.

In one embodiment, the T1R3 polypeptide and the T1R polypeptide form a heterodimer. In one embodiment, the T1R3 polypeptide and the T1R heterologous polypeptide are non-covalently linked. In another embodiment, the T1R3 polypeptide and the T1R heterologous polypeptide are covalently linked.

In one aspect, the present invention provides an isolated polypeptide comprising an extracellular, a transmembrane domain, or a cytoplasmic domain of a sweet taste receptor, the extracellular, a transmembrane domain, or a cytoplasmic domain comprising greater than about 70% amino acid sequence identity to the extracellular, a transmembrane domain, or a cytoplasmic domain of SEQ ID NO:15, SEQ ID NO:20, SEQ ID NO:23, or SEQ ID NO:25. In another embodiment, the extracellular, transmembrane, or cytoplasmic domain hybridize under moderately or highly stringent conditions to an extracellular, transmembrane, or cytoplasmic domain of SEQ ID NO: 15, 20, 23, or 25.

In one embodiment, the polypeptide encodes the extracellular, a transmembrane domain, or a cytoplasmic domain of SEQ ID NO:15, SEQ ID NO:20, SEQ ID NO:23, or SEQ ID NO:25. In another embodiment, the extracellular, a transmembrane domain, or a cytoplasmic domain is covalently linked to a heterologous polypeptide, forming a chimeric polypeptide. In another embodiment, the chimeric polypeptide has G-protein coupled receptor activity.

In one aspect, the present invention provides an antibody that selectively binds to a sweet taste receptor, the receptor comprising a T1R3 polypeptide and a heterologous polypeptide, the antibody raised against a receptor comprising a T1R3 polypeptide comprising greater than about 70% amino acid sequence identity to an amino acid sequence of SEQ ID NO: 15, SEQ ID NO:20, SEQ ID NO:23, or SEQ ID NO:25, or encoded by a nucleotide sequence hybridizing under highly or moderately stringent hybridization conditions to a nucleotide sequence encoding an amino acid sequence of SEQ ID NO:15, SEQ ID NO:20, SEQ ID NO:23, or SEQ ID NO:25. In one embodiment, the T1R3 polypeptide forms a heterodimeric receptor, either by covalent or non-covalent linkage, with a T1R polypeptide, to which the antibody specifically binds.

In another aspect, the present invention provides a method for identifying a compound that modulates sweet taste signaling in taste cells, the method comprising the steps of: (i) contacting the compound with a sweet receptor comprising a T1R3 polypeptide, the polypeptide comprising greater than about 70% amino acid sequence identity to the extracellular domain of SEQ ID NO: 15, SEQ ID NO:20, SEQ ID NO:23, or SEQ ID NO:25; or encoded by a nucleotide sequence hybridizing under moderately or highly stringent hybridization conditions to a nucleotide sequence encoding an amino acid sequence of SEQ ID NO:15, SEQ ID NO:20, SEQ ID NO:23, or SEQ ID NO:25; and (ii) determining the functional effect of the compound upon the receptor.

In one embodiment, the receptor comprises T1R3, is heterodimeric receptor, and is linked to a heterologous polypeptide either covalently or non-covalently. In another embodiment, the receptor comprises T1R1 and T1R3. In another embodiment, the receptor comprises T1R2 and T1R3. In another embodiment, the polypeptide has G-protein coupled receptor activity. In another embodiment, the functional effect is determined in vitro. In another embodiment, the receptor is linked to a solid phase, either covalently or non-covalently. In another embodiment, the functional effect is determined by measuring changes in intracellular cAMP, IP3, or Ca2+. In another embodiment, the functional effect is a chemical or phenotypic effect. In another embodiment, the functional effect is a physical effect. In another embodiment, the functional effect is determined by measuring binding of the compound to the extracellular domain of the receptor. In another embodiment, the polypeptide is recombinant. In another embodiment, the polypeptide is expressed in a cell or cell membrane. In another embodiment, the cell is a eukaryotic cell, e.g., a mammalian cell, e.g., a human cell.

In one aspect, the present invention provides an isolated nucleic acid encoding a T1R3 polypeptide, the polypeptide comprising greater than about 70% amino acid identity to an amino acid sequence of SEQ ID NO:15, SEQ ID NO:20, SEQ ID NO:23, or SEQ ID NO:25.

In one embodiment, the nucleic acid comprises a nucleotide sequence of SEQ ID NO:14, SEQ ID NO:19, SEQ ID NO:22, or SEQ ID NO:24. In another embodiment, the nucleic acid is amplified by primers that selectively hybridize under stringent hybridization conditions to SEQ ID NO:14, SEQ ID NO:19, SEQ ID NO:22, or SEQ ID NO:24.

In another aspect, the present invention provides an isolated nucleic acid encoding a T1R3 polypeptide, wherein the nucleic acid specifically hybridizes under moderately or highly stringent conditions to a nucleic acid encoding SEQ ID NO: 15, SEQ ID NO:20, SEQ ID NO:23, or SEQ ID NO:25 or having the sequence of SEQ ID NO:14, SEQ ID NO:19, SEQ ID NO:22, or SEQ ID NO:24.

In another aspect, the present invention provides an isolated nucleic acid encoding a T1R3 polypeptide, the polypeptide comprising greater than about 70% amino acid identity to a polypeptide having a sequence of SEQ ID NO:15, SEQ ID NO:20, SEQ ID NO:23, or SEQ ID NO:25, wherein the nucleic acid selectively hybridizes under moderately stringent hybridization conditions to a nucleotide sequence of SEQ ID NO:14, SEQ ID NO:19, SEQ ID NO:22, or SEQ ID NO:24.

In another aspect, the present invention provides an isolated nucleic acid encoding an extracellular domain, a transmembrane domain, or a cytoplasmic domain of a T1R3 polypeptide, the extracellular domain, a transmembrane domain, or a cytoplasmic domain having greater than about 70% amino acid sequence identity to the extracellular domain, a transmembrane domain, or a cytoplasmic domain of SEQ ID NO:15, SEQ ID NO:20, SEQ ID NO:23, or SEQ ID NO:25.

In another aspect, the present invention provides an expression vector comprising a nucleic acid encoding a polypeptide comprising greater than about 70% amino acid sequence identity to an amino acid sequence of SEQ ID NO:15, SEQ ID NO:20, SEQ ID NO:23, or SEQ ID NO:25. In another aspect, the present invention provides a host cell transfected with the expression vector.

DETAILED DESCRIPTION

Introduction

Figure 1:
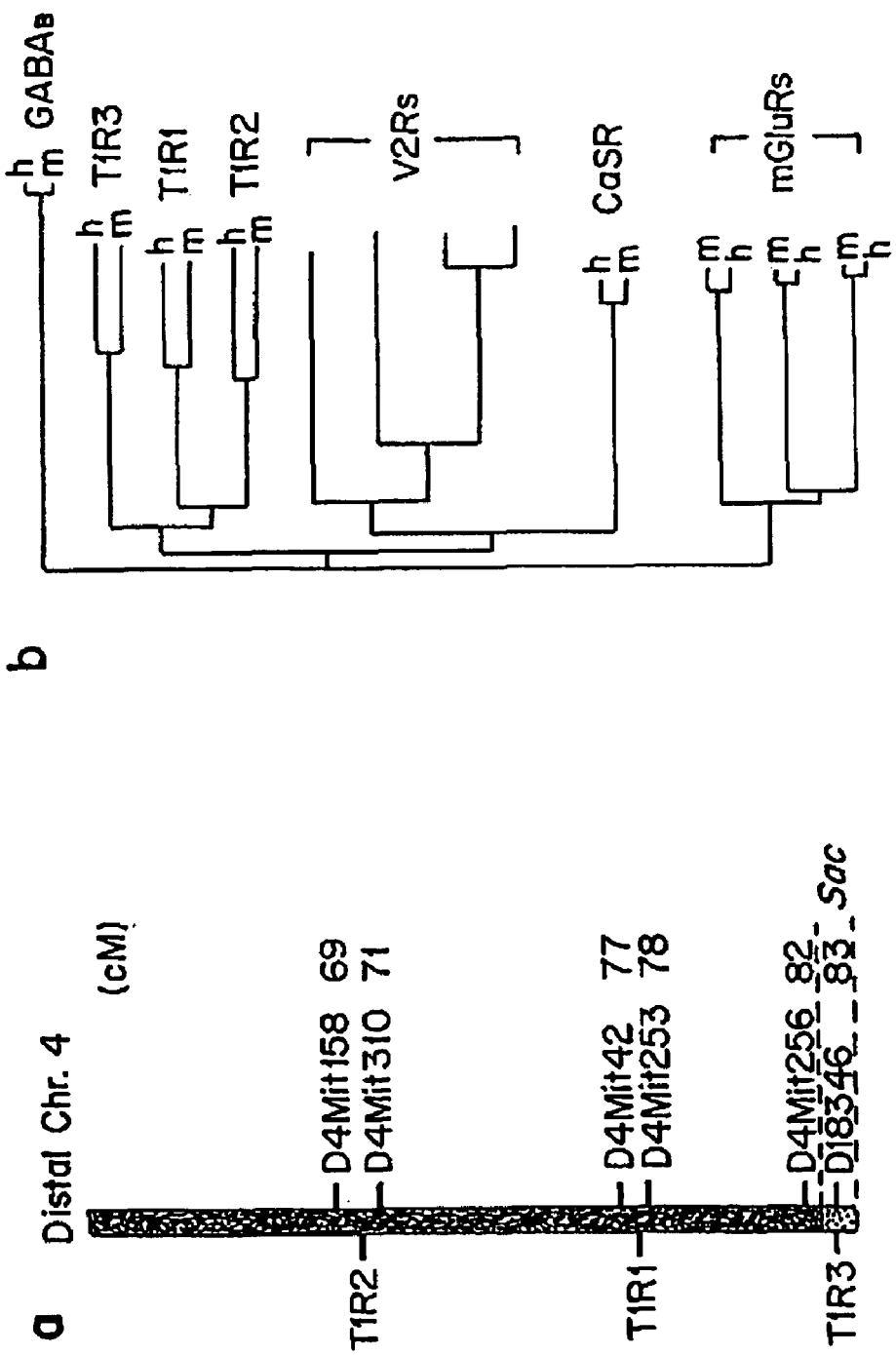
FIG. 1. T1R3 maps to the Sac locus
(a) Radiation hybrid and STS mapping localized all three T1R genes to the distal end of chromosome 4. The T1R3 gene is closely linked to D18346, an STS marker within the Sac genetic interval (Kitagawa et al, 2001; Li et al., 2001; Max et al., 2001; Montmayeur et al., 2001; Sainz et al., 2001). (b) Cladogram showing sequence similarity between human (h) and mouse (m) T1Rs and related receptors (Nakanishi, 1992; Brown et al., 1993; Herrada and Dulac, 1997; Matsunami and Buck, 1997; Ryba and Tirindelli, 1997; Kaupmann et al, 1997; Hoon et al, 1999); mouse V2Rs do not have human counterparts.

The present invention provides sweet taste receptors comprising members of the T1R family of G-protein coupled receptors. In a preferred embodiment, the present invention provides sweet taste receptor comprising a T1R3 polypeptide and a second, heterologous T1R polypeptide, e.g., T1R1 or T1R2. These sweet taste receptors are GPCR components of the taste transduction pathway, and when co-expressed in the same cell, the polypeptides transduce signal in response to sweet taste ligand.

These nucleic acids and proteins encoding the receptors provide valuable probes for the identification of taste cells, as the nucleic acids are specifically expressed in taste cells. For example, probes for GPCR polypeptides and proteins can be used to identity subsets of taste cells such as foliate cells, palate cells, and circumvallate cells, or specific taste receptor cells, e.g., sweet taste receptor cells. As described below, T1R1 and T1R3, and T1R2 and T1R3 are co-expressed in specific taste receptor cell subsets. They also serve as tools for the generation of taste topographic maps that elucidate the relationship between the taste cells of the tongue and taste sensory neurons leading to taste centers in the brain. Furthermore, the nucleic acids and the proteins they encode can be used as probes to dissect taste-induced behaviors.

The invention also provides methods of screening for modulators, e.g., activators, inhibitors, stimulators, enhancers, agonists, and antagonists, of these novel sweet taste receptors comprising T1R3 and another member of the T1R family such as T1R1 or T1R2. Such modulators of sweet taste transduction are useful for pharmacological and genetic modulation of sweet taste signaling pathways, and for the discovery of novel sweet taste ligands. These methods of screening can be used to identify high affinity agonists and antagonists of sweet taste cell activity. These modulatory compounds can then be used in the food and pharmaceutical industries to customize taste. Thus, the invention provides assays for taste modulation, where the T1R3-comprising receptor acts as an direct or indirect reporter molecule for the effect of modulators on sweet taste transduction. GPCRs can be used in assays, e.g., to measure changes in ligand binding, G-protein binding, regulatory molecule binding, ion concentration, membrane potential, current flow, ion flux, transcription, signal transduction, receptor-ligand interactions, neurotransmitter and hormone release; and second messenger concentrations, in vitro, in vivo, and ex vivo. In one embodiment, a receptor comprising T1R3 can be used as an indirect reporter via attachment to a second reporter molecule such as green fluorescent protein (see, e.g., Mistili & Spector, *Nature Biotechnology* 15:961-964 (1997)). In another embodiment, a receptor comprising T1R3 is recombinantly expressed in cells, and modulation of taste transduction via GPCR activity is assayed by measuring changes in Ca2+ levels.

Methods of assaying for modulators of taste transduction include in vitro ligand binding assays using receptors comprising T1R3, portions thereof such as the extracellular domain, or chimeric proteins comprising one or more domains of T1R3, and in in vivo (cell-based and animal) assays such as oocyte T1R3 receptor expression; tissue culture cell T1R3 receptor expression; transcriptional activation of T1R3; phosphorylation and dephosphorylation of GPCRs; G-protein binding to GPCRs; ligand binding assays; voltage, membrane potential and conductance changes; ion flux assays; changes in intracellular second messengers such as cAMP and inositol triphosphate; changes in intracellular calcium levels; and neurotransmitter release.

DEFINITIONS

A "T1R family taste receptor" refers to a receptor comprising a member of the T1R family of G-protein coupled receptors, e.g., T1R1, T1R2, and T1R3, or any combination thereof. In one embodiment, the T1R family receptor comprises T1R3 (a "T1R3-comprising taste receptor" or a "T1R3-comprising sweet taste receptor") and a heterologous polypeptide of the T1R family. In one embodiment, the receptor comprises T1R1 and T1R3. In another embodiment, the receptor comprises T1R2 and T1R3. In one embodiment, the T1R3-comprising receptor is active when the two members of the receptor are co-expressed in the same cell, e.g., T1R1 and T1R3 or T1R2 and T1R3. In another embodiment, the T1R polypeptides are co-expressed in the same cell and form a heterodimeric receptor, in which the T1R polypeptides of the receptor are non-covalently linked or covalently linked. The receptor has the ability to recognize a sweet tasting molecule such as sucrose, saccharin, dulcin, acesulfame-K, as well as other molecules, sweet and non-sweet, as described herein. These molecules are examples of compounds that "modulate sweet taste signal transduction" by acting as ligands for the sweet G protein coupled receptor comprising T1R3.

The terms "GPCR-B3 or T1R1," "GPCR-B4 or T1R2," and "T1R3" or a nucleic acid encoding "GPCR-B3 or T1R1," "GPCR-B4 or T1R2," and "T1R3" refer to nucleic acid and polypeptide polymorphic variants, alleles, mutants, and interspecies homologs that are members of the T1R family of G protein coupled receptors and: (1) have an amino acid sequence that has greater than about 60% amino acid sequence identity, 65%, 70%, 75%, 80%, 85%, 90%, preferably 91%, 92%, 93%, 94%, 95%, 96%, 97%, 98% or 99% or greater amino acid sequence identity, preferably over a region of over a region of at least about 25, 50, 100, 200, 500, 1000, or more amino acids, to an amino acid sequence encoded by SEQ ID NO:1, 2, 3, 7, 8, 9, 15, 18, 20, 23, or 25; (2) bind to antibodies, e.g., polyclonal antibodies, raised against an immunogen comprising an amino acid sequence encoded by SEQ ID NO:1, 2, 3, 7, 8, 9, 15, 18, 20, 23, or 25, and conservatively modified variants thereof, (3) specifically hybridize under stringent hybridization conditions to an anti-sense strand corresponding to a nucleic acid sequence encoding a T1R protein, e.g., SEQ ID NO:4, 5, 6, 10, 11, 12, 13, 14, 16, 17, 19, 21, 22, or 24, and conservatively modified variants thereof, (4) have a nucleic acid sequence that has greater than about 60% sequence identity, 65%, 70%, 75%, 80%, 85%, 90%, preferably 91%, 92%, 93%, 94%, 95%, 96%, 97%, 98% or 99%, or higher nucleotide sequence identity, preferably over a region of at least about 25, 50, 100, 200, 500, 1000, or more nucleotides, to SEQ ID NO:4, 5, 6, 10, 11, 12, 13, 14, 16, 17, 19, 21, 22, or 24. The T1R family polypeptide of the invention (e.g., T1R1, T1R2, or T1R3) or T1R3-comprising receptor further has G protein coupled receptor activity, either alone or when co-expressed in the same cell, or when co-expressed as a heterodimer with another T1R family member. Accession numbers for amino acid sequences and nucleotide sequences of T1R1, T1R2, and T1R3 can be found in GenBank.

T1R proteins have "G-protein coupled receptor activity," e.g., they bind to G-proteins in response to extracellular stimuli, such as ligand binding, and promote production of second messengers such as IP3, cAMP, and Ca2+ via stimulation of enzymes such as phospholipase C and adenylate cyclase. Such activity can be measured in a heterologous cell, by coupling a GPCR (or a chimeric GPCR) to either a G-protein or promiscuous G-protein such as Gα15, and an enzyme such as PLC, and measuring increases in intracellular calcium using (Offermans & Simon, *J. Biol. Chem.* 270:15175-15180 (1995)). Receptor activity can be effectively measured, e.g., by recording ligand-induced changes in [$Ca^{2+}$]i using fluorescent $Ca^{2+}$-indicator dyes and fluorometric imaging.

Such GPCRs have transmembrane, extracellular and cytoplasmic domains that can be structurally identified using methods known to those of skill in the art, such as sequence analysis programs that identify hydrophobic and hydrophilic domains (see, e.g., Kyte & Doolittle, *J. Mol. Biol.* 157:105-132 (1982)). Such domains are useful for making chimeric proteins and for in vitro assays of the invention (see, e.g., WO 94/05695 and U.S. Pat. No. 5,508,384).

The phrase "functional effects" in the context of assays for testing compounds that modulate activity (e.g., signal transduction) of a sweet taste receptor or protein of the invention includes the determination of a parameter that is indirectly or directly under the influence of a GPCR or sweet taste receptor, e.g., a physical, phenotypic, or chemical effect, such as the ability to transduce a cellular signal in response to external stimuli such as ligand binding, or the ability to bind a ligand. It includes binding activity and signal transduction. "Functional effects" include in vitro, in vivo, and ex vivo activities.

By "determining the functional effect" is meant assaying for a compound that increases or decreases a parameter that is indirectly or directly under the influence of a T1R GPCR protein or a sweet taste receptor comprising one or more T1R GPCR proteins, e.g., physical (direct) and chemical or phenotypic (indirect) effects. Such functional effects can be measured by any means known to those skilled in the art, e.g., changes in spectroscopic characteristics (e.g., fluorescence, absorbance, refractive index); hydrodynamic (e.g., shape); chromatographic; or solubility properties for the protein; measuring inducible markers or transcriptional activation of the protein; measuring binding activity or binding assays, e.g., binding to antibodies; measuring changes in ligand binding activity or analogs thereof, either naturally occurring or synthetic; measuring cellular proliferation; measuring cell surface marker expression, measurement of changes in protein levels for T1R-associated sequences; measurement of RNA stability; G-protein binding; GPCR phosphorylation or dephosphorylation; signal transduction, e.g., receptor-ligand interactions, second messenger concentrations (e.g., cAMP, cGMP, IP3, PI, or intracellular $Ca^{2+}$); neurotransmitter release; hormone release; voltage, membrane potential and conductance changes; ion flux; regulatory molecule binding; identification of downstream or reporter gene expression (CAT, luciferase, β-gal, GFP and the like), e.g., via chemiluminescence, fluorescence, colorimetric reactions, antibody binding, and inducible markers.

"Inhibitors," "activators," and "modulators" of T1R family polynucleotide and polypeptide sequences and T1R family sweet receptors are used to refer to activating, inhibitory, or modulating molecules identified using in vitro and in vivo assays of T1R polynucleotide and polypeptide sequences and T1R family sweet receptors, including heterodimeric receptors. Inhibitors are compounds that, e.g., bind to, partially or totally block activity, decrease, prevent, delay activation, inactivate, desensitize, or down regulate the activity or expression of T1R family sweet receptors such as a receptor comprising a T1R3 polypeptide, e.g., antagonists. "Activators" are compounds that increase, open, activate, facilitate, enhance activation, sensitize, agonize, or up regulate a T1R family sweet receptor, such as a receptor comprising a T1R3 polypeptide, e.g., agonists. Inhibitors, activators, or modulators also include genetically modified versions of T1R family sweet receptors, e.g., versions with altered activity, as well as naturally occurring and synthetic ligands, antagonists, agonists, antibodies, antisense molecules, ribozymes, small chemical molecules and the like. Such assays for inhibitors and activators include, e.g., expressing T1R family sweet receptors in vitro, in cells, or cell membranes, applying putative modulator compounds, and then determining the functional effects on activity, as described above. The sweet taste receptor comprising a T1R3 polypeptide has the ability to recognize a sweet tasting molecule such as sucrose, saccharin, dulcin, acesulfame-K, and other molecules, as described herein. These molecules are examples of compounds that modulate sweet taste signal transduction by acting as extracellular ligands for the sweet G protein coupled receptor and activating the receptor. In other embodiments, compounds that modulate sweet taste signal transduction are molecules that act as intracellular ligands of the receptor, or inhibit or activate binding of an extracellular ligand, or inhibit or activate binding of intracellular ligands of the receptor.

Samples or assays comprising T1R family sweet receptors that are treated with a potential activator, inhibitor, or modulator are compared to control samples without the inhibitor, activator, or modulator to examine the extent of inhibition. Control samples (untreated with inhibitors) are assigned a relative protein activity value of 100%. Inhibition of a T1R family sweet receptor is achieved when the activity value relative to the control is about 80%, preferably 50%, more preferably 25-0%. Activation of a T1R family sweet receptor is achieved when the activity value relative to the control (untreated with activators) is 110%, more preferably 150%, more preferably 200-500% (i.e., two to five fold higher relative to the control), more preferably 1000-3000% higher.

The term "test compound" or "drug candidate" or "modulator" or grammatical equivalents as used herein describes any molecule, either naturally occurring or synthetic, e.g., protein, oligopeptide (e.g., from about 5 to about 25 amino acids in length, preferably from about 10 to 20 or 12 to 18 amino acids in length, preferably 12, 15, or 18 amino acids in length), small organic molecule, polysaccharide, lipid (e.g., a sphingolipid), fatty acid, polynucleotide, oligonucleotide, etc., to be tested for the capacity to directly or indirectly modulation taste. The test compound can be in the form of a library of test compounds, such as a combinatorial or randomized library that provides a sufficient range of diversity. Test compounds are optionally linked to a fusion partner, e.g., targeting compounds, rescue compounds, dimerization compounds, stabilizing compounds, addressable compounds, and other functional moieties. Conventionally, new chemical entities with useful properties are generated by identifying a test compound (called a "lead compound") with some desirable property or activity, e.g., inhibiting activity, creating variants of the lead compound, and evaluating the property and activity of those variant compounds. Often, high throughput screening (HTS) methods are employed for such an analysis.

A "small organic molecule" refers to an organic molecule, either naturally occurring or synthetic, that has a molecular weight of more than about 50 daltons and less than about 2500 daltons, preferably less than about 2000 daltons, preferably between about 100 to about 1000 daltons, more preferably between about 200 to about 500 daltons.

"Biological sample" include sections of tissues such as biopsy and autopsy samples, and frozen sections taken for histologic purposes. Such samples include blood, sputum, tissue, cultured cells, e.g., primary cultures, explants, and transformed cells, stool, urine, etc. A biological sample is typically obtained from a eukaryotic organism, most preferably a mammal such as a primate e.g., chimpanzee or human; cow; dog; cat; a rodent, e.g., guinea pig, rat, mouse; rabbit; or a bird; reptile; or fish.

A "heterodimer" is a dimer comprising two different molecules, e.g., two different polypeptides, where the molecules are associated via either covalent, e.g., through a linker or a chemical bond, or non-covalent, e.g., ionic, van der Waals, electrostatic, or hydrogen bonds linkages. The T1R2-comprising receptors of the invention function when co-expressed in the same cell, or optionally when co-expressed so that they form a heterodimer, either covalently or non-covalently linked.

The terms "identical" or percent "identity," in the context of two or more nucleic acids or polypeptide sequences, refer to two or more sequences or subsequences that are the same or have a specified percentage of amino acid residues or nucleotides that are the same (i.e., about 60% identity, preferably 65%, 70%, 75%, 80%, 85%, 90%, 91%, 92%, 93%, 94%, 95%, 96%, 97%, 98%, 99%, or higher identity over a specified region (e.g., nucleotide sequences SEQ ID NO:1-25), when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the compliment of a test sequence. The definition also includes sequences that have deletions and/or additions, as well as those that have substitutions. As described below, the preferred algorithms can account for gaps and the like. Preferably, identity exists over a region that is at least about 25 amino acids or nucleotides in length, or more preferably over a region that is 50-100 amino acids or nucleotides in length.

For sequence comparison, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

A "comparison window", as used herein, includes reference to a segment of any one of the number of contiguous positions selected from the group consisting of from 20 to 600, usually about 50 to about 200, more usually about 100 to about 150 in which a sequence may be compared to a reference sequence of the same number of contiguous positions after the two sequences are optimally aligned. Methods of alignment of sequences for comparison are well-known in the art. Optimal alignment of sequences for comparison can be conducted, e.g., by the local homology algorithm of Smith & Waterman, $Adv. Appl. Math.$ 2:482 (1981), by the homology alignment algorithm of Needleman & Wunsch, $J. Mol. Biol.$ 48:443 (1970), by the search for similarity method of Pearson & Lipman, $Proc. Nat'l. Acad. Sci. USA$ 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by manual alignment and visual inspection (see, e.g., $Current Protocols in Molecular Biology$ (Ausubel et al., eds. 1995 supplement)).

A preferred example of algorithm that is suitable for determining percent sequence identity and sequence similarity are the BLAST and BLAST 2.0 algorithms, which are described in Altschul et al., $Nuc. Acids Res.$ 25:3389-3402 (1977) and Altschul et al., $J. Mol. Biol.$ 215:403-410 (1990), respectively. BLAST and BLAST 2.0 are used, with the parameters described herein, to determine percent sequence identity for the nucleic acids and proteins of the invention. Software for performing BLAST analyses is publicly available through the National Center for Biotechnology Information. This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4 and a comparison of both strands. For amino acid sequences, the BLASTP program uses as defaults a wordlength of 3, and expectation (E) of 10, and the BLOSUM62 scoring matrix (see Henikoff & Henikoff, $Proc. Natl. Acad. Sci. USA$ 89:10915 (1989)) alignments (B) of 50, expectation (E) of 10, M=5, N=−4, and a comparison of both strands.

The terms "polypeptide," "peptide," and "protein" are used interchangeably herein to refer to a polymer of amino acid residues. The terms apply to amino acid polymers in which one or more amino acid residue is an artificial chemical mimetic of a corresponding naturally occurring amino acid, as well as to naturally occurring amino acid polymers and non-naturally occurring amino acid polymer.

The term "amino acid" refers to naturally occurring and synthetic amino acids, as well as amino acid analogs and amino acid mimetics that function in a manner similar to the naturally occurring amino acids. Naturally occurring amino acids are those encoded by the genetic code, as well as those amino acids that are later modified, e.g., hydroxyproline, γ-carboxyglutamate, and O-phosphoserine. Amino acid analogs refers to compounds that have the same basic chemical structure as a naturally occurring amino acid, i.e., an a carbon that is bound to a hydrogen, a carboxyl group, an amino group, and an R group, e.g., homoserine, norleucine, methionine sulfoxide, methionine methyl sulfonium. Such analogs have modified R groups (e.g., norleucine) or modified peptide backbones, but retain the same basic chemical structure as a naturally occurring amino acid. Amino acid mimetics refers to chemical compounds that have a structure that is different from the general chemical structure of an amino acid, but that functions in a manner similar to a naturally occurring amino acid.

Amino acids may be referred to herein by either their commonly known three letter symbols or by the one-letter symbols recommended by the IUPAC-IUB Biochemical Nomenclature Commission. Nucleotides, likewise, may be referred to by their commonly accepted single-letter codes.

"Conservatively modified variants" applies to both amino acid and nucleic acid sequences. With respect to particular nucleic acid sequences, conservatively modified variants refers to those nucleic acids which encode identical or essentially identical amino acid sequences, or where the nucleic acid does not encode an amino acid sequence, to essentially identical sequences. Because of the degeneracy of the genetic code, a large number of functionally identical nucleic acids encode any given protein. For instance, the codons GCA, GCC, GCG and GCU all encode the amino acid alanine. Thus, at every position where an alanine is specified by a codon, the codon can be altered to any of the corresponding codons described without altering the encoded polypeptide. Such nucleic acid variations are "silent variations," which are one species of conservatively modified variations. Every nucleic acid sequence herein which encodes a polypeptide also describes every possible silent variation of the nucleic acid. One of skill will recognize that each codon in a nucleic acid (except AUG, which is ordinarily the only codon for methionine, and TGG, which is ordinarily the only codon for tryptophan) can be modified to yield a functionally identical molecule. Accordingly, each silent variation of a nucleic acid which encodes a polypeptide is implicit in each described sequence with respect to the expression product, but not with respect to actual probe sequences.

As to amino acid sequences, one of skill will recognize that individual substitutions, deletions or additions to a nucleic acid, peptide, polypeptide, or protein sequence which alters, adds or deletes a single amino acid or a small percentage of amino acids in the encoded sequence is a "conservatively modified variant" where the alteration results in the substitution of an amino acid with a chemically similar amino acid. Conservative substitution tables providing functionally similar amino acids are well known in the art. Such conservatively modified variants are in addition to and do not exclude polymorphic variants, interspecies homologs, and alleles of the invention.

The following eight groups each contain amino acids that are conservative substitutions for one another: 1) Alanine (A), Glycine (G); 2) Aspartic acid (D), Glutamic acid (E); 3) Asparagine (N), Glutamine (Q); 4) Arginine (R), Lysine (K); 5) Isoleucine (I), Leucine (L), Methionine (M), Valine (V); 6) Phenylalanine (F), Tyrosine (Y), Tryptophan (W); 7) Serine (S), Threonine (T); and 8) Cysteine (C), Methionine (M) (see, e.g., Creighton, *Proteins* (1984)).

Macromolecular structures such as polypeptide structures can be described in terms of various levels of organization. For a general discussion of this organization, see, e.g., Alberts et al., *Molecular Biology of the Cell* ($3^{rd}$ ed., 1994) and Cantor and Schimmel, *Biophysical Chemistry Part I: The Conformation of Biological Macromolecules* (1980). "Primary structure" refers to the amino acid sequence of a particular peptide. "Secondary structure" refers to locally ordered, three dimensional structures within a polypeptide. These structures are commonly known as domains, e.g., extracellular domains, transmembrane domains, and cytoplasmic domains. Domains are portions of a polypeptide that form a compact unit of the polypeptide and are typically 15 to 350 amino acids long. Typical domains are made up of sections of lesser organization such as stretches of β-sheet and α-helices. "Tertiary structure" refers to the complete three dimensional structure of a polypeptide monomer. "Quaternary structure" refers to the three dimensional structure formed by the noncovalent association of independent tertiary units. Anisotropic terms are also known as energy terms.

A particular nucleic acid sequence also implicitly encompasses "splice variants." Similarly, a particular protein encoded by a nucleic acid implicitly encompasses any protein encoded by a splice variant of that nucleic acid. "Splice variants," as the name suggests, are products of alternative splicing of a gene. After transcription, an initial nucleic acid transcript may be spliced such that different (alternate) nucleic acid splice products encode different polypeptides. Mechanisms for the production of splice variants vary, but include alternate splicing of exons. Alternate polypeptides derived from the same nucleic acid by read-through transcription are also encompassed by this definition. Any products of a splicing reaction, including recombinant forms of the splice products, are included in this definition.

A "label" or a "detectable moiety" is a composition detectable by spectroscopic, photochemical, biochemical, immunochemical, chemical, or other physical means. For example, useful labels include $^{32}$P, fluorescent dyes, electron-dense reagents, enzymes (e.g., as commonly used in an ELISA), biotin, digoxigenin, or haptens and proteins which can be made detectable, e.g., by incorporating a radiolabel into the peptide or used to detect antibodies specifically reactive with the peptide.

The term "recombinant" when used with reference, e.g., to a cell, or nucleic acid, protein, or vector, indicates that the cell, nucleic acid, protein or vector, has been modified by the introduction of a heterologous nucleic acid or protein or the alteration of a native nucleic acid or protein, or that the cell is derived from a cell so modified. Thus, for example, recombinant cells express genes that are not found within the native (non-recombinant) form of the cell or express native genes that are otherwise abnormally expressed, under expressed or not expressed at all.

The term "heterologous" when used with reference to portions of a nucleic acid indicates that the nucleic acid comprises two or more subsequences that are not found in the same relationship to each other in nature. For instance, the nucleic acid is typically recombinantly produced, having two or more sequences from unrelated genes arranged to make a new functional nucleic acid, e.g., a promoter from one source and a coding region from another source. Similarly, a heterologous protein indicates that the protein comprises two or more subsequences that are not found in the same relationship to each other in nature (e.g., a fusion protein).

The phrase "stringent hybridization conditions" refers to conditions under which a probe will hybridize to its target subsequence, typically in a complex mixture of nucleic acids, but to no other sequences. Stringent conditions are sequence-dependent and will be different in different circumstances. Longer sequences hybridize specifically at higher temperatures. An extensive guide to the hybridization of nucleic acids is found in Tijssen, *Techniques in Biochemistry and Molecular Biology—Hybridization with Nucleic Probes*, "Overview of principles of hybridization and the strategy of nucleic acid assays" (1993). Generally, stringent conditions are selected to be about 5-10° C. lower than the thermal melting point ($T_m$) for the specific sequence at a defined ionic strength pH. The $T_m$ is the temperature (under defined ionic strength, pH, and nucleic concentration) at which 50% of the probes complementary to the target hybridize to the target sequence at equilibrium (as the target sequences are present in excess, at $T_m$, 50% of the probes are occupied at equilibrium). Stringent conditions may also be achieved with the addition of destabilizing agents such as formamide. For selective or specific hybridization, a positive signal is at least two times background, preferably 10 times background hybridization. Exemplary stringent hybridization conditions can be as following: 50% formamide, 5×SSC, and 1% SDS, incubating at 42° C., or, 5×SSC, 1% SDS, incubating at 65° C., with wash in 0.2×SSC, and 0.1% SDS at 65° C.

Nucleic acids that do not hybridize to each other under stringent conditions are still substantially identical if the polypeptides which they encode are substantially identical. This occurs, for example, when a copy of a nucleic acid is created using the maximum codon degeneracy permitted by the genetic code. In such cases, the nucleic acids typically hybridize under moderately stringent hybridization conditions. Exemplary "moderately stringent hybridization conditions" include a hybridization in a buffer of 40% formamide, 1 M NaCl, 1% SDS at 37° C., and a wash in 1×SSC at 45° C. A positive hybridization is at least twice background. Those of ordinary skill will readily recognize that alternative hybridization and wash conditions can be utilized to provide conditions of similar stringency. Additional guidelines for determining hybridization parameters are provided in numerous reference, e.g., and *Current Protocols in Molecular Biology*, ed. Ausubel, et al.

For PCR, a temperature of about 36° C. is typical for low stringency amplification, although annealing temperatures may vary between about 32° C. and 48° C. depending on primer length. For high stringency PCR amplification, a temperature of about 62° C. is typical, although high stringency annealing temperatures can range from about 50° C. to about 65° C., depending on the primer length and specificity. Typical cycle conditions for both high and low stringency amplifications include a denaturation phase of 90° C.-95° C. for 30 sec-2 min., an annealing phase lasting 30 sec.-2 min., and an extension phase of about 72° C. for 1-2 min. Protocols and guidelines for low and high stringency amplification reactions are provided, e.g., in Innis et al., *PCR Protocols, A Guide to Methods and Applications* (1990).

"Antibody" refers to a polypeptide comprising a framework region from an immunoglobulin gene or fragments thereof that specifically binds and recognizes an antigen. The recognized immunoglobulin genes include the kappa, lambda, alpha, gamma, delta, epsilon, and mu constant region genes, as well as the myriad immunoglobulin variable region genes. Light chains are classified as either kappa or lambda. Heavy chains are classified as gamma, mu, alpha, delta, or epsilon, which in turn define the immunoglobulin classes, IgG, IgM, IgA, IgD and IgE, respectively. Typically, the antigen-binding region of an antibody will be most critical in specificity and affinity of binding.

An exemplary immunoglobulin (antibody) structural unit comprises a tetramer. Each tetramer is composed of two identical pairs of polypeptide chains, each pair having one "light" (about 25 kD) and one "heavy" chain (about 50-70 kD). The N-terminus of each chain defines a variable region of about 100 to 110 or more amino acids primarily responsible for antigen recognition. The terms variable light chain ($V_L$) and variable heavy chain ($V_H$) refer to these light and heavy chains respectively.

Antibodies exist, e.g., as intact immunoglobulins or as a number of well-characterized fragments produced by digestion with various peptidases. Thus, for example, pepsin digests an antibody below the disulfide linkages in the hinge region to produce F(ab)'$_2$, a dimer of Fab which itself is a light chain joined to $V_H$-$C_H$1 by a disulfide bond. The F(ab)'$_2$ may be reduced under mild conditions to break the disulfide linkage in the hinge region, thereby converting the F(ab)'$_2$ dimer into an Fab' monomer. The Fab' monomer is essentially Fab with part of the hinge region (see *Fundamental Immunology* (Paul ed., 3d ed. 1993). While various antibody fragments are defined in terms of the digestion of an intact antibody, one of skill will appreciate that such fragments may be synthesized de novo either chemically or by using recombinant DNA methodology. Thus, the term antibody, as used herein, also includes antibody fragments either produced by the modification of whole antibodies, or those synthesized de novo using recombinant DNA methodologies (e.g., single chain Fv) or those identified using phage display libraries (see, e.g., McCafferty et al., *Nature* 348:552-554 (1990))

For preparation of antibodies, e.g., recombinant, monoclonal, or polyclonal antibodies, many technique known in the art can be used (see, e.g., Kohler & Milstein, *Nature* 256:495-497 (1975); Kozbor et al., *Immunology Today* 4: 72 (1983); Cole et al., pp. 77-96 in *Monoclonal Antibodies and Cancer Therapy*, Alan R. Liss, Inc. (1985); Coligan, *Current Protocols in Immunology* (1991); Harlow & Lane, *Antibodies, A Laboratory Manual* (1988); and Goding, *Monoclonal Antibodies: Principles and Practice* (2d ed. 1986)). Techniques for the production of single chain antibodies (U.S. Pat. No. 4,946,778) can be adapted to produce antibodies to polypeptides of this invention. Also, transgenic mice, or other organisms such as other mammals, may be used to express humanized antibodies. Alternatively, phage display technology can be used to identify antibodies and heteromeric Fab fragments that specifically bind to selected antigens (see, e.g., McCafferty et al, *Nature* 348:552-554 (1990); Marks et al., *Biotechnology* 10:779-783 (1992)).

A "chimeric antibody" is an antibody molecule in which (a) the constant region, or a portion thereof, is altered, replaced or exchanged so that the antigen binding site (variable region) is linked to a constant region of a different or altered class, effector function and/or species, or an entirely different molecule which confers new properties to the chimeric antibody, e.g., an enzyme, toxin, hormone, growth factor, drug, etc.; or (b) the variable region, or a portion thereof, is altered, replaced or exchanged with a variable region having a different or altered antigen specificity.

In one embodiment, the antibody is conjugated to an "effector" moiety. The effector moiety can be any number of molecules, including labeling moieties such as radioactive labels or fluorescent labels, or can be a therapeutic moiety. In one aspect the antibody modulates the activity of the protein.

The phrase "specifically (or selectively) binds" to an antibody or "specifically (or selectively) immunoreactive with," when referring to a protein or peptide, refers to a binding reaction that is determinative of the presence of the protein, often in a heterogeneous population of proteins and other biologics. Thus, under designated immunoassay conditions, the specified antibodies bind to a particular protein at least two times the background and more typically more than 10 to 100 times background. Specific binding to an antibody under such conditions requires an antibody that is selected for its specificity for a particular protein. For example, polyclonal antibodies raised to a T1R protein or a heterodimeric T1R3-comprising sweet taste receptor comprising a sequence of or encoded by SEQ ID NO:1-25, polymorphic variants, alleles, orthologs, and conservatively modified variants, or splice variants, or portions thereof, can be selected to obtain only those polyclonal antibodies that are specifically immunoreactive with T1R proteins and/or heterodimeric T1R3-comprising sweet taste receptors and not with other proteins. In one embodiment, the antibodies react with a heterodimeric T1R3-comprising taste receptor, but not with individual protein members of the T1R family. This selection may be achieved by subtracting out antibodies that cross-react with other molecules. A variety of immunoassay formats may be used to select antibodies specifically immunoreactive with a particular protein. For example, solid-phase ELISA immunoassays are routinely used to select antibodies specifically immunoreactive with a protein (see, e.g., Harlow & Lane, *Antibodies, A Laboratory Manual* (1988) for a description of immunoassay formats and conditions that can be used to determine specific immunoreactivity).

Isolation of Nucleic Acids Encoding T1R Family Members

This invention relies on routine techniques in the field of recombinant genetics. Basic texts disclosing the general methods of use in this invention include Sambrook et al., *Molecular Cloning, A Laboratory Manual* (2nd ed. 1989); Kriegler, *Gene Transfer and Expression: A Laboratory Manual* (1990); and *Current Protocols in Molecular Biology* (Ausubel et al., eds., 1994)).

T1R nucleic acids, polymorphic variants, orthologs, and alleles that are substantially identical to an amino acid sequences disclosed herein can be isolated using T1R nucleic acid probes and oligonucleotides under stringent hybridization conditions, by screening libraries. Alternatively, expression libraries can be used to clone T1R protein, polymorphic variants, orthologs, and alleles by detecting expressed homologs immunologically with antisera or purified antibodies made against human T1R or portions thereof.

To make a cDNA library, one should choose a source that is rich in T1R RNA, e.g., taste buds such as circumvallate, foliate, fungiform, and palate. The mRNA is then made into cDNA using reverse transcriptase, ligated into a recombinant vector, and transfected into a recombinant host for propagation, screening and cloning. Methods for making and screening cDNA libraries are well known (see, e.g., Gubler & Hoffman, *Gene* 25:263-269 (1983); Sambrook et al., supra; Ausubel et al., supra).

For a genomic library, the DNA is extracted from the tissue and either mechanically sheared or enzymatically digested to yield fragments of about 12-20 kb. The fragments are then separated by gradient centrifugation from undesired sizes and are constructed in bacteriophage lambda vectors. These vectors and phage are packaged in vitro. Recombinant phage are analyzed by plaque hybridization as described in Benton & Davis, *Science* 196:180-182 (1977). Colony hybridization is carried out as generally described in Grunstein et al., *Proc. Natl. Acad. Sci. USA.,* 72:3961-3965 (1975).

An alternative method of isolating T1R nucleic acid and its orthologs, alleles, mutants, polymorphic variants, and conservatively modified variants combines the use of synthetic oligonucleotide primers and amplification of an RNA or DNA template (see U.S. Pat. Nos. 4,683,195 and 4,683,202; *PCR Protocols: A Guide to Methods and Applications* (Innis et al., eds, 1990)). Methods such as polymerase chain reaction (PCR) and ligase chain reaction (LCR) can be used to amplify nucleic acid sequences of human T1R directly from mRNA, from cDNA, from genomic libraries or cDNA libraries. Degenerate oligonucleotides can be designed to amplify TR homologs using the sequences provided herein. Restriction endonuclease sites can be incorporated into the primers. Polymerase chain reaction or other in vitro amplification methods may also be useful, for example, to clone nucleic acid sequences that code for proteins to be expressed, to make nucleic acids to use as probes for detecting the presence of T1R encoding mRNA in physiological samples, for nucleic acid sequencing, or for other purposes. Genes amplified by the PCR reaction can be purified from agarose gels and cloned into an appropriate vector.

Gene expression of T1R can also be analyzed by techniques known in the art, e.g., reverse transcription and amplification of mRNA, isolation of total RNA or poly $A^+$ RNA, northern blotting, dot blotting, in situ hybridization, RNase protection, high density polynucleotide array technology, e.g., and the like.

Nucleic acids encoding T1R protein can be used with high density oligonucleotide array technology (e.g., GeneChip™) to identify T1R protein, orthologs, alleles, conservatively modified variants, and polymorphic variants in this invention (see, e.g., Gunthand et al., *AIDS Res. Hum. Retroviruses* 14: 869-876 (1998); Kozal et al., *Nat. Med.* 2:753-759 (1996); Matson et al., *Anal Biochem.* 224:110-106 (1995); Lockhart et al., *Nat. Biotechnol.* 14:1675-1680 (1996); Gingeras et al., *Genome Res.* 8:435-448 (1998); Hacia et al., *Nucleic Acids Res.* 26:3865-3866 (1998)).

The gene for T1R is typically cloned into intermediate vectors before transformation into prokaryotic or eukaryotic cells for replication and/or expression. These intermediate vectors are typically prokaryote vectors, e.g., plasmids, or shuttle vectors.

Expression in Prokaryotes and Eukaryotes

To obtain high level expression of a cloned gene, such as those cDNAs encoding a T1R protein, one typically subclones T1R into an expression vector that contains a strong promoter to direct transcription, a transcription/translation terminator, and if for a nucleic acid encoding a protein, a ribosome binding site for translational initiation. The T1R nucleic acids can be co-expressed or separately expressed, preferably co-expressed on the same or a different vector. Suitable bacterial promoters are well known in the art and described, e.g., in Sambrook et al., and Ausubel et al, supra. Bacterial expression systems for expressing the T1R protein are available in, e.g., *E. coli, Bacillus* sp., and *Salmonella* (Palva et al., *Gene* 22:229-235 (1983); Mosbach et al., *Nature* 302:543-545 (1983). Kits for such expression systems are commercially available. Eukaryotic expression systems for mammalian cells, yeast, and insect cells are well known in the art and are also commercially available. In one preferred embodiment, retroviral expression systems are used in the present invention.

Selection of the promoter used to direct expression of a heterologous nucleic acid depends on the particular application. The promoter is preferably positioned about the same distance from the heterologous transcription start site as it is from the transcription start site in its natural setting. As is known in the art, however, some variation in this distance can be accommodated without loss of promoter function.

In addition to the promoter, the expression vector typically contains a transcription unit or expression cassette that contains all the additional elements required for the expression of the T1R encoding nucleic acid in host cells. A typical expression cassette thus contains a promoter operably linked to the nucleic acid sequence encoding T1R and signals required for efficient polyadenylation of the transcript, ribosome binding sites, and translation termination. Additional elements of the cassette may include enhancers and, if genomic DNA is used as the structural gene, introns with functional splice donor and acceptor sites.

In addition to a promoter sequence, the expression cassette should also contain a transcription termination region downstream of the structural gene to provide for efficient termination. The termination region may be obtained from the same gene as the promoter sequence or may be obtained from different genes.

The particular expression vector used to transport the genetic information into the cell is not particularly critical. Any of the conventional vectors used for expression in eukaryotic or prokaryotic cells may be used. Standard bacterial expression vectors include plasmids such as pBR322 based plasmids, pSKF, pET23D, and fusion expression systems such as MBP, GST, and LacZ. Epitope tags can also be added to recombinant proteins to provide convenient methods of isolation, e.g., c-myc. Sequence tags may be included in an expression cassette for nucleic acid rescue. Markers such as fluorescent proteins, green or red fluorescent protein, β-gal, CAT, and the like can be included in the vectors as markers for vector transduction.

Expression vectors containing regulatory elements from eukaryotic viruses are typically used in eukaryotic expression vectors, e.g., SV40 vectors, papilloma virus vectors, retroviral vectors, and vectors derived from Epstein-Barr virus. Other exemplary eukaryotic vectors include pMSG, pAV009/A+, pMTO10/A+, pMAMneo-5, baculovirus pDSVE, and any other vector allowing expression of proteins under the direction of the CMV promoter, SV40 early promoter, SV40 later promoter, metallothionein promoter, murine mammary tumor virus promoter, Rous sarcoma virus promoter, polyhedrin promoter, or other promoters shown effective for expression in eukaryotic cells.

Expression of proteins from eukaryotic vectors can be also be regulated using inducible promoters. With inducible promoters, expression levels are tied to the concentration of inducing agents, such as tetracycline or ecdysone, by the incorporation of response elements for these agents into the promoter. Generally, high level expression is obtained from inducible promoters only in the presence of the inducing agent; basal expression levels are minimal.

In one embodiment, the vectors of the invention have a regulatable promoter, e.g., tet-regulated systems and the RU-486 system (see, e.g., Gossen & Bujard, *Proc. Nat'l Acad. Sci. USA* 89:5547 (1992); Oligino et al., *Gene Ther.* 5:491-496 (1998); Wang et al., *Gene Ther.* 4:432-441 (1997); Neering et al., *Blood* 88:1147-1155 (1996); and Rendahl et al., *Nat. Biotechnol.* 16:757-761 (1998)). These impart small molecule control on the expression of the candidate target nucleic acids. This beneficial feature can be used to determine that a desired phenotype is caused by a transfected cDNA rather than a somatic mutation.

Some expression systems have markers that provide gene amplification such as thymidine kinase and dihydrofolate reductase. Alternatively, high yield expression systems not involving gene amplification are also suitable, such as using a baculovirus vector in insect cells, with a T1R encoding sequence under the direction of the polyhedrin promoter or other strong baculovirus promoters.

The elements that are typically included in expression vectors also include a replicon that functions in *E. coli*, a gene encoding antibiotic resistance to permit selection of bacteria that harbor recombinant plasmids, and unique restriction sites in nonessential regions of the plasmid to allow insertion of eukaryotic sequences. The particular antibiotic resistance gene chosen is not critical, any of the many resistance genes known in the art are suitable. The prokaryotic sequences are preferably chosen such that they do not interfere with the replication of the DNA in eukaryotic cells, if necessary.

Standard transfection methods are used to produce bacterial, mammalian, yeast or insect cell lines that express large quantities of T1R protein, which are then purified using standard techniques (see, e.g., Colley et al., *J. Biol. Chem.* 264: 17619-17622 (1989); *Guide to Protein Purification*, in *Methods in Enzymology*, vol. 182 (Deutscher, ed., 1990)). Transformation of eukaryotic and prokaryotic cells are performed according to standard techniques (see, e.g., Morrison, *J. Bact.* 132:349-351 (1977); Clark-Curtiss & Curtiss, *Methods in Enzymology* 101:347-362 (Wu et al., eds, 1983).

Any of the well-known procedures for introducing foreign nucleotide sequences into host cells may be used. These include the use of calcium phosphate transfection, polybrene, protoplast fusion, electroporation, biolistics, liposomes, microinjection, plasma vectors, viral vectors and any of the other well known methods for introducing cloned genomic DNA, cDNA, synthetic DNA or other foreign genetic material into a host cell (see, e.g., Sambrook et al., supra). It is only necessary that the particular genetic engineering procedure used be capable of successfully introducing at least one gene into the host cell capable of expressing T1R.

After the expression vector is introduced into the cells, the transfected cells are cultured under conditions favoring expression of T1R, which is recovered from the culture using standard techniques identified below.

Purification of T1R Polypeptides

Either naturally occurring or recombinant T1R polypeptides or T1R3-comprising receptors can be purified for use in functional assays. Naturally occurring T1R proteins or T1R3-comprising receptors can be purified, e.g., from human tissue. Recombinant T1R proteins or T1R3-comprising receptors can be purified from any suitable expression system. T1R polypeptides are typically co-expressed in the same cell to form T1R3-comprising receptors.

The T1R protein or T1R3-comprising receptor may be purified to substantial purity by standard techniques, including selective precipitation with such substances as ammonium sulfate; column chromatography, immunopurification methods, and others (see, e.g., Scopes, *Protein Purification: Principles and Practice* (1982); U.S. Pat. No. 4,673,641; Ausubel et al., supra; and Sambrook et al., supra).

A number of procedures can be employed when recombinant T1R protein or T1R3-comprising receptor is being purified. For example, proteins having established molecular adhesion properties can be reversible fused to the T1R protein or T1R3-comprising receptor. With the appropriate ligand, T1R protein or T1R3-comprising receptor can be selectively adsorbed to a purification column and then freed from the column in a relatively pure form. The fused protein is then removed by enzymatic activity. Finally, T1R protein or T1R3-comprising receptor could be purified using immunoaffinity columns.

A. Purification of T1R from Recombinant Bacteria

Recombinant proteins are expressed by transformed bacteria in large amounts, typically after promoter induction; but expression can be constitutive. Promoter induction with IPTG is one example of an inducible promoter system. Bacteria are grown according to standard procedures in the art. Fresh or frozen bacteria cells are used for isolation of protein.

Proteins expressed in bacteria may form insoluble aggregates ("inclusion bodies"). Several protocols are suitable for purification of T1R protein or T1R3-comprising receptor inclusion bodies. For example, purification of inclusion bodies typically involves the extraction, separation and/or purification of inclusion bodies by disruption of bacterial cells, e.g., by incubation in a buffer of 50 mM TRIS/HCL pH 7.5, 50 mM NaCl, 5 mM $MgCl_2$, 1 mM DTT, 0.1 mM ATP, and 1 mM PMSF. The cell suspension can be lysed using 2-3 passages through a French Press, homogenized using a Polytron (Brinkman Instruments) or sonicated on ice. Alternate methods of lysing bacteria are apparent to those of skill in the art (see, e.g., Sambrook et al., supra; Ausubel et al., supra).

If necessary, the inclusion bodies are solubilized, and the lysed cell suspension is typically centrifuged to remove unwanted insoluble matter. Proteins that formed the inclusion bodies may be renatured by dilution or dialysis with a compatible buffer. Suitable solvents include, but are not limited to urea (from about 4 M to about 8 M), formamide (at least about 80%, volume/volume basis), and guanidine hydrochloride (from about 4 M to about 8 M). Some solvents which are capable of solubilizing aggregate-forming proteins, for example SDS (sodium dodecyl sulfate), 70% formic acid, are inappropriate for use in this procedure due to the possibility of irreversible denaturation of the proteins, accompanied by a lack of immunogenicity and/or activity. Although guanidine hydrochloride and similar agents are denaturants, this denaturation is not irreversible and renaturation may occur upon removal (by dialysis, for example) or dilution of the denaturant, allowing re-formation of immunologically and/or biologically active protein. Other suitable buffers are known to those skilled in the art. Human T1R proteins or T1R3-comprising receptors are separated from other bacterial proteins by standard separation techniques, e.g., with Ni-NTA agarose resin.

Alternatively, it is possible to purify T1R protein or T1R3-comprising receptor from bacteria periplasm. After lysis of the bacteria, when the T1R protein or T1R3-comprising receptor is exported into the periplasm of the bacteria, the periplasmic fraction of the bacteria can be isolated by cold osmotic shock in addition to other methods known to skill in the art. To isolate recombinant proteins from the periplasm, the bacterial cells are centrifuged to form a pellet. The pellet is resuspended in a buffer containing 20% sucrose. To lyse the cells, the bacteria are centrifuged and the pellet is resuspended in ice-cold 5 mM $MgSO_4$ and kept in an ice bath for approximately 10 minutes. The cell suspension is centrifuged and the supernatant decanted and saved. The recombinant proteins present in the supernatant can be separated from the host proteins by standard separation techniques well known to those of skill in the art.

B. Standard Protein Separation Techniques for Purifying T1R Proteins

Solubility Fractionation

Often as an initial step, particularly if the protein mixture is complex, an initial salt fractionation can separate many of the unwanted host cell proteins (or proteins derived from the cell culture media) from the recombinant protein of interest. The preferred salt is ammonium sulfate. Ammonium sulfate precipitates proteins by effectively reducing the amount of water in the protein mixture. Proteins then precipitate on the basis of their solubility. The more hydrophobic a protein is, the more likely it is to precipitate at lower ammonium sulfate concentrations. A typical protocol includes adding saturated ammonium sulfate to a protein solution so that the resultant ammonium sulfate concentration is between 20-30%. This concentration will precipitate the most hydrophobic of proteins. The precipitate is then discarded (unless the protein of interest is hydrophobic) and ammonium sulfate is added to the supernatant to a concentration known to precipitate the protein of interest. The precipitate is then solubilized in buffer and the excess salt removed if necessary, either through dialysis or diafiltration. Other methods that rely on solubility of proteins, such as cold ethanol precipitation, are well known to those of skill in the art and can be used to fractionate complex protein mixtures.

Size Differential Filtration

The molecular weight of the T1R proteins or T1R3-comprising receptors can be used to isolate it from proteins of greater and lesser size using ultrafiltration through membranes of different pore size (for example, Amicon or Millipore membranes). As a first step, the protein mixture is ultrafiltered through a membrane with a pore size that has a lower molecular weight cut-off than the molecular weight of the protein of interest. The retentate of the ultrafiltration is then ultrafiltered against a membrane with a molecular cut off greater than the molecular weight of the protein of interest. The recombinant protein will pass through the membrane into the filtrate. The filtrate can then be chromatographed as described below.

Column Chromatography

The T1R proteins or T1R3-comprising receptors can also be separated from other proteins on the basis of its size, net surface charge, hydrophobicity, and affinity for ligands. In addition, antibodies raised against proteins can be conjugated to column matrices and the proteins immunopurified. All of these methods are well known in the art. It will be apparent to one of skill that chromatographic techniques can be performed at any scale and using equipment from many different manufacturers (e.g., Pharmacia Biotech).

Assays for Modulators of T1R Protein

A. Assays

Modulation of a T1R3-comprising sweet taste receptor, and corresponding modulation of taste, can be assessed using a variety of in vitro and in vivo assays. Such assays can be used to test for inhibitors and activators of T1R3-comprising sweet taste receptors, and, consequently, inhibitors and activators of taste. Such modulators of T1R3-comprising sweet taste receptors, which are involved in taste signal transduction. Modulators of T1R3-comprising sweet taste receptors are tested using either recombinant or naturally occurring T1R3-comprising sweet taste receptors, preferably human receptors.

Preferably, the T1R3-comprising sweet taste receptor will have a sequence as encoded by a sequence provided herein or a conservatively modified variant thereof. Alternatively, the T1R3-comprising sweet taste receptor of the assay will be derived from a eukaryote and include an amino acid subsequence having substantial amino acid sequence identity to the sequences provided herein or is encoded by a nucleotide sequence that hybridizes under stringent conditions (moderate or high) to a nucleotide sequence as described herein. Generally, the amino acid sequence identity will be at least 60%, preferably at least 65%, 70%, 75%, 80%, 85%, or 90%, most preferably at least 95%.

Measurement of sweet taste signal transduction or loss-of-sweet taste signal transduction phenotype on T1R3-comprising sweet taste receptor or cell expressing the T1R3-comprising sweet taste receptor, either recombinant or naturally occurring, can be performed using a variety of assays, in vitro, in vivo, and ex vivo, as described herein. A suitable physical, chemical or phenotypic change that affects activity or binding can be used to assess the influence of a test compound on the polypeptide of this invention. When the functional effects are determined using intact cells or animals, one can also measure a variety of effects such as, in the case of signal transduction, e.g., ligand binding, hormone release, transcriptional changes to both known and uncharacterized genetic markers (e.g., northern blots), changes in cell metabolism such as pH changes, and changes in intracellular second messengers such as $Ca^{2+}$, IP3, cGMP, or cAMP.

In Vitro Assays

Assays to identify compounds with T1R3-comprising sweet taste receptor modulating activity can be performed in vitro. Such assays can use a full length T1R3-comprising sweet taste receptor or a variant thereof, or a fragment of a T1R3-comprising sweet taste receptor, such as an extracellular domain, fused to a heterologous protein to form a chimera. Purified recombinant or naturally occurring T1R3-comprising sweet taste receptor can be used in the in vitro methods of the invention. In addition to purified T1R3-comprising sweet taste receptor, the recombinant or naturally occurring T1R3-comprising sweet taste receptor can be part of a cellular lysate or a cell membrane. As described below, the binding assay can be either solid state or soluble. Preferably, the protein or membrane is bound to a solid support, either covalently or non-covalently. Often, the in vitro assays of the invention are ligand binding or ligand affinity assays, either non-competitive or competitive (with known extracellular ligands as described herein, or with a known intracellular ligand GTP). Other in vitro assays include measuring changes in spectroscopic (e.g., fluorescence, absorbance, refractive index), hydrodynamic (e.g., shape), chromatographic, or solubility properties for the protein.

In one embodiment, a high throughput binding assay is performed in which the T1R3-comprising sweet taste receptor or chimera comprising a fragment thereof is contacted with a potential modulator and incubated for a suitable amount of time. In one embodiment, the potential modulator is bound to a solid support, and the T1R3-comprising sweet taste receptor is added. In another embodiment, the T1R3-comprising sweet taste receptor is bound to a solid support. A wide variety of modulators can be used, as described below, including small organic molecules, peptides, antibodies, and T1R3-comprising sweet taste receptor ligand analogs. A wide variety of assays can be used to identify T1R3-comprising sweet taste receptor-modulator binding, including labeled protein-protein binding assays, electrophoretic mobility shifts, immunoassays, enzymatic assays such as phosphorylation assays, and the like. In some cases, the binding of the candidate modulator is determined through the use of competitive binding assays, where interference with binding of a known ligand is measured in the presence of a potential modulator. Ligands for T1R3-comprising sweet taste receptors are provided herein. Either the modulator or the known ligand is bound first, and then the competitor is added. After the T1R3-comprising sweet taste receptor is washed, interference with binding, either of the potential modulator or of the known ligand, is determined. Often, either the potential modulator or the known ligand is labeled.

Cell-Based In Vivo Assays

In another embodiment, a T1R3-comprising sweet taste receptor is expressed in a cell (e.g., by co-expression two heterologous members of the T1R family such as T1R1 and T1R3 or T1R2 and T1R3), and functional, e.g., physical and chemical or phenotypic, changes are assayed to identify T1R3-comprising sweet taste receptor taste modulators. Cells expressing T1R3-comprising sweet taste receptor can also be used in binding assays. Any suitable functional effect can be measured, as described herein. For example, ligand binding, G-protein binding, and GPCR signal transduction, e.g., changes in intracellular $Ca^{2+}$ levels, are all suitable assays to identify potential modulators using a cell based system. Suitable cells for such cell based assays include both primary cells and cell lines, as described herein. The T1R3-comprising sweet taste receptor can be naturally occurring or recombinant. Also, as described above, chimeric T1R3-comprising sweet taste receptors with GPCR activity can be used in cell based assays. For example, the extracellular domain of an T1R protein can be fused to the transmembrane and/or cytoplasmic domain of a heterologous protein, preferably a heterologous GPCR. Such a chimeric GPCR would have GPCR activity and could be used in cell based assays of the invention.

In another embodiment, cellular T1R polypeptide levels are determined by measuring the level of protein or mRNA. The level of T1R protein or proteins related to T1R signal transduction are measured using immunoassays such as western blotting, ELISA and the like with an antibody that selectively binds to the T1R3-comprising sweet taste receptor or a fragment thereof. For measurement of mRNA, amplification, e.g., using PCR, LCR, or hybridization assays, e.g., northern hybridization, RNAse protection, dot blotting, are preferred. The level of protein or mRNA is detected using directly or indirectly labeled detection agents, e.g., fluorescently or radioactively labeled nucleic acids, radioactively or enzymatically labeled antibodies, and the like, as described herein.

Alternatively, T1R3-comprising receptor expression can be measured using a reporter gene system. Such a system can be devised using an T1R protein promoter operably linked to a reporter gene such as chloramphenicol acetyltransferase, firefly luciferase, bacterial luciferase, β-galactosidase and alkaline phosphatase. Furthermore, the protein of interest can be used as an indirect reporter via attachment to a second reporter such as red or green fluorescent protein (see, e.g., Mistili & Spector, *Nature Biotechnology* 15:961-964 (1997)). The reporter construct is typically transfected into a cell. After treatment with a potential modulator, the amount of reporter gene transcription, translation, or activity is measured according to standard techniques known to those of skill in the art.

In another embodiment, a functional effect related to GPCR signal transduction can be measured. An activated or inhibited T1R3-comprising G-coupled protein receptor will alter the properties of target enzymes, second messengers, channels, and other effector proteins. The examples include the activation of cGMP phosphodiesterase, adenylate cyclase, phospholipase C, IP3, and modulation of diverse channels by G proteins. Downstream consequences can also be examined such as generation of diacyl glycerol and IP3 by phospholipase C, and in turn, for calcium mobilization by IP3. Activated GPCR receptors become substrates for kinases that phosphorylate the C-terminal tail of the receptor (and possibly other sites as well). Thus, activators will promote the transfer of $^{32}P$ from gamma-labeled GTP to the receptor, which can be assayed with a scintillation counter. The phosphorylation of the C-terminal tail will promote the binding of arrestin-like proteins and will interfere with the binding of G-proteins. For a general review of GPCR signal transduction and methods of assaying signal transduction, see, e.g., *Methods in Enzymology*, vols. 237 and 238 (1994) and volume 96 (1983); Bourne et al., *Nature* 10:349:117-27 (1991); Bourne et al., *Nature* 348:125-32 (1990); Pitcher et al., *Annu. Rev. Biochem.* 67:653-92 (1998).

As described above, activation of some G-protein coupled receptors stimulates the formation of inositol triphosphate (IP3) through phospholipase C-mediated hydrolysis of phosphatidylinositol (Berridge & Irvine, *Nature* 312:315-21 (1984)). IP3 in turn stimulates the release of intracellular calcium ion stores. Thus, a change in cytoplasmic calcium ion levels, or a change in second messenger levels such as IP3 can be used to assess G-protein coupled receptor function. Cells expressing such G-protein coupled receptors may exhibit increased cytoplasmic calcium levels as a result of contribution from both intracellular stores and via activation of ion channels, in which case it may be desirable although not necessary to conduct such assays in calcium-free buffer, optionally supplemented with a chelating agent such as EGTA, to distinguish fluorescence response resulting from calcium release from internal stores.

In one example, T1R3-comprising sweet taste receptor GPCR activity is measured by expressing a T1R3-comprising sweet taste receptor in a heterologous cell with a promiscuous G-protein that links the receptor to a phospholipase C signal transduction pathway (see Offermanns & Simon, *J. Biol. Chem.* 270:15175-15180 (1995)). Modulation of signal transduction is assayed by measuring changes in intracellular $Ca^{2+}$ levels, which change in response to modulation of the GPCR signal transduction pathway via administration of a molecule that associates with an T1R3-comprising sweet taste receptor. Changes in $Ca^{2+}$ levels are optionally measured using fluorescent $Ca^{2+}$ indicator dyes and fluorometric imaging.

In another example, phosphatidyl inositol (PI) hydrolysis can be analyzed according to U.S. Pat. No. 5,436,128, herein incorporated by reference. Briefly, the assay involves labeling of cells with $^3H$-myoinositol for 48 or more hrs. The labeled cells are treated with a test compound for one hour. The treated cells are lysed and extracted in chloroform-methanol-water after which the inositol phosphates were separated by ion exchange chromatography and quantified by scintillation counting. Fold stimulation is determined by calculating the ratio of cpm in the presence of agonist to cpm in the presence of buffer control. Likewise, fold inhibition is determined by calculating the ratio of cpm in the presence of antagonist to cpm in the presence of buffer control (which may or may not contain an agonist).

Other assays can involve determining the activity of receptors which, when activated, result in a change in the level of intracellular cyclic nucleotides, e.g., cAMP or cGMP, by activating or inhibiting enzymes such as adenylate cyclase. In cases where activation of the receptor results in a decrease in cyclic nucleotide levels, it may be preferable to expose the cells to agents that increase intracellular cyclic nucleotide levels, e.g., forskolin, prior to adding a receptor-activating compound to the cells in the assay.

In one example, the changes in intracellular cAMP or cGMP can be measured using immunoassays. The method described in Offermanns & Simon, *J. Biol. Chem.* 270:15175-15180 (1995) may be used to determine the level of cAMP. Also, the method described in Felley-Bosco et al., *Am. J. Resp. Cell and Mol. Biol.* 11:159-164 (1994) may be used to determine the level of cGMP. Further, an assay kit for measuring cAMP and/or cGMP is described in U.S. Pat. No. 4,115,538, herein incorporated by reference.

In one example, assays for G-protein coupled receptor activity include cells that are loaded with ion or voltage sensitive dyes to report receptor activity. Assays for determining activity of such receptors can also use known agonists and antagonists for other G-protein coupled receptors as negative or positive controls to assess activity of tested compounds. In assays for identifying modulatory compounds (e.g., agonists, antagonists), changes in the level of ions in the cytoplasm or membrane voltage will be monitored using an ion sensitive or membrane voltage fluorescent indicator, respectively. Among the ion-sensitive indicators and voltage probes that may be employed are those disclosed in the Molecular Probes 1997 Catalog. For G-protein coupled receptors, promiscuous G-proteins such as $G\alpha 15$ and $G\alpha 16$ can be used in the assay of choice (Wilkie et al., *Proc. Nat'l Acad. Sci. USA* 88:10049-10053 (1991)). Such promiscuous G-proteins allow coupling of a wide range of receptors.

Animal Models

Animal models of taste also find use in screening for modulators of taste, such as the Sac taster and non-taster mouse strains as described herein. Similarly, transgenic animal technology including gene knockout technology, for example as a result of homologous recombination with an appropriate gene targeting vector, or gene overexpression, will result in the absence or increased expression of the T1R3-comprising receptor or components thereof. When desired, tissue-specific expression or knockout of the T1R3-comprising receptors or components thereof may be necessary. Transgenic animals generated by such methods find use as animal models of taste modulation and are additionally useful in screening for modulators of taste modulation.

B. Modulators

The compounds tested as modulators of T1R3-comprising sweet taste receptors can be any small organic molecule, or a biological entity, such as a protein, e.g., an antibody or peptide, a sugar, a nucleic acid, e.g., an antisense oligonucleotide or a ribozyme, or a lipid. Alternatively, modulators can be genetically altered versions of a T1R3-comprising sweet taste receptor. Typically, test compounds will be small organic molecules, peptides, lipids, and lipid analogs.

Essentially any chemical compound can be used as a potential modulator or ligand in the assays of the invention, although most often compounds can be dissolved in aqueous or organic (especially DMSO-based) solutions are used. The assays are designed to screen large chemical libraries by automating the assay steps and providing compounds from any convenient source to assays, which are typically run in parallel (e.g., in microtiter formats on microtiter plates in robotic assays). It will be appreciated that there are many suppliers of chemical compounds, including Sigma (St. Louis, Mo.), Aldrich (St. Louis, Mo.), Sigma-Aldrich (St. Louis, Mo.), Fluka Chemika-Biochemica Analytika (Buchs Switzerland) and the like.

In one preferred embodiment, high throughput screening methods involve providing a combinatorial small organic molecule or peptide library containing a large number of potential therapeutic compounds (potential modulator or ligand compounds). Such "combinatorial chemical libraries" or "ligand libraries" are then screened in one or more assays, as described herein, to identify those library members (particular chemical species or subclasses) that display a desired characteristic activity. The compounds thus identified can serve as conventional "lead compounds" or can themselves be used as potential or actual therapeutics.

A combinatorial chemical library is a collection of diverse chemical compounds generated by either chemical synthesis or biological synthesis, by combining a number of chemical "building blocks" such as reagents. For example, a linear combinatorial chemical library such as a polypeptide library is formed by combining a set of chemical building blocks (amino acids) in every possible way for a given compound length (i.e., the number of amino acids in a polypeptide compound). Millions of chemical compounds can be synthesized through such combinatorial mixing of chemical building blocks.

Preparation and screening of combinatorial chemical libraries is well known to those of skill in the art. Such combinatorial chemical libraries include, but are not limited to, peptide libraries (see, e.g., U.S. Pat. No. 5,010,175, Furka, *Int. J. Pept. Prot. Res.* 37:487-493 (1991) and Houghton et al., *Nature* 354:84-88 (1991)). Other chemistries for generating chemical diversity libraries can also be used. Such chemistries include, but are not limited to: peptoids (e.g., PCT Publication No. WO 91/19735), encoded peptides (e.g., PCT Publication No. WO 93/20242), random bio-oligomers (e.g., PCT Publication No. WO 92/00091), benzodiazepines (e.g., U.S. Pat. No. 5,288,514), diversomers such as hydantoins, benzodiazepines and dipeptides (Hobbs et al., *Proc. Nat. Acad. Sci. USA* 90:6909-6913 (1993)), vinylogous polypeptides (Hagihara et al., *J. Amer. Chem. Soc.* 114:6568 (1992)), nonpeptidal peptidomimetics with glucose scaffolding (Hirschmann et al., *J. Amer. Chem. Soc.* 114:9217-9218 (1992)), analogous organic syntheses of small compound libraries (Chen et al., *J. Amer. Chem. Soc.* 116:2661 (1994)), oligocarbamates (Cho et al., *Science* 261:1303 (1993)), and/or peptidyl phosphonates (Campbell et al., *J. Org. Chem.* 59:658 (1994)), nucleic acid libraries (see Ausubel, Berger and Sambrook, all supra), peptide nucleic acid libraries (see, e.g., U.S. Pat. No. 5,539,083), antibody libraries (see, e.g., Vaughn et al., *Nature Biotechnology*, 14(3):309-314 (1996) and PCT/US96/10287), carbohydrate libraries (see, e.g., Liang et al., *Science*, 274:1520-1522 (1996) and U.S. Pat. No. 5,593,853), small organic molecule libraries (see, e.g., benzodiazepines, Baum C&EN, January 18, page 33 (1993); isoprenoids, U.S. Pat. No. 5,569,588; thiazolidinones and metathiazanones, U.S. Pat. No. 5,549,974; pyrrolidines, U.S. Pat. Nos. 5,525,735 and 5,519,134; morpholino compounds, U.S. Pat. No. 5,506,337; benzodiazepines, U.S. Pat. No. 5,288,514, and the like).

Devices for the preparation of combinatorial libraries are commercially available (see, e.g., 357 MPS, 390 MPS, Advanced Chem Tech, Louisville Ky., Symphony, Rainin, Woburn, Mass., 433A Applied Biosystems, Foster City, Calif., 9050 Plus, Millipore, Bedford, Mass.). In addition, numerous combinatorial libraries are themselves commercially available (see, e.g., ComGenex, Princeton, N.J., Asinex, Moscow, Ru, Tripos, Inc., St. Louis, Mo., ChemStar, Ltd, Moscow, RU, 3D Pharmaceuticals, Exton, Pa., Martek Biosciences, Columbia, Md., etc.).

C. Solid State and Soluble High Throughput Assays

In one embodiment the invention provides soluble assays using a T1R3-comprising sweet taste receptor, or a cell or tissue expressing a T1R3-comprising sweet taste receptor, either naturally occurring or recombinant. In another embodiment, the invention provides solid phase based in vitro assays in a high throughput format, where the T1R3-comprising sweet taste receptor is attached to a solid phase substrate. Any one of the assays described herein can be adapted for high throughput screening, e.g., ligand binding, cellular proliferation, cell surface marker flux, e.g., screening, radiolabeled GTP binding, second messenger flux, e.g., $Ca^{2+}$, IP3, cGMP, or cAMP, cytokine production, etc.

In the high throughput assays of the invention, either soluble or solid state, it is possible to screen up to several thousand different modulators or ligands in a single day. This methodology can be used for T1R3-comprising sweet taste receptors in vitro, or for cell-based or membrane-based assays comprising T1R3-comprising sweet taste receptors. In particular, each well of a microtiter plate can be used to run a separate assay against a selected potential modulator, or, if concentration or incubation time effects are to be observed, every 5-10 wells can test a single modulator. Thus, a single standard microtiter plate can assay about 100 (e.g., 96) modulators. If 1536 well plates are used, then a single plate can easily assay from about 100-about 1500 different compounds. It is possible to assay many plates per day; assay screens for up to about 6,000, 20,000, 50,000, or more than 100,000 different compounds are possible using the integrated systems of the invention.

For a solid state reaction, the protein of interest or a fragment thereof, e.g., an extracellular domain, or a cell or membrane comprising the protein of interest or a fragment thereof as part of a fusion protein can be bound to the solid state component, directly or indirectly, via covalent or non covalent linkage e.g., via a tag. The tag can be any of a variety of components. In general, a molecule which binds the tag (a tag binder) is fixed to a solid support, and the tagged molecule of interest is attached to the solid support by interaction of the tag and the tag binder.

A number of tags and tag binders can be used, based upon known molecular interactions well described in the literature. For example, where a tag has a natural binder, for example, biotin, protein A, or protein G, it can be used in conjunction with appropriate tag binders (avidin, streptavidin, neutravidin, the Fc region of an immunoglobulin, etc.) Antibodies to molecules with natural binders such as biotin are also widely available and appropriate tag binders; see, SIGMA Immunochemicals 1998 catalogue SIGMA, St. Louis Mo.).

Similarly, any haptenic or antigenic compound can be used in combination with an appropriate antibody to form a tag/tag binder pair. Thousands of specific antibodies are commercially available and many additional antibodies are described in the literature. For example, in one common configuration, the tag is a first antibody and the tag binder is a second antibody which recognizes the first antibody. In addition to antibody-antigen interactions, receptor-ligand interactions are also appropriate as tag and tag-binder pairs. For example, agonists and antagonists of cell membrane receptors (e.g., cell receptor-ligand interactions such as transferrin, c-kit, viral receptor ligands, cytokine receptors, chemokine receptors, interleukin receptors, immunoglobulin receptors and antibodies, the cadherein family, the integrin family, the selectin family, and the like; see, e.g., Pigott & Power, *The Adhesion Molecule Facts Book I* (1993). Similarly, toxins and venoms, viral epitopes, hormones (e.g., opiates, steroids, etc.), intracellular receptors (e.g. which mediate the effects of various small ligands, including steroids, thyroid hormone, retinoids and vitamin D; peptides), drugs, lectins, sugars, nucleic acids (both linear and cyclic polymer configurations), oligosaccharides, proteins, phospholipids and antibodies can all interact with various cell receptors.

Synthetic polymers, such as polyurethanes, polyesters, polycarbonates, polyureas, polyamides, polyethyleneimines, polyarylene sulfides, polysiloxanes, polyimides, and polyacetates can also form an appropriate tag or tag binder. Many other tag/tag binder pairs are also useful in assay systems described herein, as would be apparent to one of skill upon review of this disclosure.

Common linkers such as peptides, polyethers, and the like can also serve as tags, and include polypeptide sequences, such as poly gly sequences of between about 5 and 200 amino acids. Such flexible linkers are known to persons of skill in the art. For example, poly(ethylene glycol) linkers are available from Shearwater Polymers, Inc. Huntsville, Ala. These linkers optionally have amide linkages, sulfhydryl linkages, or heterofunctional linkages.

Tag binders are fixed to solid substrates using any of a variety of methods currently available. Solid substrates are commonly derivatized or functionalized by exposing all or a portion of the substrate to a chemical reagent which fixes a chemical group to the surface which is reactive with a portion of the tag binder. For example, groups which are suitable for attachment to a longer chain portion would include amines, hydroxyl, thiol, and carboxyl groups. Aminoalkylsilanes and hydroxyalkylsilanes can be used to functionalize a variety of surfaces, such as glass surfaces. The construction of such solid phase biopolymer arrays is well described in the literature. See, e.g., Merrifield, *J. Am. Chem. Soc.* 85:2149-2154 (1963) (describing solid phase synthesis of, e.g., peptides); Geysen et al., *J. Immun. Meth.* 102:259-274 (1987) (describing synthesis of solid phase components on pins); Frank & Doring, *Tetrahedron* 44:60316040 (1988) (describing synthesis of various peptide sequences on cellulose disks); Fodor et al., *Science,* 251:767-777 (1991); Sheldon et al., *Clinical Chemistry* 39(4):718-719 (1993); and Kozal et al., *Nature Medicine* 2(7):753759 (1996) (all describing arrays of biopolymers fixed to solid substrates). Non-chemical approaches for fixing tag binders to substrates include other common methods, such as heat, cross-linking by UV radiation, and the like.

Immunological Detection of T1R3-Comprising Receptors

In addition to the detection of T1R genes and gene expression using nucleic acid hybridization technology, one can also use immunoassays to detect T1R3-comprising sweet taste receptors of the invention. Such assays are useful for screening for modulators of T1R3-comprising sweet taste receptors, as well as for therapeutic and diagnostic applications. Immunoassays can be used to qualitatively or quantitatively analyze T1R3-comprising sweet taste receptors. A general overview of the applicable technology can be found in Harlow & Lane, *Antibodies: A Laboratory Manual* (1988).

A. Production of Antibodies

Methods of producing polyclonal and monoclonal antibodies that react specifically with the T1R proteins and T1R3-comprising sweet taste receptors are known to those of skill in the art (see, e.g., Coligan, *Current Protocols in Immunology* (1991); Harlow & Lane, supra; Goding, *Monoclonal Antibodies: Principles and Practice* (2d ed. 1986); and Kohler & Milstein, *Nature* 256:495-497 (1975). Such techniques include antibody preparation by selection of antibodies from libraries of recombinant antibodies in phage or similar vectors, as well as preparation of polyclonal and monoclonal antibodies by immunizing rabbits or mice (see, e.g., Huse et al., *Science* 246:1275-1281 (1989); Ward et al., *Nature* 341: 544-546 (1989)).

A number of immunogens comprising portions of T1R protein or T1R3-comprising sweet taste receptor may be used to produce antibodies specifically reactive with T1R protein. For example, recombinant T1R protein or an antigenic fragment thereof, can be isolated as described herein. Recombinant protein can be expressed in eukaryotic or prokaryotic cells as described above, and purified as generally described above. Recombinant protein is the preferred immunogen for the production of monoclonal or polyclonal antibodies. Alternatively, a synthetic peptide derived from the sequences disclosed herein and conjugated to a carrier protein can be used an immunogen. Naturally occurring protein may also be used either in pure or impure form. The product is then injected into an animal capable of producing antibodies. Either monoclonal or polyclonal antibodies may be generated, for subsequent use in immunoassays to measure the protein.

Methods of production of polyclonal antibodies are known to those of skill in the art. An inbred strain of mice (e.g., BALB/C mice) or rabbits is immunized with the protein using a standard adjuvant, such as Freund's adjuvant, and a standard immunization protocol. The animal's immune response to the immunogen preparation is monitored by taking test bleeds and determining the titer of reactivity to the beta subunits. When appropriately high titers of antibody to the immunogen are obtained, blood is collected from the animal and antisera are prepared. Further fractionation of the antisera to enrich for antibodies reactive to the protein can be done if desired (see, Harlow & Lane, supra).

Monoclonal antibodies may be obtained by various techniques familiar to those skilled in the art. Briefly, spleen cells from an animal immunized with a desired antigen are immortalized, commonly by fusion with a myeloma cell (see, Kohler & Milstein, *Eur. J. Immunol.* 6:511-519 (1976)). Alternative methods of immortalization include transformation with Epstein Barr Virus, oncogenes, or retroviruses, or other methods well known in the art. Colonies arising from single immortalized cells are screened for production of antibodies of the desired specificity and affinity for the antigen, and yield of the monoclonal antibodies produced by such cells may be enhanced by various techniques, including injection into the peritoneal cavity of a vertebrate host. Alternatively, one may isolate DNA sequences which encode a monoclonal antibody or a binding fragment thereof by screening a DNA library from human B cells according to the general protocol outlined by Huse, et al., *Science* 246:1275-1281 (1989).

Monoclonal antibodies and polyclonal sera are collected and titered against the immunogen protein in an immunoassay, for example, a solid phase immunoassay with the immunogen immobilized on a solid support. Typically, polyclonal antisera with a titer of 104 or greater are selected and tested for their cross reactivity against non-T1R or T1R3-comprising sweet taste receptor proteins, using a competitive binding immunoassay. Specific polyclonal antisera and monoclonal antibodies will usually bind with a $K_d$ of at least about 0.1 mM, more usually at least about 1 μM, preferably at least about 0.1 μM or better, and most preferably, 0.01 μM or better. Antibodies specific only for a particular T1R3-comprising sweet taste receptor ortholog, such as human T1R3-comprising sweet taste receptor, can also be made, by subtracting out other cross-reacting orthologs from a species such as a non-human mammal. In addition, individual T1R proteins can be used to subtract out antibodies that bind both to the receptor and the individual T1R proteins. In this manner, antibodies that bind only to a heterodimeric receptor may be obtained.

Once the specific antibodies against T1R3-comprising sweet taste receptors are available, the protein can be detected by a variety of immunoassay methods. In addition, the antibody can be used therapeutically as a T1R3-comprising sweet taste receptor modulators. For a review of immunological and immunoassay procedures, see *Basic and Clinical Immunology* (Stites & Terr eds., 7$^{th}$ ed. 1991). Moreover, the immunoassays of the present invention can be performed in any of several configurations, which are reviewed extensively in Enzyme Immunoassay (Maggio, ed., 1980); and Harlow & Lane, supra.

B. Immunological Binding Assays

T1R3-comprising sweet taste receptors can be detected and/or quantified using any of a number of well recognized immunological binding assays (see, e.g., U.S. Pat. Nos. 4,366,241; 4,376,110; 4,517,288; and 4,837,168). For a review of the general immunoassays, see also *Methods in Cell Biology: Antibodies in Cell Biology*, volume 37 (Asai, ed. 1993); *Basic and Clinical Immunology* (Stites & Terr, eds., 7th ed. 1991). Immunological binding assays (or immunoassays) typically use an antibody that specifically binds to a protein or antigen of choice (in this case the T1R3-comprising sweet taste receptor or antigenic subsequence thereof). The antibody (e.g., anti-T1R3-comprising sweet taste receptor) may be produced by any of a number of means well known to those of skill in the art and as described above.

Immunoassays also often use a labeling agent to specifically bind to and label the complex formed by the antibody and antigen. The labeling agent may itself be one of the moieties comprising the antibody/antigen complex. Thus, the labeling agent may be a labeled T1R3-comprising sweet taste receptor or a labeled anti-T1R3-comprising sweet taste receptor antibody. Alternatively, the labeling agent may be a third moiety, such a secondary antibody, that specifically binds to the antibody/T1R3-comprising sweet taste receptor complex (a secondary antibody is typically specific to antibodies of the species from which the first antibody is derived). Other proteins capable of specifically binding immunoglobulin constant regions, such as protein A or protein G may also be used as the label agent. These proteins exhibit a strong non-immunogenic reactivity with immunoglobulin constant regions from a variety of species (see, e.g., Kronval et al., *J. Immunol.* 111:1401-1406 (1973); Akerstrom et al., *J. Immunol.* 135:2589-2542 (1985)). The labeling agent can be modified with a detectable moiety, such as biotin, to which another molecule can specifically bind, such as streptavidin. A variety of detectable moieties are well known to those skilled in the art.

Throughout the assays, incubation and/or washing steps may be required after each combination of reagents. Incubation steps can vary from about 5 seconds to several hours, optionally from about 5 minutes to about 24 hours. However, the incubation time will depend upon the assay format, antigen, volume of solution, concentrations, and the like. Usually, the assays will be carried out at ambient temperature, although they can be conducted over a range of temperatures, such as 10° C. to 40° C.

Non-Competitive Assay Formats

Immunoassays for detecting T1R3-comprising sweet taste receptors in samples may be either competitive or noncompetitive. Noncompetitive immunoassays are assays in which the amount of antigen is directly measured. In one preferred "sandwich" assay, for example, the anti-T1R3-comprising sweet taste receptor antibodies can be bound directly to a solid substrate on which they are immobilized. These immobilized antibodies then capture T1R3-comprising sweet taste receptors present in the test sample. T1R3-comprising sweet taste receptors thus immobilized are then bound by a labeling agent, such as a second T1R3-comprising sweet taste receptor antibody bearing a label. Alternatively, the second antibody may lack a label, but it may, in turn, be bound by a labeled third antibody specific to antibodies of the species from which the second antibody is derived. The second or third antibody is typically modified with a detectable moiety, such as biotin, to which another molecule specifically binds, e.g., streptavidin, to provide a detectable moiety.

Competitive Assay Formats

In competitive assays, the amount of T1R3-comprising sweet taste receptor present in the sample is measured indirectly by measuring the amount of a known, added (exogenous) T1R3-comprising sweet taste receptor displaced (competed away) from an anti-T1R3-comprising sweet taste receptor antibody by the unknown T1R3-comprising sweet taste receptor present in a sample. In one competitive assay, a known amount of T1R3-comprising sweet taste receptor is added to a sample and the sample is then contacted with an antibody that specifically binds to a T1R3-comprising sweet taste receptor. The amount of exogenous T1R3-comprising sweet taste receptor bound to the antibody is inversely proportional to the concentration of T1R3-comprising sweet taste receptor present in the sample. In a particularly preferred embodiment, the antibody is immobilized on a solid substrate. The amount of T1R3-comprising sweet taste receptor bound to the antibody may be determined either by measuring the amount of T1R3-comprising sweet taste receptor present in a T1R3-comprising sweet taste receptor/antibody complex, or alternatively by measuring the amount of remaining uncomplexed protein. The amount of T1R3-comprising sweet taste receptor may be detected by providing a labeled T1R3-comprising sweet taste receptor molecule.

A hapten inhibition assay is another preferred competitive assay. In this assay the known T1R3-comprising sweet taste receptor is immobilized on a solid substrate. A known amount of anti-T1R3-comprising sweet taste receptor antibody is added to the sample, and the sample is then contacted with the immobilized T1R3-comprising sweet taste receptor. The amount of anti-T1R3-comprising sweet taste receptor antibody bound to the known immobilized T1R3-comprising sweet taste receptor is inversely proportional to the amount of T1R3-comprising sweet taste receptor present in the sample. Again, the amount of immobilized antibody may be detected by detecting either the immobilized fraction of antibody or the fraction of the antibody that remains in solution. Detection may be direct where the antibody is labeled or indirect by the subsequent addition of a labeled moiety that specifically binds to the antibody as described above.

Cross-Reactivity Determinations

Immunoassays in the competitive binding format can also be used for crossreactivity determinations. For example, a T1R3-comprising sweet taste receptor can be immobilized to a solid support. Proteins (e.g., T1R3-comprising sweet taste receptors and homologs) are added to the assay that compete for binding of the antisera to the immobilized antigen. The ability of the added proteins to compete for binding of the antisera to the immobilized protein is compared to the ability of the T1R3-comprising sweet taste receptor to compete with itself. The percent crossreactivity for the above proteins is calculated, using standard calculations. Those antisera with less than 10% crossreactivity with each of the added proteins listed above are selected and pooled. The cross-reacting antibodies are optionally removed from the pooled antisera by immunoabsorption with the added considered proteins, e.g., distantly related homologs.

The immunoabsorbed and pooled antisera are then used in a competitive binding immunoassay as described above to compare a second protein, thought to be perhaps an allele or polymorphic variant of a T1R3-comprising sweet taste receptor, to the immunogen protein. In order to make this comparison, the two proteins are each assayed at a wide range of concentrations and the amount of each protein required to inhibit 50% of the binding of the antisera to the immobilized protein is determined. If the amount of the second protein required to inhibit 50% of binding is less than 10 times the amount of the T1R3-comprising sweet taste receptor that is required to inhibit 50% of binding, then the second protein is said to specifically bind to the polyclonal antibodies generated to a T1R3-comprising sweet taste receptor immunogen.

Other Assay Formats

Western blot (immunoblot) analysis is used to detect and quantify the presence of T1R3-comprising sweet taste receptors in the sample. The technique generally comprises separating sample proteins by gel electrophoresis on the basis of molecular weight, transferring the separated proteins to a suitable solid support, (such as a nitrocellulose filter, a nylon filter, or derivatized nylon filter), and incubating the sample with the antibodies that specifically bind T1R3-comprising sweet taste receptors. The anti-T1R3-comprising sweet taste receptor antibodies specifically bind to the T1R3-comprising sweet taste receptor on the solid support. These antibodies may be directly labeled or alternatively may be subsequently detected using labeled antibodies (e.g., labeled sheep antimouse antibodies) that specifically bind to the anti-T1R3-comprising sweet taste receptor antibodies.

Other assay formats include liposome immunoassays (LIA), which use liposomes designed to bind specific molecules (e.g., antibodies) and release encapsulated reagents or markers. The released chemicals are then detected according to standard techniques (see Monroe et al., *Amer. Clin. Prod. Rev.* 5:34-41 (1986)).

Reduction of Non-Specific Binding

One of skill in the art will appreciate that it is often desirable to minimize non-specific binding in immunoassays. Particularly, where the assay involves an antigen or antibody immobilized on a solid substrate it is desirable to minimize the amount of non-specific binding to the substrate. Means of reducing such non-specific binding are well known to those of skill in the art. Typically, this technique involves coating the substrate with a proteinaceous composition. In particular, protein compositions such as bovine serum albumin (BSA), nonfat powdered milk, and gelatin are widely used with powdered milk being most preferred.

Labels

The particular label or detectable group used in the assay is not a critical aspect of the invention, as long as it does not significantly interfere with the specific binding of the antibody used in the assay. The detectable group can be any material having a detectable physical or chemical property. Such detectable labels have been well-developed in the field of immunoassays and, in general, most any label useful in such methods can be applied to the present invention. Thus, a label is any composition detectable by spectroscopic, photochemical, biochemical, immunochemical, electrical, optical or chemical means. Useful labels in the present invention include magnetic beads (e.g., DYNABEADS™), fluorescent dyes (e.g., fluorescein isothiocyanate, Texas red, rhodamine, and the like), radiolabels (e.g., $^3$H, $^{125}$I, $^{35}$S, $^{14}$C, or $^{32}$P), enzymes (e.g., horse radish peroxidase, alkaline phosphatase and others commonly used in an ELISA), and calorimetric labels such as colloidal gold or colored glass or plastic beads (e.g., polystyrene, polypropylene, latex, etc.).

The label may be coupled directly or indirectly to the desired component of the assay according to methods well known in the art. As indicated above, a wide variety of labels may be used, with the choice of label depending on sensitivity required, ease of conjugation with the compound, stability requirements, available instrumentation, and disposal provisions.

Non-radioactive labels are often attached by indirect means. Generally, a ligand molecule (e.g., biotin) is covalently bound to the molecule. The ligand then binds to another molecules (e.g., streptavidin) molecule, which is either inherently detectable or covalently bound to a signal system, such as a detectable enzyme, a fluorescent compound, or a chemiluminescent compound. The ligands and their targets can be used in any suitable combination with antibodies that recognize T1R3-comprising sweet taste receptors, or secondary antibodies that recognize anti-T1R3-comprising sweet taste receptor.

The molecules can also be conjugated directly to signal generating compounds, e.g., by conjugation with an enzyme or fluorophore. Enzymes of interest as labels will primarily be hydrolases, particularly phosphatases, esterases and glycosidases, or oxidotases, particularly peroxidases. Fluorescent compounds include fluorescein and its derivatives, rhodamine and its derivatives, dansyl, umbelliferone, etc. Chemiluminescent compounds include luciferin, and 2,3-dihydrophthalazinediones, e.g., luminol. For a review of various labeling or signal producing systems that may be used, see U.S. Pat. No. 4,391,904.

Means of detecting labels are well known to those of skill in the art. Thus, for example, where the label is a radioactive label, means for detection include a scintillation counter or photographic film as in autoradiography. Where the label is a fluorescent label, it may be detected by exciting the fluorochrome with the appropriate wavelength of light and detecting the resulting fluorescence. The fluorescence may be detected visually, by means of photographic film, by the use of electronic detectors such as charge coupled devices (CCDs) or photomultipliers and the like. Similarly, enzymatic labels may be detected by providing the appropriate substrates for the enzyme and detecting the resulting reaction product. Finally simple calorimetric labels may be detected simply by observing the color associated with the label. Thus, in various dipstick assays, conjugated gold often appears pink, while various conjugated beads appear the color of the bead.

Some assay formats do not require the use of labeled components. For instance, agglutination assays can be used to detect the presence of the target antibodies. In this case, antigen-coated particles are agglutinated by samples comprising the target antibodies. In this format, none of the components need be labeled and the presence of the target antibody is detected by simple visual inspection.

Pharmaceutical Compositions and Administration

Pharmaceutically acceptable carriers are determined in part by the particular composition being administered (e.g., nucleic acid, oligonucleotide, protein, peptide, small organic molecule, lipid, carbohydrate, particle, or transduced cell), as well as by the particular method used to administer the composition. Accordingly, there are a wide variety of suitable formulations of pharmaceutical compositions of the present invention (see, e.g., *Remington's Pharmaceutical Sciences*, 17th ed., 1989). Administration can be in any convenient manner, e.g., by injection, oral administration, inhalation, transdermal application, or rectal administration.

Formulations suitable for oral administration can consist of (a) liquid solutions, such as an effective amount of the packaged nucleic acid suspended in diluents, such as water, saline or PEG 400; (b) capsules, sachets or tablets, each containing a predetermined amount of the active ingredient, as liquids, solids, granules or gelatin; (c) suspensions in an appropriate liquid; and (d) suitable emulsions. Tablet forms can include one or more of lactose, sucrose, mannitol, sorbitol, calcium phosphates, corn starch, potato starch, microcrystalline cellulose, gelatin, colloidal silicon dioxide, talc, magnesium stearate, stearic acid, and other excipients, colorants, fillers, binders, diluents, buffering agents, moistening agents, preservatives, flavoring agents, dyes, disintegrating agents, and pharmaceutically compatible carriers. Lozenge forms can comprise the active ingredient in a flavor, e.g., sucrose, as well as pastilles comprising the active ingredient in an inert base, such as gelatin and glycerin or sucrose and acacia emulsions, gels, and the like containing, in addition to the active ingredient, carriers known in the art.

The compound of choice, alone or in combination with other suitable components, can be made into aerosol formulations (i.e., they can be "nebulized") to be administered via inhalation. Aerosol formulations can be placed into pressurized acceptable propellants, such as dichlorodifluoromethane, propane, nitrogen, and the like.

Formulations suitable for parenteral administration, such as, for example, by intraarticular (in the joints), intravenous, intramuscular, intradermal, intraperitoneal, and subcutaneous routes, include aqueous and non-aqueous, isotonic sterile injection solutions, which can contain antioxidants, buffers, bacteriostats, and solutes that render the formulation isotonic with the blood of the intended recipient, and aqueous and non-aqueous sterile suspensions that can include suspending agents, solubilizers, thickening agents, stabilizers, and preservatives. In the practice of this invention, compositions can be administered, for example, by intravenous infusion, orally, topically, intraperitoneally, intravesically or intrathecally. Parenteral administration and intravenous administration are the preferred methods of administration. The formulations of commends can be presented in unit-dose or multi-dose sealed containers, such as ampules and vials.

Injection solutions and suspensions can be prepared from sterile powders, granules, and tablets of the kind previously described. Cells transduced by nucleic acids for ex vivo therapy can also be administered intravenously or parenterally as described above.

The dose administered to a patient, in the context of the present invention should be sufficient to effect a beneficial therapeutic response in the patient over time. The dose will be determined by the efficacy of the particular vector employed and the condition of the patient, as well as the body weight or surface area of the patient to be treated. The size of the dose also will be determined by the existence, nature, and extent of any adverse side-effects that accompany the administration of a particular vector, or transduced cell type in a particular patient.

In determining the effective amount of the vector to be administered in the treatment or prophylaxis of conditions owing to diminished or aberrant expression of a T1R3-comprising sweet taste receptor, the physician evaluates circulating plasma levels of the vector, vector toxicities, progression of the disease, and the production of anti-vector antibodies. In general, the dose equivalent of a naked nucleic acid from a vector is from about 1 µg to 100 µg for a typical 70 kilogram patient, and doses of vectors which include a retroviral particle are calculated to yield an equivalent amount of therapeutic nucleic acid.

For administration, compounds and transduced cells of the present invention can be administered at a rate determined by the LD-50 of the inhibitor, vector, or transduced cell type, and the side-effects of the inhibitor, vector or cell type at various concentrations, as applied to the mass and overall health of the patient. Administration can be accomplished via single or divided doses.

Cellular Transfection and Gene Therapy

The present invention provides the nucleic acids of T1R3-comprising sweet taste receptors for the transfection of cells in vitro and in vivo. These nucleic acids can be inserted into any of a number of well-known vectors for the transfection of target cells and organisms as described below. The nucleic acids are transfected into cells, ex vivo or in vivo, through the interaction of the vector and the target cell. The nucleic acid, under the control of a promoter, then expresses a T1R3-comprising sweet taste receptor of the present invention, by co-expressing two members of the T1R family, thereby mitigating the effects of absent, partial inactivation, or abnormal expression of a T1R3-comprising sweet taste receptor. The compositions are administered to a patient in an amount sufficient to elicit a therapeutic response in the patient. An amount adequate to accomplish this is defined as "therapeutically effective dose or amount."

Such gene therapy procedures have been used to correct acquired and inherited genetic defects and other diseases in a number of contexts. The ability to express artificial genes in humans facilitates the prevention and/or cure of many important human diseases, including many diseases which are not amenable to treatment by other therapies (for a review of gene therapy procedures, see Anderson, *Science* 256:808-813 (1992); Nabel & Felgner, TIBTECH 11:211-217 (1993); Mitani & Caskey, TIBTECH 11:162-166 (1993); Mulligan, *Science* 926-932 (1993); Dillon, TIBTECH 11:167-175 (1993); Miller, *Nature* 357:455-460 (1992); Van Brunt, *Biotechnology* 6(10): 1149-1154 (1998); Vigne, *Restorative Neurology and Neuroscience* 8:35-36 (1995); Kremer & Perricaudet, *British Medical Bulletin* 51(1):31-44 (1995); Haddada et al., in *Current Topics in Microbiology and Immunology* (Doerfler & Bohm eds., 1995); and Yu et al., *Gene Therapy* 1:13-26 (1994)).

REFERENCES

Adler, E., Hoon, M. A., Mueller, K. L., Chandrashekar, J., Ryba, N. J. P., and Zuker, C. S. (2000). A novel family of mammalian taste receptors. *Cell* 100, 693-702.
  Bachmanov, A. A., Reed, D. R., Ninomiya, Y., Inoue, M., Tordoff, M. G., Price, R. A., and Beauchamp, G. K. (1997). Sucrose consumption in mice: major influence of two genetic loci affecting peripheral sensory responses. *Mamm. Genome* 8, 545-548.
  Baker, E. K., Colley, N. J., and Zuker, C. S. (1994). The cyclophilin homolog NinaA functions as a chaperone, forming a stable complex in vivo with its protein target rhodopsin. *EMBO J.* 13, 4886-4895.
  Boughter Jr., J. D., Pumplin, D. W., Yu, C., Christy, R. C., and Smith, D. V. (1997). Differential expression of alpha-gustducin in taste bud populations of the rat and hamster. *J. Neurosci.* 17, 2852-2858.
  Brown, E. M., Gamba, G., Riccardi, D., Lombardi, M., Butters, R., Kifor, O., Sun, A., Hediger, M. A., Lytton, J., and Hebert, S. C. (1993). Cloning and characterization of an extracellular Ca(2+)-sensing receptor from bovine parathyroid. *Nature* 366, 575-580.
  Capeless, C. G., and Whitney, G. (1995). The genetic basis of preference for sweet substances among inbred strains of mice: preference ratio phenotypes and the alleles of the Sac and DNA loci. *Chem. Senses* 20, 291-298.
  Chandrashekar, J., Mueller, K. L., Hoon, M. A., Adler, E., Feng, L., Guo, W., Zuker, C. S., and Ryba, N. J. P. (2000). T2Rs function as bitter taste receptors. *Cell* 100, 703-11.
  Danilova, V., Hellekant, G., Tinti, J.-M., and Nofre, C. (1998). Gustatory Responses of the Hamster *Mesocricetus auratus* to Various Compounds Considered Sweet by Humans. *J. Neurophysiol.* 80, 2102-2112.
  Dwyer, N. D., Troemel, E. R., Sengupta, P., and Bargmann, C. I. (1998). Odorant receptor localization to olfactory cilia is mediated by ODR-4, a novel membrane-associated protein. *Cell* 93, 455-466.
  Fuller, J. L. (1974). Single-locus control of saccharin preference in mice. *J. Hered.* 65, 33-36.
  Herrada, G., and Dulac, C. (1997). A novel family of putative pheromone receptors in mammals with a topographically organized and sexually dimorphic distribution. *Cell* 90, 763-773.
  Hoon, M. A., Adler, E., Lindemeier, J., Battey, J. F., Ryba, N. J. P., and Zuker, C. S. (1999). Putative mammalian taste receptors: a class of taste-specific GPCRs with distinct topographic selectivity. *Cell* 96, 541-551.
  Kaupmann, K., Huggel, K., Heid, J., Flor, P. J., Bischoff, S., Mickel, S. J., McMaster, G., Angst, C., Bittiger, H., Froestl, W., and Bettler, B. (1997). Expression cloning of GABA(B) receptors uncovers similarity to metabotropic glutamate receptors. *Nature* 386, 239-246.

Kitagawa, M., Kusakabe, Y., Miura, H., Ninomiya, Y., and Hino, A. (2001). Molecular genetic identification of a candidate receptor gene for sweet taste. *Biochem. Biophys. Res. Commun.* 283, 236-242.

Krautwurst, D., Yau, K. W., and Reed, R. R. (1998). Identification of ligands for olfactory receptors by functional expression of a receptor library. *Cell* 95, 917-926.

Lefkowitz, R. J., Inglese, J., Koch, W. J., Pitcher, J., Attramadal, H., and Caron, M. G. (1992). G-protein-coupled receptors: regulatory role of receptor kinases and arrestin proteins. *Cold Spring Harb. Symp. Quant. Biol.* 57, 127-133.

Li, X., Inoue, M., Reed, D. R., Huque, T., Puchalski, R. B., Tordoff, M. G., Ninomiya, Y., Beauchamp, G. K., and Bachmanov, A. A. (2001). High-resolution genetic mapping of the saccharin preference locus (Sac) and the putative sweet taste receptor (T1R1) gene (Gpr70) to mouse distal Chromosome 4. *Mamm. Genome* 12, 13-16.

Lindemann, B. (1996). Taste reception. *Physiol. Rev.* 76, 718-766.

Lush, I. E. (1989). The genetics of tasting in mice. VI. Saccharin, acesulfame, dulcin and sucrose. *Genet. Res.* 53, 95-99.

Matsunami, H., and Buck, L. B. (1997). A multigene family encoding a diverse array of putative pheromone receptors in mammals. *Cell* 90, 775-784.

Matsunami, H., Montmayeur, J. P., and Buck, L. B. (2000). A family of candidate taste receptors in human and mouse. *Nature* 404, 601-604.

Max, M., Shanker, Y. G., Huang, L., Rong, M., Liu, Z., Campagne, F., Weinstein, H., Damak, S., and Margolskee, R. F. (2001). Tas1r3, encoding a new candidate taste receptor, is allelic to the sweet responsiveness locus Sac. *Nat. Genet.* 28, 58-63.

McBurney, D. H., and Gent, J. F. (1979). On the nature of taste qualities. *Psychol. Bull.* 86, 151-167.

Mistretta, C. M., and Hill, D. L. (1995). Development of the taste system. Basic neurobiology. In *Handbook of olfaction and gustation*, R. L. Doty, ed. (New York: Marcel Dekker), pp. 635-668.

Mody, S. M., Ho, M. K., Joshi, S. A., and Wong, Y. H. (2000). Incorporation of Galpha(z)-specific sequence at the carboxyl terminus increases the promiscuity of galpha(16) toward G(i)-coupled receptors. *Mol. Pharmacol.* 57, 13-23.

Montmayeur, J. P., Liberles, S. D., Matsunami, H., and Buck, L. B. (2001). A candidate taste receptor gene near a sweet taste locus. *Nat. Neurosci.* 4, 492-498.

Nagarajan, S., Kellogg, M. S., DuBois, G. E., and Hellekant, G. (1996). Understanding the mechanism of sweet taste: synthesis of ultrapotent guanidinoacetic acid photoaffinity labeling reagents. *J. Med. Chem.* 39, 4167-4172.

Nakanishi, S. (1992). Molecular diversity of glutamate receptors and implications for brain function. *Science* 258, 597-603.

Ninomiya, Y., Inoue, M., Imoto, T., and Nakashima, K. (1997). Lack of gurmarin sensitivity of sweet taste receptors innervated by the glossopharyngeal nerve in C57BL mice. *Am. J. Physiol.* 272, R1002-R1006.

Ninomiya, Y., Mizukoshi, T., Higashi, T., Katsukawa, H., and Funakoshi, M. (1984). Gustatory neural responses in three different strains of mice. *Brain Res.* 302, 305-314.

Offermanns, S., and Simon, M. I. (1995). G alpha 15 and G alpha 16 couple a wide variety of receptors to phospholipase C. *J. Biol. Chem.* 270, 15175-80.

Ryba, N. J. P., and Tirindelli, R. (1997). A new multigene family of putative pheromone receptors. *Neuron* 19, 371-379.

Sainz, E., Korley, J. N., Battey, J. F., and Sullivan, S. L. (2001). Identification of a novel member of the T1R family of putative taste receptors. *J. Neurochem.* 77, 896-903.

Salahpour, A., Angers, S., and Bouvier, M. (2000). Functional significance of oligomerization of G-protein-coupled receptors. *Trends Endocrinol. Metab.* 11, 163-168.

Schiffman, S. S., Cahn, H., and Lindley, M. G. (1981). Multiple receptor sites mediate sweetness: evidence from cross adaptation. *Pharmacol. Biochem. Behav.* 15, 377-388.

Scott, K., Brady, R., Jr., Cravchik, A., Morozov, P., Rzhetsky, A., Zuker, C., and Axel, R. (2001). A chemosensory gene family encoding candidate gustatory and olfactory receptors in *Drosophila*. *Cell* 104, 661-673.

Smith, D. V., and Frank, M. E. (1993). Sensory coding by peripheral taste fibers. In *Mechanisms of Taste Transduction*, S. A. Simon and S. D. Roper, eds. (Boca Raton: CRC Press), pp. 295-338.

Troemel, E. R., Chou, J. H., Dwyer, N. D., Colbert, H. A., and Bargmann, C. I. (1995). Divergent seven transmembrane receptors are candidate chemosensory receptors in *C. elegans*. *Cell* 83, 207-218.

Tsien, R. Y., Rink, T. J., and Poenie, M. (1985). Measurement of cytosolic free Ca2+ in individual small cells using fluorescence microscopy with dual excitation wavelengths. *Cell Calcium* 6, 145-157.

EXAMPLES

The following examples are offered to illustrate, but not to limit the claimed invention.

Results

T1R3 is Encoded by the Sac Locus

In previous studies, we identified two novel G protein-coupled receptors of the T1R family, T1R1 and T1R2, that are selectively expressed in subsets of taste receptor cells of the tongue and palate epithelium (Hoon et al., 1999; Genbank Accession numbers: AY032620-AY032623). We also previously identified functional bitter taste receptor genes, the T2R family (Adler et al., 2000; Chandrashekar et al., 2000). Both T1R1 and T1R2 were initially mapped to the distal end of chromosome 4, in the proximity of Sac (Hoon et al., 1999). However, radiation hybrid analysis and high-resolution genetic mapping separated these receptors from the Sac genetic interval (Li et al., 2001), thus eliminating them as candidate Sac genes (FIG. 1). Recently, six independent groups reported that a related receptor gene, T1R3, is tightly linked to the Sac locus (Kitagawa et al., 2001; Max et al., 2001; Montmayeur et al., 2001; Sainz et al., 2001 and press releases from Senomyx, La Jolla, Calif. and Li et al., 2001 Achems XXIII, Sarasota Fla.), and that polymorphic variants of T1R3 co-segregate with Sac taster and non-taster alleles. This genetic linkage was used to hypothesize that T1R3 corresponds to the Sac gene. We also isolated and characterized T1R3, and reasoned that if Sac in fact encodes T1R3, then introduction of a taster allele of this candidate receptor should rescue the taste deficit of Sac non-taster mice.

Figure 2A:
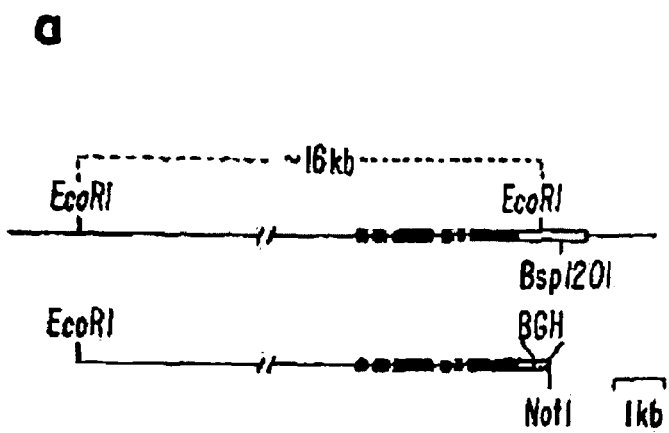
FIG. 2. T1R3 encodes Sac
(a) Schematic diagram indicating structure of the T1R3 gene and transgenic construct. The alternate 3'-UTRs used for genotyping and in situ hybridization are highlighted in green and red. (b) In situ hybridization demonstrated perfect concordance in the expression pattern of the T1R3 transgene (red) and the endogenous gene (green). The dotted lines illustrate the outline of selected taste buds; sections were cut perpendicular to the planes shown in FIG. 3. (c-h) Taste preferences of control and transgenic animals (solid red circles) were measured using standard two bottle preference tests. The behavioral responses of mice expressing the T1R3 transgene to saccharin and sucrose (panels c and d) were indistinguishable from those of the control taster mice (C57BL/6; open red circles). Siblings without the transgene (solid black circles) behaved like 129/Sv non-taster control mice (open black circles). Responses to bitter, salty, sour and umami stimuli (panels e-h) were not affected by presence of the transgene.
Figure 2A:
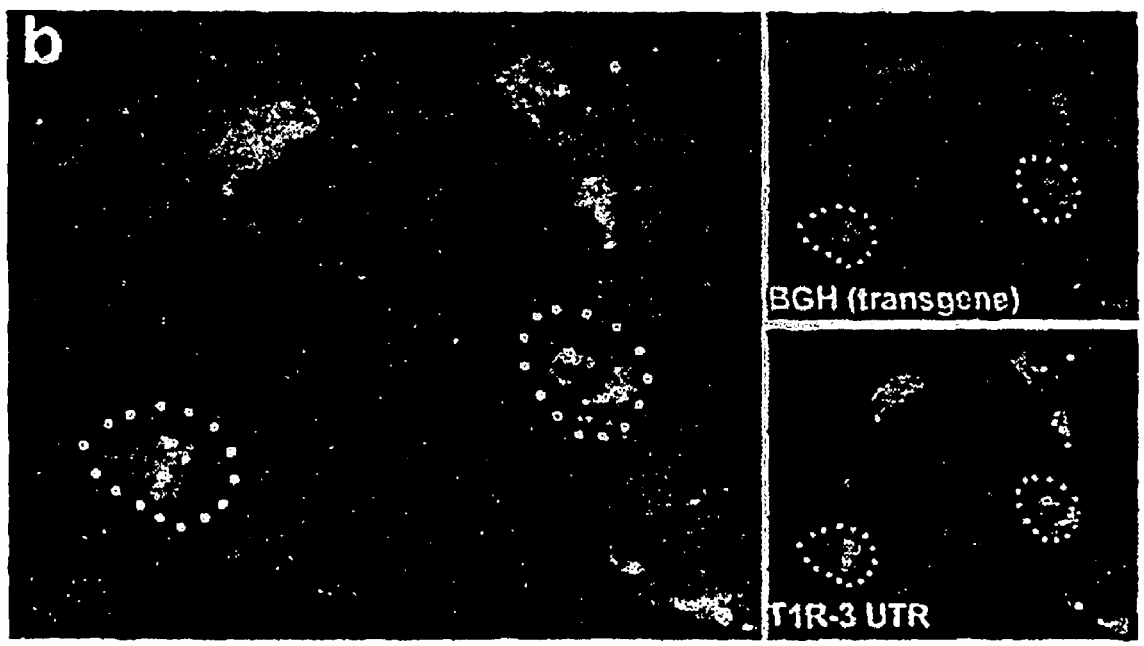
Figure 2B:
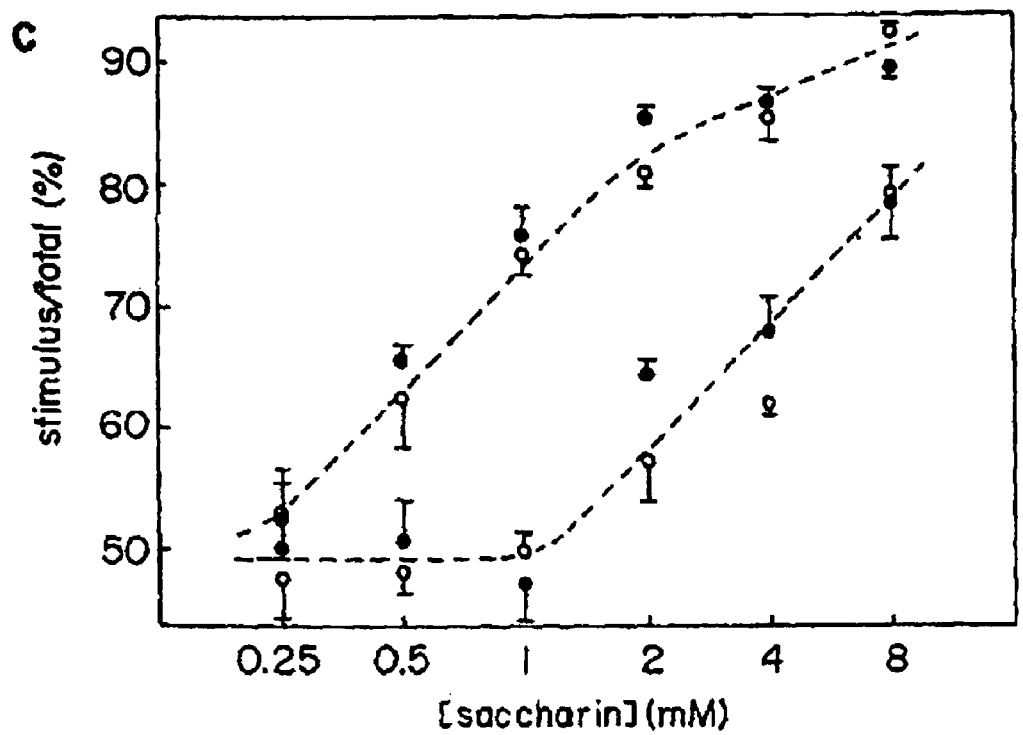
Figure 2B:
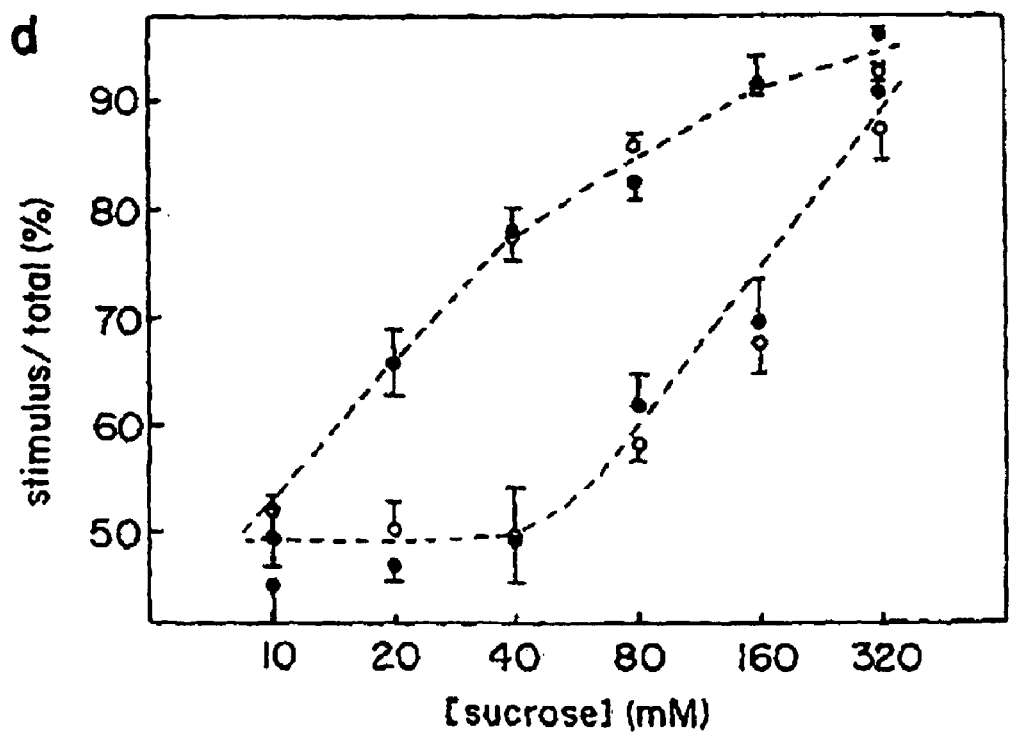

A 15 kb genomic clone containing the T1R3 sequence from a Sac taster strain (C57 BL/6) was used to engineer a transgenic rescue construct (FIG. 2a). In order to follow the presence and expression of the transgene versus the endogenous T1R3 allele, we replaced its 3'-UTR and poly-adenylation signal with that of bovine growth hormone. Our strategy was to produce progeny that were homozygous for the T1R3 non-taster allele, but carried the taster-derived transgene. We obtained 4 founder mice, and two independent lines were examined for appropriate expression of the transgene and assayed for behavioral rescue of sucrose and saccharin tasting (Fuller, 1974). Age- and sex-matched siblings that lacked the transgene were used as controls in all experiments. FIG. 2b illustrates that all the cells expressing the endogenous T1R3 receptor, and only these cells, also express the transgene (identical results were obtained in taster and non-taster genetic backgrounds; data not shown).

Figure 2C:
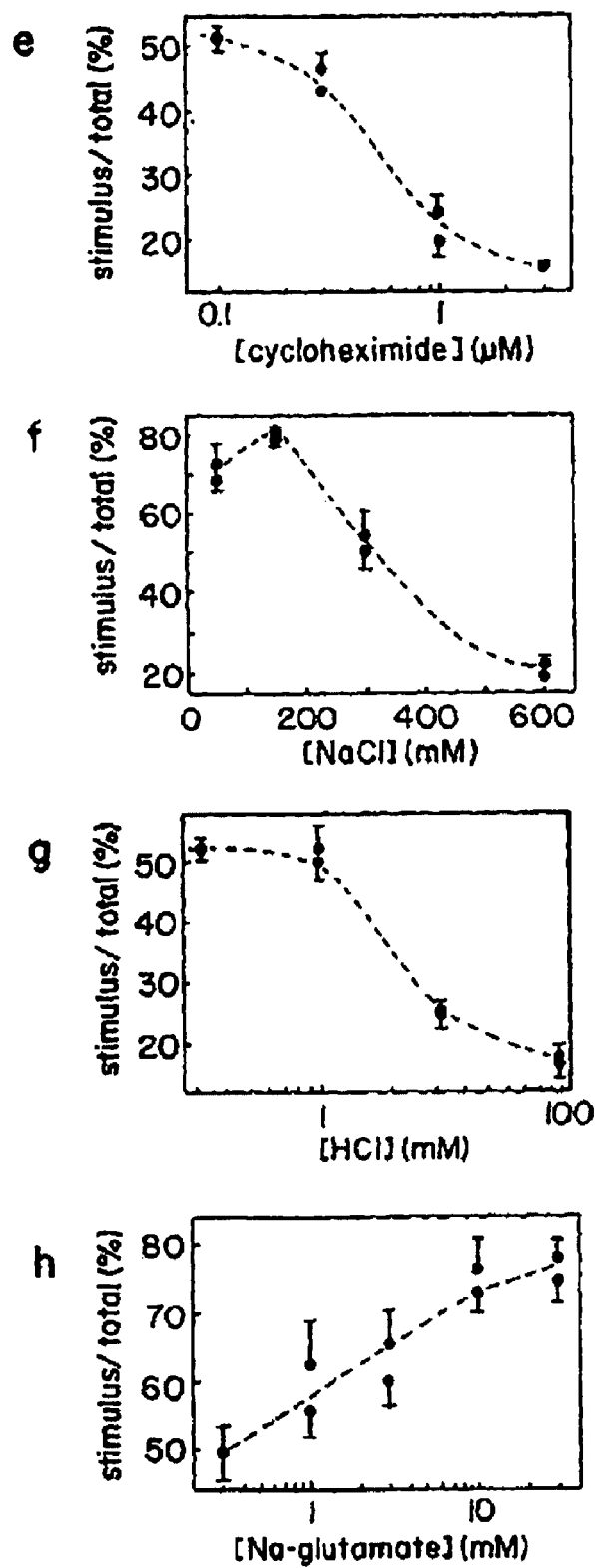

If the T1R3 taster allele rescues the taste deficiency of Sac non-tasters, their saccharin and sucrose dose-responses should be shifted to recapitulate the sensitivity seen in Sac taster animals (Fuller, 1974; Bachmanov et al., 1997). FIG. 2 demonstrates that the T1R3 transgene fully rescues the taste defect of Sac non-tasters. Animals without a transgene are indistinguishable from non-taster 129/Sv control mice (FIGS. 2c and d, open black circles). In contrast, siblings with the same Sac non-taster background but expressing the transgene are now equivalent to taster C57BL/6 control mice (FIGS. 2c and d, red traces). The presence of the transgene did not influence other taste modalities (FIG. 2e-h), nor did it alter the sweet sensitivity of taster strains (data not shown). Equivalent results were obtained with the two independent transgenic lines. These results validate T1R3 as the Sac locus, and suggest that T1R3 may function as a sweet taste receptor.

Expression of T1Rs

Figure 3:
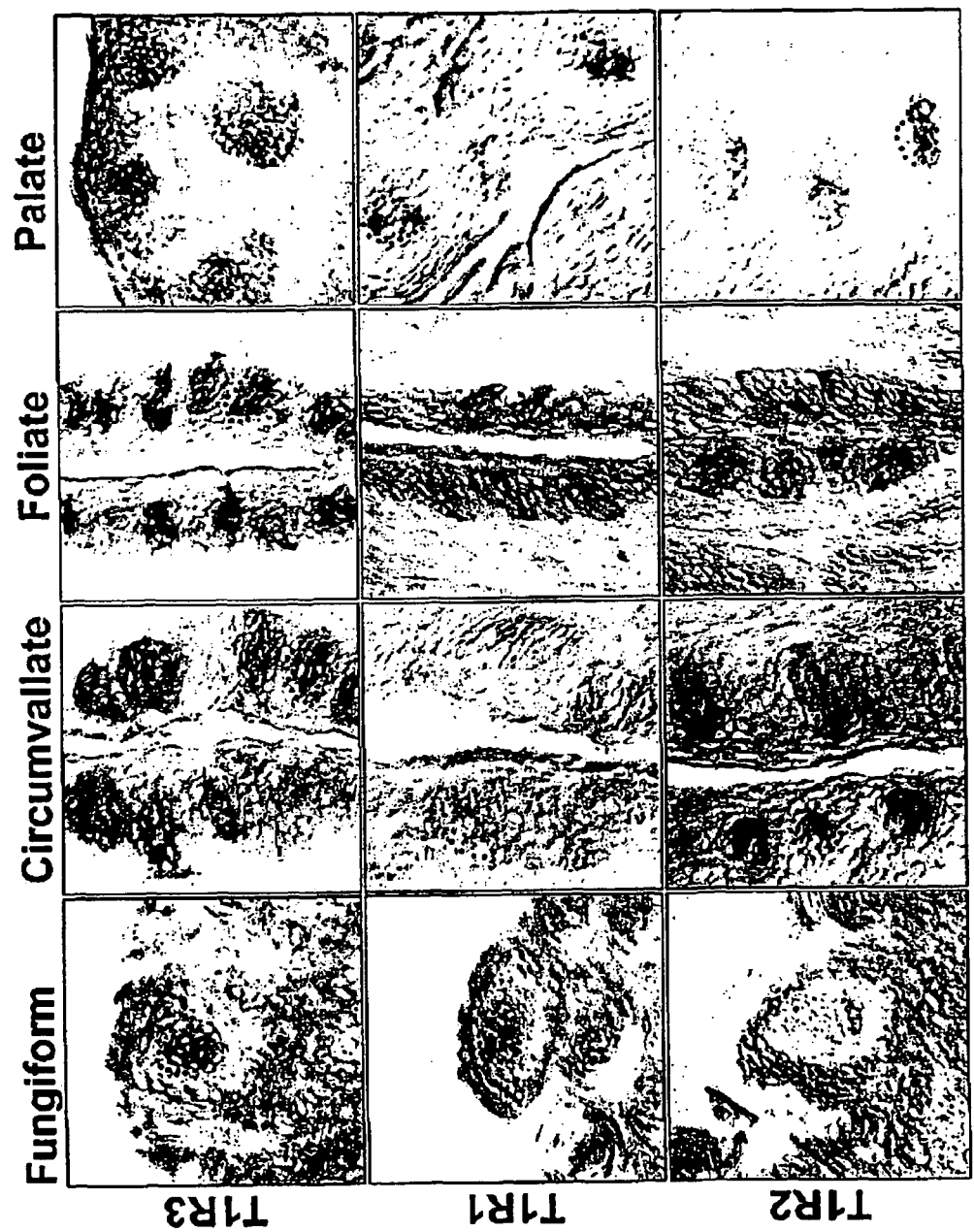
FIG. 3. Expression of T1Rs in subsets of taste receptor cells
In situ hybridizations with digoxigenin-labeled antisense RNA probes demonstrated that T1R3 is expressed in subsets of mouse taste receptor cells (upper panels). Approx. 30% of cells in fungiform, circumvallate, foliate and palate taste buds express T1R3. Shown for comparison are similar, but not serial, sections labeled with T1R1 and T1R2 (middle and lower panels; see also Hoon et al., 1999 and FIG. 4). The dotted lines illustrate the outline of a sample taste bud. Note that the selectivity of T1R3 expression closely resembles that of T1R1 plus T1R2.
Figure 4:
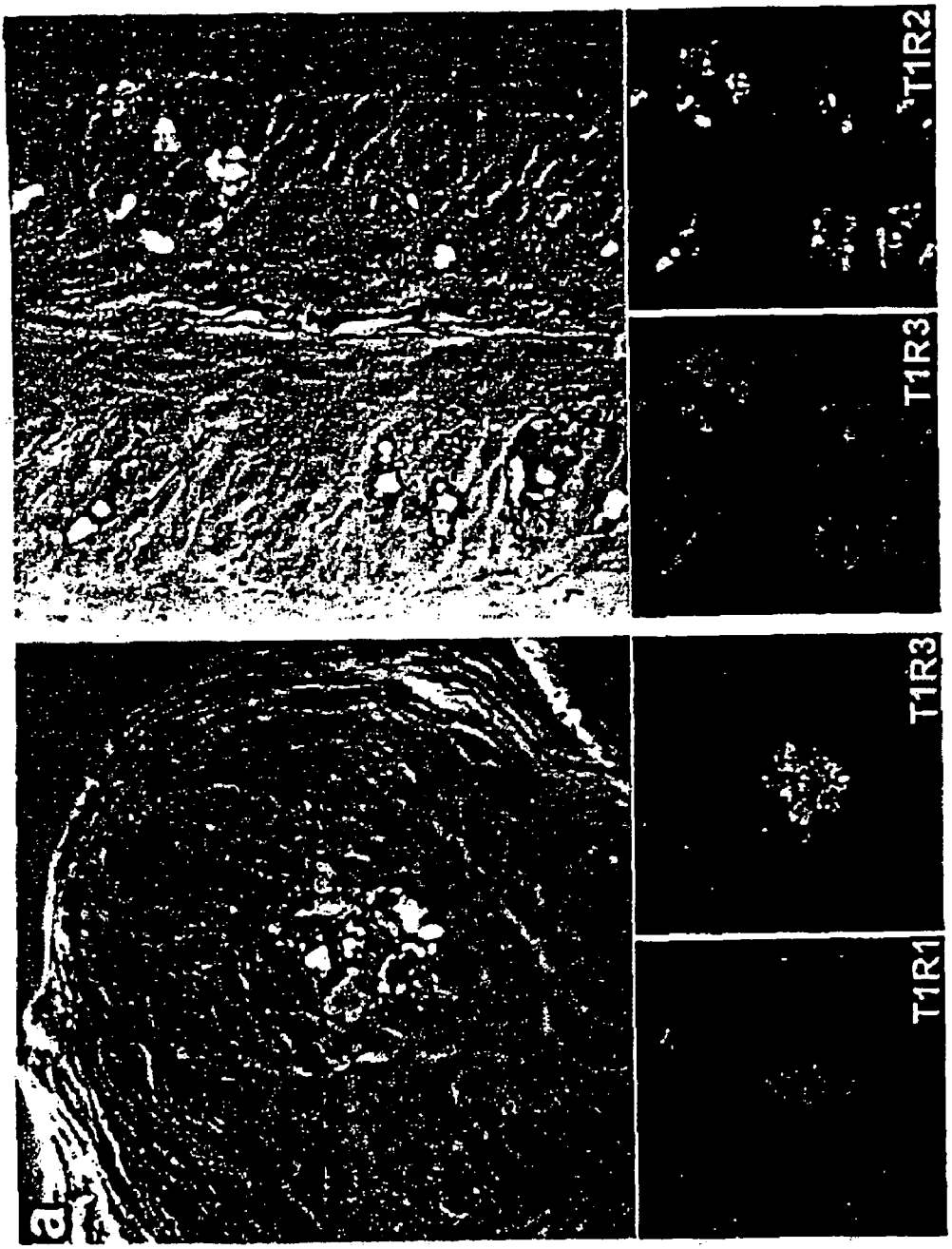
FIG. 4. T1R expression patterns define three cell types
Double-label fluorescent in situ hybridization was used to directly examine the overlap in cellular expression of T1Rs. Two-channel fluorescent images (1-2 μm optical sections) are overlaid on difference interference contrast images. (a) Fungiform papillae illustrating co-expression of T1R1 (red) and T1R3 (green). At least 90% of the cells expressing T1R1 also express T1R3; similar results were observed in the palate. Note the presence of some T1R3 positive but T1R1 negative cells. (b) Circumvallate papillae illustrating co-expression of T1R2 (green) and T1R3 (red). Every T1R2 positive cell expresses T1R3.

Recently, T1R3 was shown to be expressed in subsets of taste receptor cells in various taste papillae (Kitagawa et al., 2001; Max et al, 2001; Montmayeur et al., 2001; Sainz et al., 2001). However, there were significant discrepancies between the reported patterns of expression, with results ranging from little if any expression at the front of the tongue (fungiform papillae; Sainz et al., 2001) to significant expression in all taste buds (Kitagawa et al., 2001). We examined the expression of T1R3 in circumvallate, foliate, fungiform and palate taste buds and find that T1R3 is expressed in ~30% of cells from all types of taste buds (FIG. 3; see also Montmayeur et al., 2001). This topographic pattern of expression closely approximates the aggregate of T1R1 and T1R2 expression (FIG. 3, Hoon et al., 1999), and suggests possible co-expression of T1R1 with T1R3 and T1R2 with T1R3. The co-expression of T1R2 and T1R3 in circumvallate (Max et al., 2001; Montmayeur et al., 2001) and foliate papillae (Montmayeur et al., 2001) was recently examined by RT-PCR and by in situ hybridization, but a comprehensive study of all three T1Rs in the different classes of taste buds was lacking. Thus, we performed double labeling experiments using two-color fluorescent in situ hybridization. Our results demonstrated that T1R3 is co-expressed with T1R2 in all circumvallate, foliate and palate taste buds, with every T1R2-positive cell also expressing T1R3 (FIG. 4). Similarly, T1R1 is co-expressed with T1R3 in fungiform and palate taste receptor cells. However, there is also a fraction of cells with non-overlapping expression of T1R3 in fungiform and palate taste buds. Therefore, we can define three major classes of cell types based on their T1R expression profiles: T1R1 and T1R3 (T1R1+3), T1R2 and T1R3 (T1R2+3) and T1R3.

T1Rs Encode Functional Sweet Taste Receptors

Demonstration that T1Rs encode sweet receptors requires functional validation. To monitor translocation of receptors to the plasma membrane we raised antibodies against T1R1, T1R2 and T1R3, and tested expression of native and epitope-tagged mouse, human and rat receptors in various tissue culture cell lines. We observed that rat T1Rs were expressed efficiently; we therefore used the rat genes in all heterologous expression studies. To assay function, we expressed T1Rs with a Gα16-Gz chimera and Gα15, two G-protein α-subunits that together efficiently couple Gs, Gi, Gq and gustducin-linked receptors to phospholipase Cβ (Offermanns and Simon, 1995; Krautwurst et al., 1998; Chandrashekar et al., 2000; Mody et al., 2000). In this system, receptor activation leads to increases in intracellular calcium [$Ca^{2+}$]i, which can be monitored at the single cell level using the FURA-2 calcium-indicator dye (Tsien et al., 1985).

Figure 5:
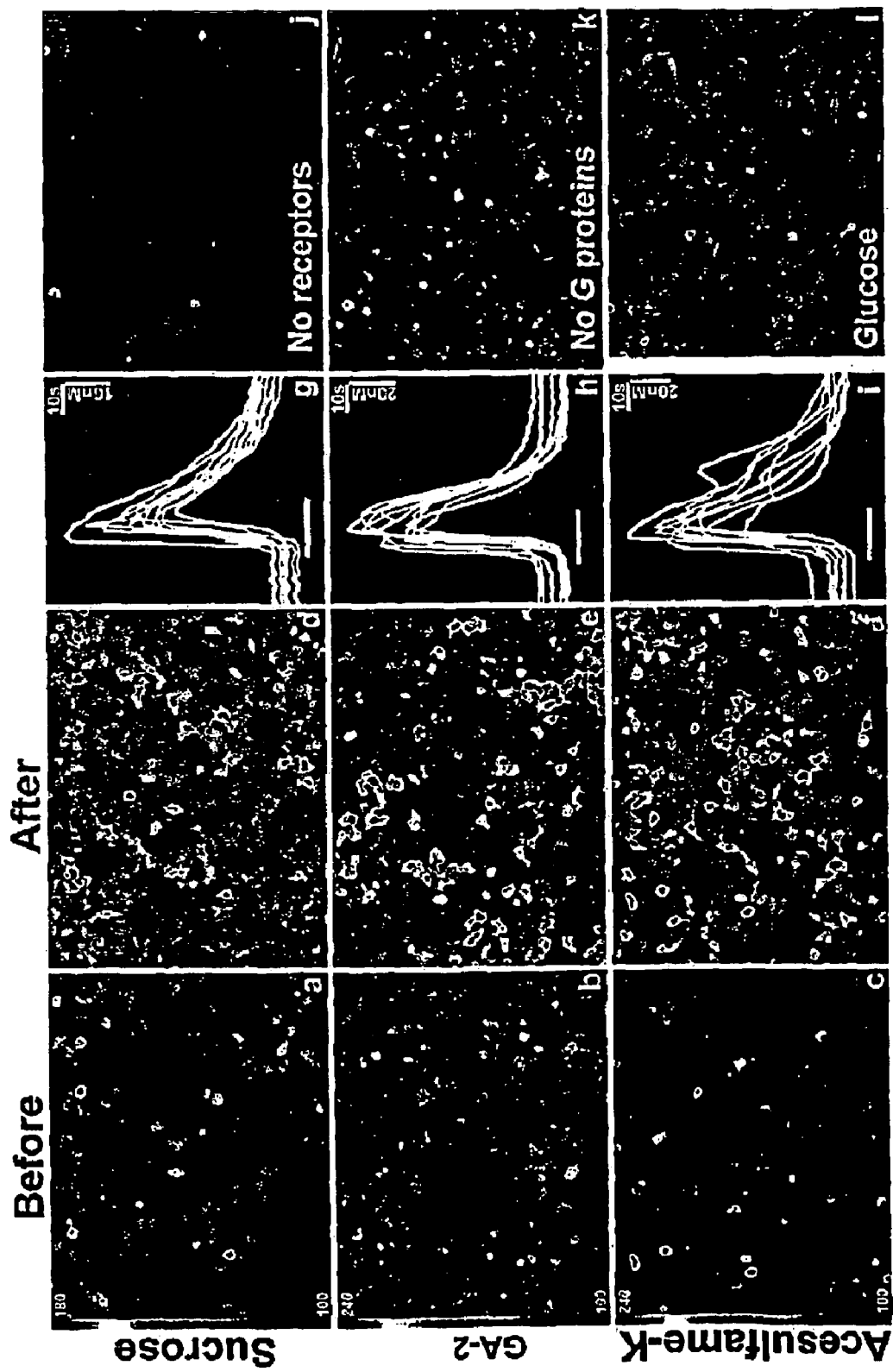
FIG. 5. T1R2+3 responds to sweet tastants
HEK-293 cells co-expressing promiscuous G proteins and rat T1R2 and T1R3 were stimulated with various sweet compounds. Robust increases in $[Ca^{2+}]i$ were observed upon addition of 250 mM sucrose (d, g), 180 μM GA-2 (e, h) and 10 mM acesulfame-K (f, i). Panels a-c show cells prior to stimulation. No responses were detected without receptors (panel j) or promiscuous G proteins (panel k). Glucose and several other sweet tastants (see next figure) did not activate this receptor combination (panel 1); scales indicate $[Ca^{2+}]i$ (nM) determined from FURA-2 $F_{340}/F_{380}$ ratios. Line traces (g-i) show the kinetics of the $[Ca^{2+}]i$ changes for representative cells from panels (d-f). The bar indicates the time and duration of the stimulus.
Figure 6A:
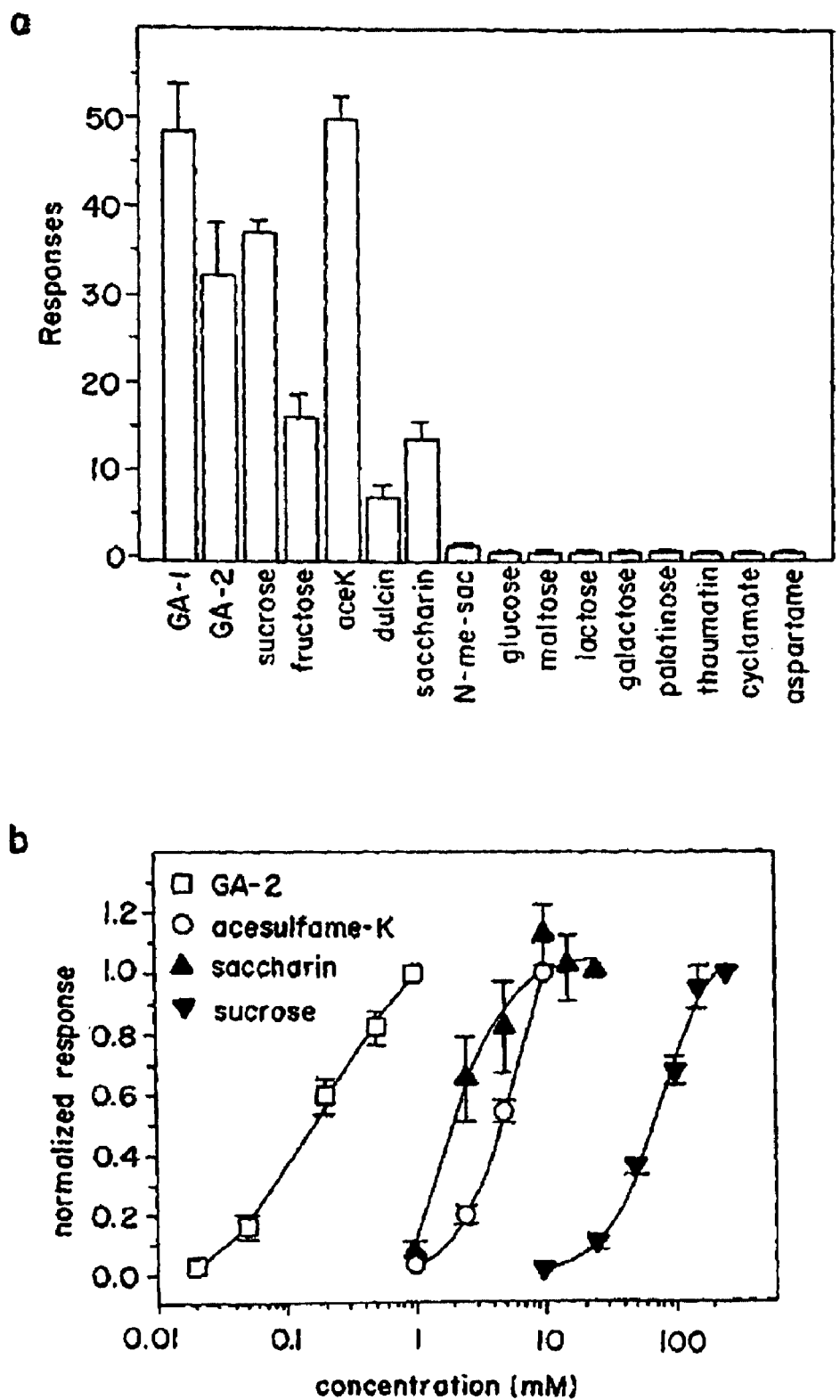
FIG. 6. T1R2+3 selectively responds to a broad range of sweet compounds
(a) The responses of the T1R2+3 receptor combination were specific to sucrose, fructose and five artificial sweeteners. Concentrations used are: GA-1 (500 μM); GA-2 (500 μM); sucrose (250 mM); fructose (250 mM), acesulfame-K (10 mM); dulcin (2 mM), sodium saccharin (5 mM); N-methyl saccharin (5 mM); glucose (250 mM); maltose (250 mM); lactose (250 mM); galactose (250 mM); palatinose (250 mM); thaumatin (0.1%); sodium cyclamate (15 mM); aspartame (2 mM). Columns represent the mean±SEM of a minimum of 16 independent determinations. (b) Dose response of T1R2+3 to sucrose, saccharin, acesulfame-K and GA-2. The relative changes in $[Ca^{2+}]i$ are shown as FURA-2 $(F_{340}/F_{380})$ ratios normalized to the responses obtained for the highest concentration of each compound. Each point represents the mean±SEM of a minimum of 20 assays. (c) Kinetics and desensitization of T1R2+3 sweet responses. Cells expressing T1R2+3 were stimulated with multiple pulses of sweet tastants; GA-2 (360 μM), sucrose, (suc: 250 mM), acesulfame-K (ace: 10 mM), cyclamate (sic: 15 mM), glucose (glu: 250 mM) and aspartame (asp: 2 mM). Dots and horizontal bars indicate the time and duration of the stimulus. Sucrose, GA-2 and acesulfame-K elicit robust responses; repeated or prolonged stimulation with any one of these tastants (e.g., GA-2) results in a decreased response indicative of desensitization. Stimulation with sucrose or acesulfame-K immediately after GA-2 results in an attenuated response suggesting cross-desensitization. The trace was derived from 80 responding cells in the field of view.

Because of the apparent co-expression of T1R1 or T1R2 with T1R3, we transfected various rat T1Rs singly and in combinations (for co-expression) into HEK-293 cells expressing the promiscuous Gα15 and Gα16-Gz proteins. After loading the cells with FURA-2, we assayed for responses to a wide range of sweet tastants, including sugars, amino acids, and artificial sweeteners; we also tested several bitter tastants (see Experimental Procedures). Cells expressing rat T1R2 and T1R3 (T1R2+3) robustly responded to a subset of sweet compounds including sucrose, fructose, saccharin (but not to N-methyl-saccharin, a non-sweet saccharin derivative), acesulfame-K, dulcin, and two novel intensely sweet compounds (Nagarajan et al, 1996, guanidinoacetic acid 1 and 2, referred to as GA-1 and GA-2; FIGS. 5 and 6a). The responses were receptor- and Gα-dependent because cells lacking either of these components did not trigger [$Ca^{2+}$]i changes, even at vastly higher concentrations of tastants (FIG. 5). Notably, the activation of T1R2+3 is extremely selective. On the one hand, this receptor combination did not respond to a large number of mono- and disaccharides and artificial sweeteners, including glucose, galactose, maltose and aspartame (FIG. 6a). On the other hand, the response was dependent on the presence of both T1R2 and T1R3; either receptor alone did not respond to any of the compounds assayed in these studies, even at concentrations that far exceeded their biologically relevant range of action (data not shown). These results demonstrate that T1R2 and T1R3, when co-expressed in the same cell, function as a sweet taste receptor.

Evidence that association of the polypeptides, or heteromerization, is required for the formation of a functional T1R receptor was obtained by co-expression of a dominant negative T1R. Co-transfection of wild type T1R2 and T1R3 with a T1R2 receptor harboring a C-terminal truncation (Salahpour et al., 2000) nearly abolished the T1R2+3 responses (>85% reduction, data not shown).

Figure 6B:
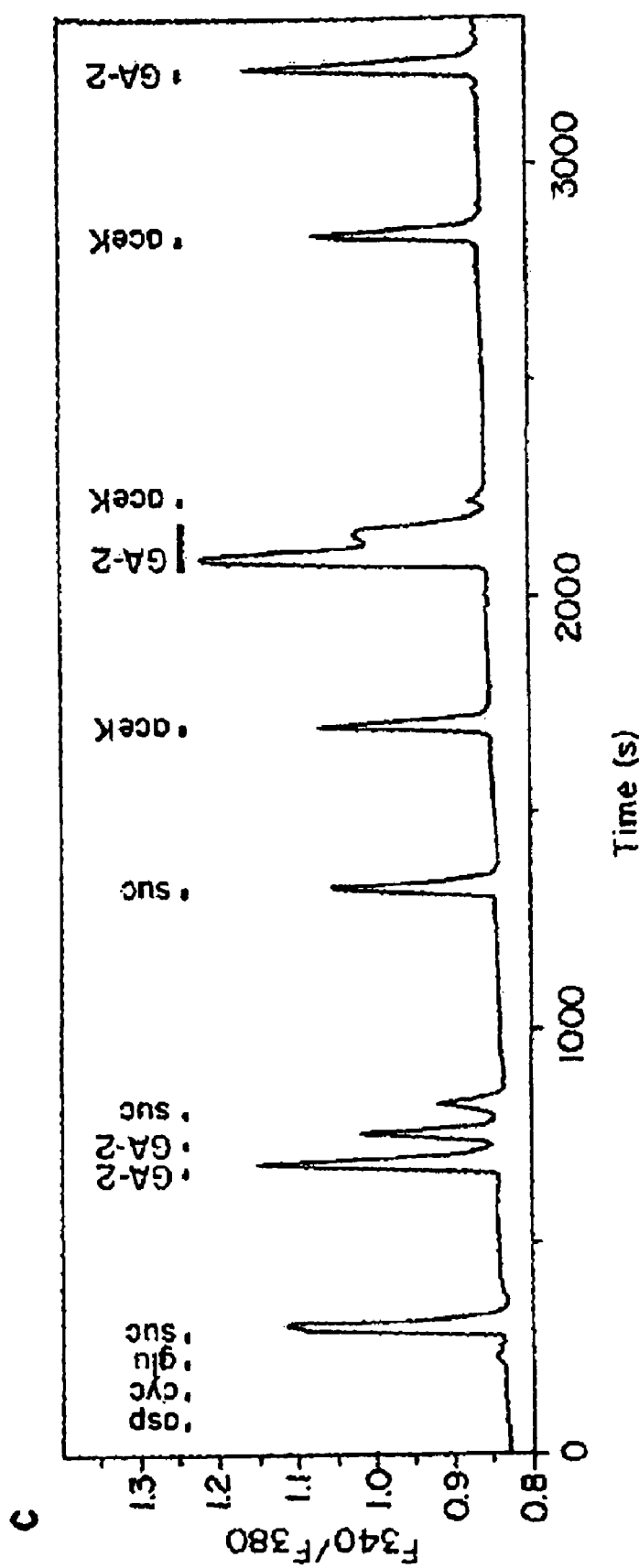

If the responses of T1R2+3 reflect the function of the native sweet receptor, we reasoned that the sensitivity thresholds seen in the cell-based assays should parallel the behavioral thresholds for detection of these sweet tastants in vivo. Indeed, FIG. 6b shows dose-responses for GA-2 (in vivo threshold ~2 μM), saccharin (in vivo threshold ~0.5 mM), acesulfame-K (in vivo threshold ~0.5 mM) and sucrose (in vivo threshold ~20 mM), demonstrating a good match between the cell-based responses and their biological threshold. No responses were detected against a panel of bitter tastants, or umami stimuli.

To examine the sweet taste responses in detail, cells transfected with T1R2+3 were placed on a microperfusion chamber and superfused with test solutions under various conditions. FIG. 6c shows that responses to the sweet tastants closely follow application of the stimulus (latency <1 s). As expected, when the tastant was removed, [Ca$^{2+}$]i returned to baseline. A prolonged exposure to the sweet compound (>10 s) resulted in adaptation: a fast increase of [Ca$^{2+}$]i followed by a rapid, but incomplete decline to the resting level. Similarly, successive applications of the tastant led to significantly reduced responses, indicative of desensitization (Lefkowitz et al., 1992), while a prolonged period of rest (>5 min) was required for full response recovery. As would be expected if T1R2+3 mediate the responses to the various sweet compounds (i.e., GA-2, sucrose and acesulfame-K), successive application of different tastants from this panel led to full cross-desensitization (FIG. 6c), while sweet tastants that did not activate this receptor complex (e.g. glucose and cyclamate) had no effect on the kinetics, amplitude or time course of the responses. Taken together, these results validate T1R2+3 as a sweet taste receptor.

We propose that all T1Rs encode sweet receptors: First, they are all members of the same receptor family. Second, T1R1, T1R2 and T1R3 are tightly co-expressed in distinct subsets of cells. Third, data is presented herein demonstrating that two of the three T1Rs combine to function as a validated sweet receptor.

Spatial Map of T1R and T2R Expression

Figure 7:
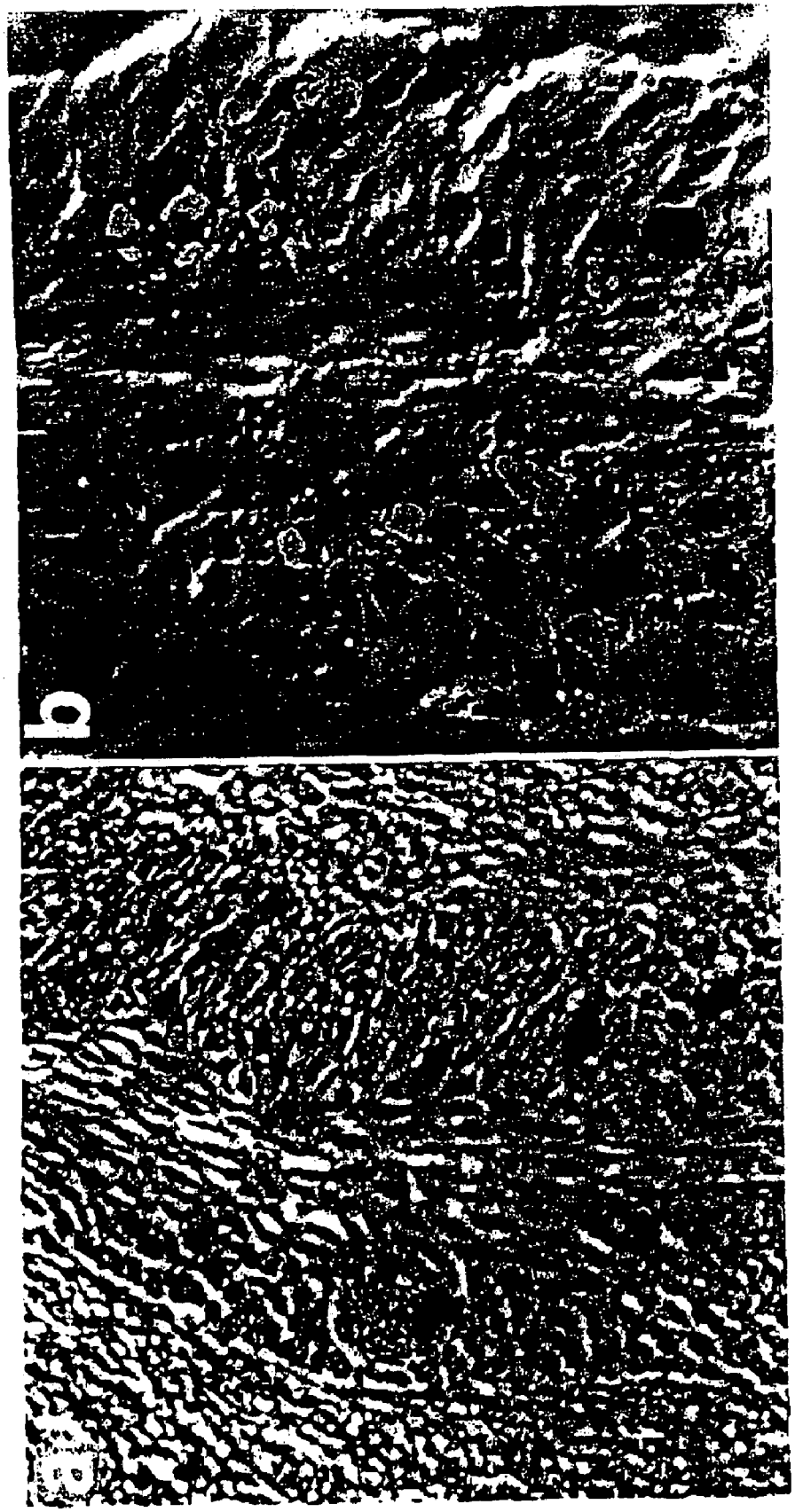
FIG. 7. T1Rs and T2Rs are segregated in distinct populations of taste receptor cells Double-label fluorescent in situ hybridization was used to examine the degree of overlap between the T1R and T2R families of sweet and bitter taste receptors. (a) T1R3 (green) and T2Rs (a mixture of 20 receptors, red) are never co-expressed. (b) A section through a circumvallate papilla is shown (b) as in panel (a), but with a mixture of all three T1Rs (green) versus twenty T2Rs in a foliate papilla.

Studying the expression of T1Rs in the context of other taste modalities may provide a view of the representation of sweet taste coding at the periphery. Recently, we showed that members of the T2R family of bitter taste receptors are rarely expressed in fungiform taste buds, but are present in 15-20% of the cells of all circumvallate, foliate and palate taste buds. Given that T1Rs are also expressed in the same taste buds, we examined whether there is overlap between T1R- and T2R-expressing cells. Double-labeling experiments using mixes of T1Rs and T2R probes demonstrated that T2Rs are not co-expressed with any of the T1R family members (FIG. 7, see also Adler et al., 2000). This was seen in all taste buds, and with mixes that included as many as 20 T2Rs. The strong segregation in the expression profile of these two receptor families makes an important prediction about the logic of taste coding and discrimination at the taste bud level: sweet and bitter are encoded by the activation of different cell types.

A prediction of this study is that taste buds in all taste papillae contain sweet receptor cells and that the anatomical representation of sweet sensitivity in the oral cavity should match the topographic distribution of T1R receptor expression. For instance, the back of the tongue and palate contain all of the T1R2+3 expressing cells, and so they would display high sensitivity for ligands of this receptor combination. Conversely, the front of the tongue would respond to the T1R1+3 combination, but poorly to the repertoire specific for T1R2+3. Moreover, since the front and back of the tongue are innervated by nerves originating in different ganglia (Mistretta and Hill, 1995), we conclude that T1R2+3 sweet cells must exhibit connectivity pathways that differ from those of T1R1+3 cells. Interestingly, the rat is known to be more sensitive to sucrose applied to the back of the tongue and palate, than to stimulation of the front of the tongue (Smith and Frank, 1993). Our expression and functional studies now provide a molecular explanation to these findings.

EXPERIMENTAL PROCEDURES

Molecular Cloning of T1R3

Human T1R3 was identified in the draft sequence of BAC clone RP5-89003 by homology to T1R1. A fragment of rat T1R3 was amplified from genomic DNA using degenerate PCR primers designed on the basis of the human sequence. The PCR derived probe was used to identify full-length rat T1R3 from a circumvallate cDNA library (Hoon et al., 1999) and to probe mouse BAC filter arrays (Incyte Genomics and Research Genetics). The sequences of T1R3 in Sac-taster and non-taster mouse strains (C57BL/6 and 129/Sv) were determined from the genomic clones. The sequence of the entire coding region of the gene of other mouse strains that are sweet sensitive: SWR, ST, C57L, FVB/N and sweet insensitive: DBA/1Lac, DBA/2, C3H, AKR, BALB/c was determined from amplified genomic DNA (Jackson Laboratory). For SWR mice, T1R3 was also sequenced from amplified taste-tissue cDNA. Amongst the 11 inbred strains, we found two taster alleles (taster 1: C57BL/6, C57L and taster 2: SWR, ST, FVB/N) and a single non-taster allele (DBA/1Lac, DBA/2, C3H, AKR, BALB/c, 129/Sv). Taster 1 and taster 2 alleles differ from each other in six amino acid positions (P61L, C261R, R371Q, S692L, I706T, G855E; one of this G855E, was missed by (Kitagawa et al., 2001; Max et al., 2001) likely due to its inclusion in the primers used in their amplifications reactions). Non-tasters differ from taster 1 allele in six residues (A55T, T60T, L61P, Q371R, T706T, E855G), and from taster 2 in 4 amino acid positions (A55T, T60I, R261C, L692S).

Mouse T1Rs were mapped using a mouse/hamster radiation hybrid panel (Research Genetics). Physical mapping of T1R3 involved PCR based typing of T1R3 positive BAC clones for the presence of STS-markers.

In Situ Hybridization

Tissue was obtained from adult mice. No sex-specific differences of expression patterns were observed. Therefore male and female animals were used interchangeably. For foliate sections, no differences in expression pattern were observed between the papillae. Fresh frozen sections (16 μm/section) were attached to silanized slides and prepared for in situ hybridization as described previously (Hoon et al., 1999). All in situ hybridizations were carried out at high stringency (hybridization, 5×SSC, 50% formamide, 65-72° C.; washing, 0.2×SSC, 72° C.). For single-label detection, signals were developed using alkaline-phosphatase conjugated antibodies to digoxigenin and standard chromogenic substrates (Boehringer Mannheim). Control hybridizations with sense probes produced no specific signals in any of the taste papillae. Cells were counted based on the position of their nucleus as previously described (Boughter et al., 1997). For double-label fluorescent detection, probes were labeled either with fluorescein or with digoxigenin. At least 50 taste buds from at least 3 different animals were analyzed with any combination of probes. An alkaline-phosphatase conjugated anti-fluorescein antibody (Amersham) and a horseradish-peroxidase conjugated anti-digoxigenin antibody were used in combination with fast-red and tyramide fluorogenic substrates (Boehringer Mannheim and New England Nuclear). Confocal images were obtained with a Leica TSC confocal microscope using an argon-krypton laser; 1-2 μm optical sections were recorded to ensure that any overlapping signal originated from single cells.

Generation of T1R3 Transgenic Mice and Behavioral Assays

An approximately 15 kb EcoRI fragment including the 6 coding exons of T1R3 and about 12 kb upstream of the starting ATG was isolated from a C57BL/6 BAC clone. This fragment contains the stop codon of the T1R3 coding sequence but lacks much of the 3'-UTR. The sequence of the entire 15 kb clone was determined from a taster and a non-taster strains. This fragment also contains the full sequence for a glycolipid transferase-like gene ~3 kb upstream of T1R3, but there are neither expression nor amino acid sequence differences in this gene between Sac taster (SWR) or non-taster (129/Sv) strains. In the transgenic construct, the bovine growth hormone polyadenylation (BGH) signal from pCDNA3.0 (Invitrogen) was ligated to the 3'-end of the T1R3 gene. This modification allowed PCR based genotyping of mice and permitted direct comparison of the expression of T1R3 from the transgene with that from the normal gene. Transgenic mice were generated by pronuclear injection of FVB/N oocytes. Since we determined that FVB/N mice are sensitive to sweet tastants, and carry a T1R3 taster allele, transgenic founders were crossed to 129/SvJ. F1-mice carrying the transgene were then back-crossed to 129/SvJ. F2 mice were typed for the presence of the transgene using the BGH tag, and for homozygosity of the endogenous non-taster T1R3 allele using a Bsp120I restriction polymorphism between FVB/N and 129/SvJ (see FIG. 2a). All four genetic groups were tested behaviorally. Mice were weaned at 3 weeks and trained for 7-10 days to drinking from two bottles of water prior to initiating testing.

For behavioral assays, 2 or 3 mice were housed per cage; mice derived from different transgenic founders (and males and females) were kept separate to allow comparison of the raw-data. The group sizes used for assays consisted of 4 or more cages, each with a minimum of 2 animals. Mice were always assayed at the low concentrations first (Fuller, 1974). In all cases, animals were given at least 2 days of water between concentration series. Each test consisted of a two-bottle choice assay over a 48 hr period; the positions of the bottles were switched after 24 hr. Preference ratios were calculated by dividing the consumption of the test solution by total intake. Data from each cage were individually analyzed to prevent systematic bias. The same assay was used to analyze the taste preferences of 129/Sv, C57BL/6 and FVB/N control mice.

Heterologous Expression of T1Rs

All receptors were cloned into a pEAK10 mammalian expression vector (Edge Biosystems, MD). Modified HEK-293 cells (PEAK$^{rapid}$ cells; Edge BioSystems, MD) were grown and maintained at 37° C. in UltraCulture medium (Bio Whittaker) supplemented with 5% fetal bovine serum, 100 μg/ml gentamycin sulphate (Fisher), 1 μg/ml amphotericin B and 2 mM GlutaMax I (Lifetechnologies). For transfection, cells were seeded onto matrigel coated 6-well culture plates, 24-well culture plates, or 35 mm recording chambers. After 24 h at 37° C., cells were washed in OptiMEM medium (Lifetechnologies) and transfected using LipofectAMINE reagent (Lifetechnologies). Transfection efficiencies were estimated by co-transfection of a GFP reporter plasmid, and were typically >70%. Activity assays were performed 36-48 h after transfection for cells transfected in 24-well culture plates and 35 mm recording chambers; cells transfected in 6-well culture plates were grown overnight, trypsinized, transferred to 96-well culture plates, and assayed 36-48 hours following re-seeding.

Calcium Imaging

Transfected cells were washed once in Hank's balanced salt solution containing 1 mM sodium pyruvate and 10 mM HEPES, pH 7.4 (assay buffer), and loaded with 2 μM FURA-2 AM (Molecular Probes) for 1 h at room temperature. The loading solution was removed and cells in 24-well plates were incubated with 250 μl of assay buffer (cells in 96-well plates were incubated with 50 μl) for 1 h to allow the cleavage of the AM ester. Cells expressing T1Rs and G proteins (Offermanns and Simon, 1995; Chandrashekar et al., 2000; Mody et al., 2000) in 24-well tissue culture plates were stimulated with 250 μl of a 2× tastant solution (cells in 96-well plates were stimulated with 50 μl of a 2× tastant solution). As a control for Gα15 and Gα16-Gz signaling a set of plates was co-transfected with mGluR1 and the μ-opioid receptor and assayed for responses to ACPD and DAMGO.

One of two imaging stations were used to measure $[Ca^{2+}]i$ changes. One system comprises of a Nikon Diaphot 200 microscope equipped with a 10×/0.5 fluor objective, the TILL imaging system (T.I.L.L Photonics GmbH), and a cooled CCD camera. Acquisition and analysis of these fluorescence images used TILL-Vision software. Also, an Olympus IX-70/ FLA microscope equipped with a 10×/0.5 fluor objective, a variable filter wheel (Sutter Instruments), and an intensified CCD camera (Sutter Instruments) was utilized. VideoProbe software (Instrutech) was used for acquisition and analysis of these fluorescence images. Generally, individual responses were measured for 60 s. The $F_{340}/F_{380}$ ratio was analyzed to measure $[Ca^{2+}]i$.

Kinetics of activation and deactivation were measured using a bath perfusion system. Cells were seeded onto a 150 μl microperfusion chamber, and test solutions were pressure-ejected with a picospritzer apparatus (General Valve, Inc.). Flow-rate was adjusted to ensure complete exchange of the bath solution within 4 s. Responses were measured from 80 individual responding cells.

List of Tastants

The following tastants were tested, with the following typical maximal concentrations: sucrose (250 mM), sodium saccharin (25 mM), N-methyl saccharin (5 mM), dulcin (2 mM), aspartame (2 mM), palatinose (250 mM), sodium cyclamate (15 mM), guanidinoacetic acid-1 (1 mM), guanidinoacetic acid-2 (1 mM), guanidinoacetic acid-3 (1 mM), acesulfame-K (10 mM), glucose (250 mM), maltose (250 mM), lactose (250 mM), fructose (250 mM), galactose (250 mM), xylitol (250 mM), raffinose (250 mM), sorbitol (250 mM), trehalose (250 mM), thaumatin (0.1%), monellin (0.1%), alanine (20 mM), glycine (20 mM), arginine (20 mM), monosodium glutamate (20 mM), cycloheximide (5 μM), denatonium (10 mM), phenyl-thiocarbamide (2.5 mM).

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

What is claimed is:

1. An isolated receptor, wherein the receptor comprises a first polypeptide and a second polypeptide, wherein the first polypeptide has at least 93% amino acid sequence identity to SEQ ID NO:20, or at least 94% amino acid sequence identity to SEQ ID NO:23, and wherein the second polypeptide has at least 92% amino acid sequence identity to SEQ ID NO:8.

2. The isolated receptor of claim 1, wherein the receptor is a sweet taste receptor.

3. The isolated receptor of claim 1, wherein the first polypeptide has the amino acid sequence of SEQ ID NO:20.

4. The isolated receptor of claim 1, wherein the first polypeptide has the amino acid sequence of SEQ ID NO:23.

5. The isolated receptor of claim 1, wherein the first polypeptide is encoded by a nucleotide sequence of SEQ ID NO:19 or SEQ ID NO:22.

6. The isolated receptor of claim 1, wherein the second polypeptide has the amino acid sequence of SEQ ID NO:8.

7. The isolated receptor of claim 1, wherein the second polypeptide is encoded by a nucleotide sequence of SEQ ID NO:11.

8. The isolated receptor of claim 1, wherein the first polypeptide is recombinant.

9. A host cell comprising the isolated receptor of claim 8.

10. The isolated receptor of claim 1, wherein the first polypeptide and the second polypeptide are recombinant.

11. A host cell expressing the recombinant receptor of claim 10.

12. The isolated receptor of claim 1, wherein the second polypeptide is recombinant.

13. A host cell expressing the recombinant receptor of claim 12.

14. The isolated receptor of claim 1, wherein the first polypeptide and the second polypeptide are non-covalently linked.

15. The isolated receptor of claim 1, wherein the first polypeptide and the second polypeptide are covalently linked.

16. The isolated receptor of claim 1, wherein the receptor specifically binds to an antibody that specifically binds to a polypeptide comprising SEQ ID NO:20 or SEQ ID NO:23.

17. A method of identifying a compound that activates or inhibits signal transduction in cells, the method comprising the steps of:

(i) contacting the compound with a cell expressing the receptor of claim 1 in the plasma membrane of the cell; and (ii) determining a functional effect of the compound upon the receptor, wherein said functional effect is binding to the receptor or having an effect on the activity of the receptor, thereby identifying a compound that activates or inhibits signal transduction.

18. The method of claim 17, wherein the first polypeptide has the amino acid sequence of SEQ ID NO: 20 or 23.

19. The method of claim 17, wherein the second polypeptide has the amino acid sequence of SEQ ID NO:8.

20. The method of claim 17, wherein the functional effect is determined by measuring binding of the compound to the receptor.

21. The method of claim 17, wherein the functional effect is determined by measuring ligand binding to the receptor.

22. The method of claim 17, wherein the functional effect is a chemical or phenotypic effect.

23. The method of claim 17, wherein the functional effect is determined by measuring changes in intracellular cAMP, IP3, or Ca2+.

24. The method of claim 17, wherein the cell is a mammalian cell.

25. The method of claim 24, wherein the cell is a human cell.

26. The method of claim 17, wherein the first polypeptide and the second polypeptide are non-covalently linked.

27. The method of claim 17, wherein the first polypeptide and the second polypeptide are covalently linked.

28. The method of claim 17, wherein the first polypeptide and the second polypeptide are both recombinant.

29. A method of identifying a compound that activates or inhibits signal transduction in cells, the method comprising the steps of: (i) contacting the compound with a cell expressing the receptor of claim 1 in the plasma membrane of the cell, and (ii) determining a functional effect of the compound upon the receptor, wherein said functional effect is binding to the receptor or having an effect on the activity of the receptor, thereby identifying a compound that activates or inhibits signal transduction, wherein the receptor specifically binds compound, and at least one of the first and second polypeptides is recombinant.

* * * * *

UNITED STATES PATENT AND TRADEMARK OFFICE
CERTIFICATE OF CORRECTION

| | | |
|---|---|---|
| PATENT NO. | : 7,977,060 B2 | Page 1 of 1 |
| APPLICATION NO. | : 12/147415 | |
| DATED | : July 12, 2011 | |
| INVENTOR(S) | : Charles S. Zuker et al. | |

It is certified that error appears in the above-identified patent and that said Letters Patent is hereby corrected as shown below:

Title page item (75), after the inventor Mark A. Hoon:

Please delete "Kensington, MA" and insert --Kensington, MD--.

Signed and Sealed this
Thirteenth Day of March, 2012

David J. Kappos
*Director of the United States Patent and Trademark Office*